United States Patent
Afar et al.

(10) Patent No.: US 7,771,968 B2
(45) Date of Patent: Aug. 10, 2010

(54) GENE UPREGULATED IN CANCERS OF THE PROSTATE

(75) Inventors: Daniel E. H. Afar, Fremont, CA (US); Arthur B. Raitano, Los Angeles, CA (US); Rene S. Hubert, Los Angeles, CA (US); Steve Chappell Mitchell, Gurnee, IL (US); Aya Jakobovits, Beverly Hills, CA (US)

(73) Assignee: Agensys, Inc., Santa Monica, CA (US)

( * ) Notice: Subject to any disclaimer, the term of this patent is extended or adjusted under 35 U.S.C. 154(b) by 0 days.

(21) Appl. No.: 12/170,208

(22) Filed: Jul. 9, 2008

(65) Prior Publication Data

US 2009/0074797 A1    Mar. 19, 2009

Related U.S. Application Data

(63) Continuation of application No. 10/959,697, filed on Oct. 5, 2004, now abandoned, which is a continuation of application No. 09/697,206, filed on Oct. 26, 2000, now Pat. No. 6,893,818.

(60) Provisional application No. 60/162,364, filed on Oct. 28, 1999.

(51) Int. Cl.
C12N 15/00    (2006.01)
(52) U.S. Cl. ............ 435/69.1; 435/240.2; 435/252.3; 435/254.2; 536/23.1
(58) Field of Classification Search .............. 435/69.1, 435/240.2, 252.3, 254.2; 536/23.1
See application file for complete search history.

(56) References Cited

U.S. PATENT DOCUMENTS

| | | |
|---|---|---|
| 4,179,337 A | 12/1979 | Davis et al. |
| 4,301,144 A | 11/1981 | Iwashita et al. |
| 4,496,689 A | 1/1985 | Mitra |
| 4,640,835 A | 2/1987 | Shimizu et al. |
| 4,670,417 A | 6/1987 | Iwasaki et al. |
| 4,736,866 A | 4/1988 | Leder et al. |
| 4,791,192 A | 12/1988 | Nakagawa et al. |
| 4,870,009 A | 9/1989 | Evans et al. |
| 5,382,510 A | 1/1995 | Levine et al. |
| 5,428,130 A | 6/1995 | Capon et al. |
| 5,723,286 A | 3/1998 | Dower et al. |
| 5,733,731 A | 3/1998 | Schatz et al. |
| 5,837,501 A | 11/1998 | Beumer et al. |
| 5,840,501 A | 11/1998 | Allard et al. |
| 5,846,722 A | 12/1998 | Kauvar et al. |
| 5,919,652 A | 7/1999 | Pang et al. |
| 5,925,523 A | 7/1999 | Dove et al. |
| 5,928,868 A | 7/1999 | Liu et al. |
| 5,939,533 A | 8/1999 | Lilja et al. |
| 5,952,170 A | 9/1999 | Stroun et al. |
| 5,955,280 A | 9/1999 | Vidal et al. |
| 6,004,746 A | 12/1999 | Brent et al. |
| 6,262,333 B1 | 7/2001 | Endege et al. |
| 6,331,427 B1 | 12/2001 | Robison |
| 6,387,697 B1 | 5/2002 | Yuqiu et al. |
| 2002/0004491 A1 | 1/2002 | Xu et al. |
| 2002/0085998 A1 | 7/2002 | Jiang et al. |
| 2002/0102602 A1 | 8/2002 | Yuqiu et al. |
| 2002/0172952 A1 | 11/2002 | Henderson et al. |
| 2002/0197669 A1 | 12/2002 | Bangur et al. |

FOREIGN PATENT DOCUMENTS

| | | |
|---|---|---|
| CN | 1351081 | 5/2002 |
| EP | 1 074 617 | 2/2001 |
| WO | WO-95/14772 | 6/1995 |
| WO | WO-98/16628 | 4/1998 |
| WO | WO-98/24893 | 6/1998 |
| WO | WO-99/06550 | 2/1999 |
| WO | WO-99/38972 | 8/1999 |
| WO | WO-99/58675 | 11/1999 |
| WO | WO-99/64576 | 12/1999 |
| WO | WO-00/15799 | 3/2000 |
| WO | WO-00/21991 | 4/2000 |
| WO | WO-00/55177 | 9/2000 |
| WO | WO-00/55350 | 9/2000 |
| WO | WO-00/60076 | 10/2000 |
| WO | WO-01/00828 | 1/2001 |
| WO | WO-01/18046 | 3/2001 |
| WO | WO-01/18542 | 3/2001 |
| WO | WO-01/22920 | 4/2001 |
| WO | WO-01/31012 | 5/2001 |
| WO | WO-01/49716 | 7/2001 |
| WO | WO-01/55302 | 8/2001 |

(Continued)

OTHER PUBLICATIONS

Schmid S et al, 2001 (J comparative Neurology, 430(2): 160-71).*

(Continued)

*Primary Examiner*—Larry R. Helms
*Assistant Examiner*—Minh-Tam Davis
(74) *Attorney, Agent, or Firm*—Morrison & Foerster LLP

(57) ABSTRACT

The present invention relates to a novel protein designated 20P2H8 which shares homology with several heterogeneous nuclear ribonucleoproteins (hnRNPs). A full length approximately 3600 bp 20P2H8 cDNA (SEQ ID NO: 1, encoding a 517 amino acid open reading frame (SEQ ID NO: 2), is provided herein.

9 Claims, 13 Drawing Sheets

FOREIGN PATENT DOCUMENTS

| | | |
|---|---|---|
| WO | WO-01/55314 | 8/2001 |
| WO | WO-01/79286 | 10/2001 |
| WO | WO-01/92581 | 12/2001 |
| WO | WO-01/94629 | 12/2001 |
| WO | WO-01/96388 | 12/2001 |
| WO | WO-01/96390 | 12/2001 |
| WO | WO-02/00677 | 1/2002 |
| WO | WO-02/04514 | 1/2002 |
| WO | WO-02/08456 | 1/2002 |
| WO | WO-02/10449 | 2/2002 |
| WO | WO-02/29103 | 4/2002 |
| WO | WO-02/39885 | 5/2002 |
| WO | WO-02/058534 | 8/2002 |
| WO | WO-02/060317 | 8/2002 |
| WO | WO-02/070539 | 9/2002 |
| WO | WO-02/077013 | 10/2002 |
| WO | WO-02/081749 | 10/2002 |
| WO | WO-02/083070 | 10/2002 |
| WO | WO-02/083956 | 10/2002 |
| WO | WO-02/095000 | 11/2002 |
| WO | WO-03/004989 | 1/2003 |
| WO | WO-03/010329 | 2/2003 |

OTHER PUBLICATIONS

Conner et al, 1996 (Mol Brain Res, 42: 1-17).*
Guate et al, 1999 (BJU Internatl, 84: 495-502).*
Alanen et al., Pathol. Res. Pract. (1996) 192(3):233-237.
Alers et al., Lab. Invest. (1997) 77(5):437-438.
Altschul et al., Methods in Enzymology (1996) 266:460-480.
Anderson and Seilhamer, Electrophoresis (1997) 18:533-537.
Arlen et al., Crit. Rev. Immunol. (1998) 18:133-138.
Arthur et al., Cancer Gene Ther. (1997) 4:17-25.
Ashley et al., J. Exp. Med. (1997) 186:1177-1182.
Baisden et al., Am. J. Surg. Pathol. (1999) 23(8):918-924.
Beerli et al., J. Biol. Chem. (1994) 289:23931-23936.
Birren et al., Sep. 13, 2000, GEMBL:AC009692, XP2164433.
Bocking et al., Anal. Quant. Cytol. (1984) 6(2):74-88.
Boon, Adv. Can. Res. (1992) 58:177-210.
Bowie et al., Science (1990) 257:1306-1310.
Brooks et al., Cancer Epidemiol. Biomarkers Prev. (1998) 7:531-536.
Burgess et al., J. Cell Biol. (1990) 111:2129-2138.
Bzdega et al., J. Neurochem. (1997) 69:2270.
Caetano-Anolles, Biotechniques (1998) 25(3):472-476, 478-480.
Carter et al., Nucl. Acids Res. (1986) 13:4331.
Carter et al., Proc. Natl. Acad. Sci. USA (1993) 89:4285.
Carter et al., Proc. Natl. Acad. Sci. USA (1996) 93:749.
Chen et al., Lab. Invest. (1998) 78(2):165-174.
Chothia, J. Mol. Biol. (1976) 150:1.
Cohen, Oligodeoxynucleotides, Antisense Inhibitors of Gene Expression, CRC Press; and Synthesis (1988) 1:1-5.
Couture and Stinchcomb, Trends Genet. (1996) 12:510-515.
Crystal, Science (1995) 270:404-410.
Cupp and Osterling, Mayo Clinic Proc. (1993) 68:297-306.
Curti, Crit. Rev. in Oncology/Hematology (1993) 14:29-39.
De Marzo et al., Am. J. Pathol. (1999) 155(6):1985-1992.
Dennis et al., Biochim. Biophys. Acta (1999) 1473(1):21-34.
Deonarain, Expert Opin. Ther. Pat. (1998) 8:53-69.
Deshane et al., Gene Ther. (1994) 1:332-337.
Donnelly et al., Ann. Rev. Immunol. (1997) 15:617-648.
Drexler et al., Leukemia and Lymphoma (1993) 9:1-25.
Durrant, Anticancer Drugs (1997) 8:727-733.
Embleton et al., Immunol. Ser. (1984) 23:181-207.
Epstein, Hum. Pathol. (1995) 26(2):223-229.
Evans et al., Am. J. Obstet. Gynecol. (1994) 171(4):1055-1057.
Ezzell, J. NIH Res. (1995) 7:46-49.
Falk et al., Nature (1991) 351:290-296.
Fong et al., J. Immunol. (1997) 159:3113-3117.
Foon et al., J. Clin. Invest. (1995) 96:334-342.
Fortier et al., J. Nat. Cancer Inst. (1999) 91(19):1635-1640.
Fu et al., EMBO J. (1996) 15:4392-4401.
Funakoshi et al., J. Immunother. Emphasis Tumor Immunol. (1996) 19:93-101.
Gaiddon et al., Endocrinology (1995) 136(10):4331-4338.
Gao et al., Prostate (1997) 31:264-281.
Ghossein et al., J. Clin. Oncol. (1995) 13:1195-2000.
Goffman et al., Cancer Genet. Cytogenet. (1983) 8(3):197-202.
Greenbaum et al., Genome Biology (2003) 4(9):117.1-117.8.
Grever et al., J. Comp. Neurol. (1996) 376(2):306-314.
Guo et al., Journal of Pharmacology and Experimental Therapeutics (2002) 300:206-212.
Gura, Science (1997) 278:1041-1042.
Hall et al., Nucleic Acids Research (1996) 24(6):1119-1126.
Hamilton et al., Biochem. Biophys. Res. Commun. (1999) 261:646-651.
Hartwell et al., Science (1997) 278:1064-1068.
Hebbes et al., Mol. Immunol. (1989) 26(9):865-873.
Henderson et al., Cancer Res. (1996) 56:3763-3770.
Herlyn et al., Cancer Immunol. Immunother. (1996) 43:65-76.
Heston et al., Clin. Chem. (1995) 41:1687-1688.
Hodge et al., Int. J. Cancer (1995) 63:231-237.
Honore et al., J. Biol. Chem. (1995) 270:28780.
Hubert et al., "Identification of Differentially Expressed Genes Using Prostate Cancer Xenograft Models," 1999, XP-002120376.
Hunt et al., Science (1992) 255:1261-1263.
Isaacs et al., Cancer Surv. (1995) 23:19-32.
Israeli et al., Cancer Res. (1994) 54:1807.
Iyer et al., J. Am. Chem. Soc. (1990) 112:1253-1254.
Iyer et al., J. Org. Chem. (1990) 55:4693-4698.
J. Urol. (1995) 154(2 Pt 1):474-478.
Jain, Sci. Am. (1994) 271:58-65.
Jakobovits, Exp. Opin. Invest. Drugs (1998) 7(4):607-614.
Jarrard, J. Urol. (2000) 163(4):1189-1190.
Jones et al., Nature (1986) 321:522-525.
Kasprzyk et al., Cancer Res. (1992) 52:2771-2776.
Kawabata et al., Feb. 22, 2000, GenBank Accession No. AK000178.
Kennedy et al., Nat. Genet. (1996) 12(3):329-331.
Klein et al., Nature Medicine (1997) 3:402-408.
Kozak, Mol. Cell Biol. (1989) 9:5073-5080.
Lazar et al., Molecular and Cellular Biology (1988) 8:1247-1252.
Lethe et al., Int. J. Cancer (1998) 76(6):903-908.
Li et al., Cell (1992) 69:915.
Li et al., J. Biol. Chem. (2000) 275(30):23053-23058.
Lodish et al., Molecular Cell Biology, 4$^{th}$ ed., W.H. Freeman and Company, 2000, p. 531.
Marrogi et al., J. Cutan. Pathol. (1999) 26(8):369-378.
Merrill et al., J. Urol. (2000) 163(2):503-512.
Miller, FASEB J. (1995) 9:190-199.
Minimoto et al., Cancer Detect. Prev. (2000) 24(1):1-12.
Morton and Myszka, Methods in Enzymology (1998) 295:268.
Moun et al., Cancer Res. (1994) 54:6160-6166.
MPSRCH search report, 2002, us-09-697-206a-1.rng, pp. 12-13.
MPSRCH search report, 2002, us-09-697-206a-1.rni, pp. 1-2.
MPSRCH search result, 2006, us-10-959-697.2.rai.result 11, pp. 1-2.
Muller et al., MCB (1991) 11:1785.
Murphy et al., Prostate (1996) 29:371-380.
O'Brian, Oncol. Rep. (1998) 5(2):305-309.
Oh et al., Proteomics (2001) 1:1303-1319.
Ozaki et al., Blood (1997) 90:3179-3186.
Parker et al., J. Immunol. (1992) 149:3580-3587.
Parker et al., J. Immunol. (1994) 152:163-175.
Partridge et al., Antisense and Nucleic Acid Drug Development (1996) 6:169-175.
Peri and Pandey, Trends in Genetics (2001) 17:685-687.
Peshwa et al., Prostate (1998) 36:129-138.
Peterziel et al., Oncogene (1999) 18(46):6322-6329.
Polascik et al., J. Urol. (1999) 162(2):293-306.
Raju et al., Exp. Cell Res. (1997) 235(1):145-154.
Reinstein et al., Oncogene (2000) 19:5944-5950.
Reiter et al., Proc. Natl. Acad. Sci. USA (1998) 95:1735.
Restifo, Curr. Opin. Immunol. (1996) 8:658-663.
Reynolds et al., Int. J. Cancer (1997) 72:972-976.
Ribas et al., Cancer Res. (1997) 57:2865-2869.
Richardson et al., Proc. Natl. Acad. Sci. USA (1995) 92:3137-3141.

Riechmann et al., Nature (1988) 332:323-327.
Robertson et al., Methods Mol. Biol. (1998) 98:121-154.
Sawai et al., Fetal Diagn. Ther. (1996) 11(6):407-413.
Schlessenger et al., Curr. Opin. Genet. Dev. (1994) 4:25.
Schwartz et al., J. Immunol. (1985) 135(4):2598-2608.
Sharief et al., Biochem. Mol. Biol. Int. (1994) 33(3):567-574.
Shepard et al., J. Clin. Immunol. (1991) 11:117-127.
Shnyreva et al., J. Biol. Chem. (2000) 19;275:15498-15503.
Sims et al., J. Immunol. (1993) 151:2296.
Sodee et al., Clin. Nuc. Med. (1996) 21:759-766.
Spitler, Cancer Biotherapy (1995) 10:1-3.
Stephan et al., Urology (2000) 55(4):560-563.
Storrie et al., Methods Enzymology (1990) 182:203-225.
Su et al., Proc. Natl. Acad. Sci. USA (1996) 93:7252.
Takahama, Forensic Sci. Int. (1996) 80(1-2):63-69.
Thomas, Proc. Natl. Acad. Sci. USA (1980) 77:5201-5205.
Thomas and Capecchi, Cell (1987) 51:503.
Thorson et al., Mod. Pathol. (1998) 11(6):543-551.
Tian et al., Physiol. Genomics (2004) 17:170-182.
Tjoa et al., Prostate (1996) 28:65-69.
Tsunenari et al., Blood (1997) 90:2437-2444.
Tulchinsky et al., Int. J. Mol. Med. (1999) 4(1):99-102.

Van Den Eynde and Boon, Int. J. Clin. Lab. Res. (1997) 27:81-86.
Vaughan et al., Nature Biotechnology (1998) 16:535-539.
Velders et al., Cancer Res. (1995) 55:4398-4403.
Verhoeyen et al., Science (1988) 239:1534-1536.
Verkaik et al., Urol. Res. (1995) 25:373-384.
Verma, Nature (1997) 389:239-242.
Wagner et al., Hybridoma (1997) 16:33-40.
Walter et al., Nat. Genetics (1994) 7:22.
Welch et al., Int. J. Cancer (1989) 43:449-457.
Welford, Opt. Quant. Elect. (1991) 23:1.
Wells et al., Gene (1985) 34:315.
Wells et al., Philos. Trans. R. Soc. London Ser. A (1986) 317:415.
White et al., Ann. Rev. Med. (2001) 52:125-145.
Wolff et al., Cancer Res. (1993) 53:2560-2565.
Xiao et al., Blood (2000) 96(2):699-704.
Xue et al., Prostate (1997) 30:73-78.
Yeatment et al., Clin. Exp. Metastasis (1996) 14(3):246-252.
Yokota et al., Oncogene (1988) 3:471-475.
Zhong et al., Leuk. Res. (1996) 20:581-589.
Zimmer, Cell Motility and the Cytoskeleton (1991) 20:325-337.
Zoller et al., Nucl. Acids Res. (1987) 10:6487.

\* cited by examiner

FIG. 1

```
        1              20             29             38             47             56
5' CTT TTT GGG ATC ACT GCT GGG GCC ACC GGG GCC AAG CTA GGC TCG GAT GAG AAG
   --- --- --- --- --- --- --- --- --- --- --- --- --- --- --- --- --- ---
    L   F   G   I   T   A   G   A   T   G   A   K   L   G   S   D   E   K 65             74             83             92            101            110
   GAG TTG ATC CTG CTG TTC TGG AAA GTC GTG GAT CTG GCC AAC AAG AAG GTG GGA
   --- --- --- --- --- --- --- --- --- --- --- --- --- --- --- --- --- ---
    E   L   I   L   L   F   W   K   V   V   D   L   A   N   K   K   V   G 119            128            137            146            155            164
   CAG TTG CAC GAA GTG CTA GTT AGA CCG GAT CAG TTG GAA CTG ACG GAG GAC TGC
   --- --- --- --- --- --- --- --- --- --- --- --- --- --- --- --- --- ---
    Q   L   H   E   V   L   V   R   P   D   Q   L   E   L   T   E   D   C 173            182            191            200            209            218
   AAA GAA GAA ACT AAA ATA GAC GTC GAA AGC CTG TCC TCG GCG TCG CAG CTG GAC
   --- --- --- --- --- --- --- --- --- --- --- --- --- --- --- --- --- ---
    K   E   E   T   K   I   D   V   E   S   L   S   S   A   S   Q   L   D 227            236            245            254            263            272
   CAA GCC CTC CGA CAG TTT AAC CAG TCA GTG AGC AAT GAA CTG AAT ATT GGA GTA
   --- --- --- --- --- --- --- --- --- --- --- --- --- --- --- --- --- ---
    Q   A   L   R   Q   F   N   Q   S   V   S   N   E   L   N   I   G   V 281            290            299            308            317            326
   GGG ACT TCC TTC TGT CTC TGT ACT GAT GGG CAG CTT CAT GTC AGG CAA ATC CTG
   --- --- --- --- --- --- --- --- --- --- --- --- --- --- --- --- --- ---
    G   T   S   F   C   L   C   T   D   G   Q   L   H   V   R   Q   I   L 335            344            353            362            371            380
   CAT CCT GAG GCT TCC AAG AAG AAT GTA CTA TTA CCT GAA TGC TTC TAT TCC TTT
   --- --- --- --- --- --- --- --- --- --- --- --- --- --- --- --- --- ---
    H   P   E   A   S   K   K   N   V   L   L   P   E   C   F   Y   S   F 389            398            407            416            425            434
   TTT GAT CTT CGA AAA GAA TTC AAG AAA TGT TGC CCT GGT TCA CCT GAT ATT GAC
   --- --- --- --- --- --- --- --- --- --- --- --- --- --- --- --- --- ---
    F   D   L   R   K   E   F   K   K   C   C   P   G   S   P   D   I   D 443            452            461            470            479            488
   AAA CTG GAC GTT GCC ACA ATG ACA GAG TAT TTA AAT TTT GAG AAG AGT AGT TCA
   --- --- --- --- --- --- --- --- --- --- --- --- --- --- --- --- --- ---
    K   L   D   V   A   T   M   T   E   Y   L   N   F   E   K   S   S   S 497            506            515            524            533            542
   GTC TCT CGA TAT GGA GCC TCT CAA GTT GAA GAT ATG GGG AAT ATA ATT TTA GCA
   --- --- --- --- --- --- --- --- --- --- --- --- --- --- --- --- --- ---
    V   S   R   Y   G   A   S   Q   V   E   D   M   G   N   I   I   L   A 551            560            569            578            587            596
   ATG ATT TCA GAG CCT TAT AAT CAC ACG TTT TCA GAT CCA GAG ACA GTG AAT TAC
   --- --- --- --- --- --- --- --- --- --- --- --- --- --- --- --- --- ---
    M   I   S   E   P   Y   N   H   R   F   S   D   P   E   R   V   N   Y 605            614            623            632            641            650
   AAG TTT GAA AGT GGA ACT TGC AGC AAG ATG GAA CTT ATT GAT GAT AAC ACC GTA
   --- --- --- --- --- --- --- --- --- --- --- --- --- --- --- --- --- ---
    K   F   E   S   G   T   C   S   K   M   E   L   I   D   D   N   T   V 659            668            677            686            695            704
   GTC AGG GCA CGA GGT TTA CCA TGG CAG TCT TCA GAT CAA GAT ATT GCA AGA TTC
   --- --- --- --- --- --- --- --- --- --- --- --- --- --- --- --- --- ---
    V   R   A   R   G   L   P   W   Q   S   S   D   Q   D   I   A   R   F
```

FIG. 1-2

```
        713         722         731         740         749         758
TTC AAA GGA CTC AAT ATT GCC AAG GGA GGT GCA GCA CTT TGT CTG AAT GCT CAG
--- --- --- --- --- --- --- --- --- --- --- --- --- --- --- --- --- ---
 F   K   G   L   N   I   A   K   G   G   A   A   L   C   L   N   A   Q 767         776         785         794         803         812
GGT CGA AGG AAC GGA GAA GCT CTG GTT AGG TTT GTA AGT GAG GAG CAC CGA GAC
--- --- --- --- --- --- --- --- --- --- --- --- --- --- --- --- --- ---
 G   R   R   N   G   E   A   L   V   R   F   V   S   E   E   H   R   D 821         830         839         848         857         866
CTA GCA CTA CAG AGG CAC AAA CAT CAC ATG GGG ACC CGG TAT ATT GAG GTT TAC
--- --- --- --- --- --- --- --- --- --- --- --- --- --- --- --- --- ---
 L   A   L   Q   R   H   K   H   H   M   G   T   R   Y   I   E   V   Y 875         884         893         902         911         920
AAA GCA ACA GGT GAA GAT TTC CTT AAA ATT GCT GGT GGT ACT TCC AAT GAG GTA
--- --- --- --- --- --- --- --- --- --- --- --- --- --- --- --- --- ---
 K   A  |T   G   E   D   F   L   K   I| A   G   G   T   S   N   E   V 929         938         947         956         965         974
GCC CAG TTT CTC TCC AAG GAA AAT CAA GTC ATT GTT CGC ATG CGG GGG CTC CCT
--- --- --- --- --- --- --- --- --- --- --- --- --- --- --- --- --- ---
 A   Q   F   L   S   K   E   N   Q   V   I  |V   R   M   R   G   L|  P 983         992        1001        1010        1019        1028
TTC ACG GCC ACA GCT GAA GAA GTG GTG GCC TTC TTT GGA CAG CAT TGC CCT ATT
--- --- --- --- --- --- --- --- --- --- --- --- --- --- --- --- --- ---
 F   T   A   T   A   E   E   V   V   A   F   F   G   Q   H   C   P   I 1037        1046        1055        1064        1073        1082
ACT GGG GGA AAG GAA GGC ATC CTC TTT GTC ACC TAC CCA GAT GGT AGG CCA ACA
--- --- --- --- --- --- --- --- --- --- --- --- --- --- --- --- --- ---
 T   G   G   K   E   G   I   L   F   V   T   Y   P   D   G   R   P  |T|

1091        1100        1109        1118        1127        1136
GGG GAC GCT TTT GTC CTC TTT GCC TGT GAG GAA TAT GCA CAG AAT GCG TTG AGG
--- --- --- --- --- --- --- --- --- --- --- --- --- --- --- --- --- ---
|G   D   A   F   V   L   F|  A   C   E   E   Y   A   Q   N   A   L   R 1145        1154        1163        1172        1181        1190
AAG CAT AAA GAC TTG TTG GGT AAA AGA TAC ATT GAA CTC TTC AGG AGC ACA GCA
--- --- --- --- --- --- --- --- --- --- --- --- --- --- --- --- --- ---
 K   H   K   D   L   L   G   K   R   Y   I   E   L   F   R   S   T   A 1199        1208        1217        1226        1235        1244
GCT GAA GTT CAG CAG GTG CTG AAT CGA TTC TCC TCG GCC CCT CTC ATT CCA CTT
--- --- --- --- --- --- --- --- --- --- --- --- --- --- --- --- --- ---
 A   E   V   Q   Q   V   L   N   R   F   S   S   A   P   L   I   P   L

1253        1262        1271        1280        1289        1298
CCA ACC CCT CCC ATT ATT CCA GTA CTA CCT CAG CAA TTT GTG CCC CCT ACA AAT
--- --- --- --- --- --- --- --- --- --- --- --- --- --- --- --- --- ---
P   T   P   P   I   I   P   V   L   P   Q   Q   F   V   P   P  T   N 1307        1316        1325        1334        1343        1352
GTT AGA GAC TGT ATA CGC CTT CGA GGT CTT CCC TAT GCA GCC ACA ATT GAG GAC
--- --- --- --- --- --- --- --- --- --- --- --- --- --- --- --- --- ---
 V   R   D   C  |I   R   L   R   G   L|  P   Y   A   A   T   I   E   D 1361        1370        1379        1388        1397        1406
ATC CTG GAT TTC CTG GGG GAG TTC GCC ACA GAT ATT CGT ACT CAT GGG GTT CAC
--- --- --- --- --- --- --- --- --- --- --- --- --- --- --- --- --- ---
```

FIG. 1-3

```
                I   L   D   F   L   G   E   F   A   T   D   I   R   T   H   G   V   H 1415        1424        1433        1442        1451        1460
ATG GTT TTG AAT CAC CAG GGC CGC CCA TCA GGA GAT GCC TTT ATC CAG ATG AAG
--- --- --- --- --- --- --- --- --- --- --- --- --- --- --- --- --- ---
 M   V   L   N   H   Q   G   R   P   S   D   A   F   I   Q   M   K 1469        1478        1487        1496        1505        1514
TCT GCG GAC AGA GCA TTT ATG GCT GCA CAG AAG TGT CAT AAA AAA AAC ATG AAG
--- --- --- --- --- --- --- --- --- --- --- --- --- --- --- --- --- ---
 S   A   D   R   A   F   M   A   A   Q   K   C   H   K   K   N   M   K 1523        1532        1541        1550        1559        1568
GAC AGA TAT GTT GAA GTC TTT CAG TGT TCA GCT GAG GAG ATG AAC TTT GTG TTA
--- --- --- --- --- --- --- --- --- --- --- --- --- --- --- --- --- ---
 D   R   Y   V   E   V   F   Q   C   S   A   E   E   M   N   F   V   L 1577        1586        1595        1604        1613        1622
ATG GGG GGC ACT TTA AAT CGA AAT GGC TTA TCC CCA CCG CCA TGC CTG TCT CCT
--- --- --- --- --- --- --- --- --- --- --- --- --- --- --- --- --- ---
 M   G   G   T   L   N   R   N   G   L   S   P   P   P   C   L   S   P

1631        1640        1649        1658        1667        1676
CCC TCC TAC ACA TTT CCA GCT CCT GCT GCA GTT ATT CCT ACA GAA GCT GCC ATT
--- --- --- --- --- --- --- --- --- --- --- --- --- --- --- --- --- ---
P   S   Y   T   F   P   A   P   A   A   V   I   P   T   E   A   A   I 1685        1694        1703        1712        1721        1730
TAC CAG CCC TCT GTG ATT TTG AAT CCA CGA GCA CTG CAG CCC TCC ACA GCG TAC
--- --- --- --- --- --- --- --- --- --- --- --- --- --- --- --- --- ---
 Y   Q   P   S   V   I   L   N   P   R   A   L   Q   P   S   T   A   Y 1739        1748        1757        1766        1775        1784
TAC CCA GCA GGC ACT CAG CTC TTC ATG AAC TAC ACA GCG TAC TAT CCC AGC CCC
--- --- --- --- --- --- --- --- --- --- --- --- --- --- --- --- --- ---
 Y   P   A   G   T   Q   L   F   M   N   Y   T   A   Y   Y   P   S   P

1793        1802        1811        1820        1829        1838
CCA GGT TCG CCT AAT AGT CTT GGC TAC TTC CCT ACA GCT GCT AAT CTT AGC GGT
--- --- --- --- --- --- --- --- --- --- --- --- --- --- --- --- --- ---
P   G   S   P   N   S   L   G   Y   F   P   T   A   A   N   L   S   G

1847        1856        1865        1874        1883        1892
GTC CCT CCA CAG CCT GGC ACG GTG GTC AGA ATG CAG GGC CTG GCC TAC AAT ACT
--- --- --- --- --- --- --- --- --- --- --- --- --- --- --- --- --- ---
V   P   P   Q   P   G   T   V   V   R   M   Q   G   L   A   Y   N   T 1901        1910        1919        1928        1937        1946
GGA GTT AAG GAA ATT CTT AAC TTC TTC CAA GGT TAC CAG TAT GCA ACC GAG GAT
--- --- --- --- --- --- --- --- --- --- --- --- --- --- --- --- --- ---
 G   V   K   E   I   L   N   F   F   Q   G   Y   Q   Y   A   T   E   D 1955        1964        1973        1982        1991        2000
GGA CTT ATA CAC ACA AAT GAC CAG GCC AGG ACT CTA CCC AAA GAA TGG GTT TGT
--- --- --- --- --- --- --- --- --- --- --- --- --- --- --- --- --- ---
 G   L   I   H   T   N   D   Q   A   R   T   L   P   K   E   W   V   C 2009        2018        2027        2036        2045        2054
ATT TAA GGG CCC CAG CAG TTA GAA CAT CCT CAG AAA AGA AGT GTT TGA AAG ATG
--- --- --- --- --- --- --- --- --- --- --- --- --- --- --- --- --- ---
 I   *   G   P   Q   Q   L   E   H   P   Q   K   R   S   V   *   K   M 2063        2072        2081        2090        2099        2108
TAT GGT GAT CTT GAA ACC TCC AGA CAC AAG AAA ACT TCT AGC AAA TTC AGG GGA
```

FIG. 1-4

```
        ---  ---  ---  ---  ---  ---  ---  ---  ---  ---  ---  ---  ---  ---  ---  ---  ---  ---
         Y    G    D    L    E    T    S    R    H    K    K    T    S    S    K    F    R    G 2117           2126           2135           2144           2153           2162
        AGT  TTG  TCT  ACA  CTC  AGG  CTG  CAG  TAT  TTT  CAG  CAA  ACT  TGA  TTG  GAC  AAA  CGG
        ---  ---  ---  ---  ---  ---  ---  ---  ---  ---  ---  ---  ---  ---  ---  ---  ---  ---
         S    L    S    T    L    R    L    Q    Y    F    Q    Q    T    *

2171           2180           2189           2198           2207           2216
        GCC  TGT  GCC  TTA  TCT  TTT  GGT  GGA  GTG  AAA  AAA  TTT  GAG  CTA  GTG  AAG  CCA  AAT
        ---  ---  ---  ---  ---  ---  ---  ---  ---  ---  ---  ---  ---  ---  ---  ---  ---  ---
             2225           2234           2243           2252           2261           2270
        CGT  AAC  TTA  CAG  CAA  GCA  GCA  TGC  AGC  ATA  CCT  GGC  TCT  TTG  CTG  ATT  GCA  AAT
        ---  ---  ---  ---  ---  ---  ---  ---  ---  ---  ---  ---  ---  ---  ---  ---  ---  ---
             2279           2288           2297           2306           2315           2324
        AGG  CAT  TTA  AAA  TGT  GAA  TTT  GGA  ATC  AGA  TGT  CTC  CAT  TAC  TTC  CAG  TTA  AAG
        ---  ---  ---  ---  ---  ---  ---  ---  ---  ---  ---  ---  ---  ---  ---  ---  ---  ---
             2333           2342           2351           2360           2369           2378
        TGG  CAT  CAT  AGG  TGT  TTC  CTA  AGT  TTT  AAG  TCT  TGG  ATA  AAA  ACT  CCA  CCA  GTG
        ---  ---  ---  ---  ---  ---  ---  ---  ---  ---  ---  ---  ---  ---  ---  ---  ---  ---
             2387           2396           2405           2414           2423           2432
        TCT  ACC  ATC  TCC  ACC  ATG  AAC  TCT  GTT  AAG  GAA  GCT  TCA  TTT  TTG  TAT  ATT  CCC
        ---  ---  ---  ---  ---  ---  ---  ---  ---  ---  ---  ---  ---  ---  ---  ---  ---  ---
             2441           2450           2459           2468           2477           2486
        GCT  CTT  TTC  TCT  TCA  TTT  CCC  TGT  CTT  CTG  CAT  AAT  CAT  GCC  TTC  TTG  CTA  AGT
        ---  ---  ---  ---  ---  ---  ---  ---  ---  ---  ---  ---  ---  ---  ---  ---  ---  ---
             2495           2504           2513           2522           2531           2540
        AAT  TCA  AGC  ATA  AGA  TCT  TGG  AAT  AAT  AAA  ATC  ACA  ATC  TTA  GGA  GAA  AGA  ATA
        ---  ---  ---  ---  ---  ---  ---  ---  ---  ---  ---  ---  ---  ---  ---  ---  ---  ---
             2549           2558           2567           2576           2585           2594
        AAA  TTG  TTA  TTT  TCC  CAG  TCT  CTT  GGC  CAT  GAT  GAT  ATC  TTA  TGA  TTA  AAA  ACA
        ---  ---  ---  ---  ---  ---  ---  ---  ---  ---  ---  ---  ---  ---  ---  ---  ---  ---
             2603           2612           2621           2630           2639           2648
        AAT  TAA  ATT  TTA  AAA  CAC  CTG  AAG  ATA  AAT  TAG  AAG  AAA  TTG  TGC  ACC  CTC  CAC
        ---  ---  ---  ---  ---  ---  ---  ---  ---  ---  ---  ---  ---  ---  ---  ---  ---  ---
             2657           2666           2675           2684           2693           2702
        AAA  ACA  TAC  AAA  GTT  TAA  AAG  TTT  GGA  TCT  TTT  TCT  CAG  CAG  GTA  TCA  GTT  GTA
        ---  ---  ---  ---  ---  ---  ---  ---  ---  ---  ---  ---  ---  ---  ---  ---  ---  ---
             2711           2720           2729           2738           2747           2756
        AAT  AAT  GAA  TTA  GGG  GCC  AAA  ATG  CAA  AAC  GAA  AAA  TGA  AGC  AGC  TAC  ATG  TAG
        ---  ---  ---  ---  ---  ---  ---  ---  ---  ---  ---  ---  ---  ---  ---  ---  ---  ---
             2765           2774           2783           2792           2801           2810
        TTA  GTA  ATT  TCT  AGT  TTG  AAC  TGT  AAT  TGA  ATA  TTG  TGG  CTT  CAT  ATG  TAT  TAT
        ---  ---  ---  ---  ---  ---  ---  ---  ---  ---  ---  ---  ---  ---  ---  ---  ---  ---
             2819           2828           2837           2846           2855           2864
        TTT  ATA  TTG  TAC  TTT  TTT  CAT  TAT  TGA  TGG  TTT  GGA  CTT  TAA  TAA  GAG  AAA  TTC
        ---  ---  ---  ---  ---  ---  ---  ---  ---  ---  ---  ---  ---  ---  ---  ---  ---  ---
             2873           2882           2891           2900           2909           2918
        CAT  AGT  TTT  TAA  TAT  CCC  AGA  AGT  GAG  ACA  ATT  TGA  ACA  GTG  TAT  TCT  AGA  AAA
        ---  ---  ---  ---  ---  ---  ---  ---  ---  ---  ---  ---  ---  ---  ---  ---  ---  ---
             2927           2936           2945           2954           2963           2972
        CAA  TAC  ACT  AAC  TGA  ACA  GAA  GTG  AAT  GCT  TAT  ATA  TAT  TAT  GAT  AGC  CTT  AAA
        ---  ---  ---  ---  ---  ---  ---  ---  ---  ---  ---  ---  ---  ---  ---  ---  ---  ---
             2981           2990           2999           3008           3017           3026
        CCT  TTT  TCC  TCT  AAT  GCC  TTA  ACT  GTC  AAA  TAA  TTA  TAA  CCT  TTT  AAA  GCA  TAG
        ---  ---  ---  ---  ---  ---  ---  ---  ---  ---  ---  ---  ---  ---  ---  ---  ---  ---
             3035           3044           3053           3062           3071           3080
        GAC  TAT  AGT  CAG  CAT  GCT  AGA  CTG  AGA  GGT  AAA  CAC  TGA  TGC  AAT  TAG  AAC  AGG
        ---  ---  ---  ---  ---  ---  ---  ---  ---  ---  ---  ---  ---  ---  ---  ---  ---  ---
             3089           3098           3107           3116           3125           3134
        TAC  TGA  TGC  TGT  CAG  TGT  TTA  ACA  CTA  TGT  TTA  GCT  GTG  TTT  ATG  CTA  TAA  AAG
        ---  ---  ---  ---  ---  ---  ---  ---  ---  ---  ---  ---  ---  ---  ---  ---  ---  ---
             3143           3152           3161           3170           3179           3188
        TGC  AAT  ATT  AGA  CAC  TAG  CTA  GTA  CTG  CTG  CCT  CAT  GTA  ACT  CCA  AAG  AAA  ACA
```

FIG. 1-5

```
                3197          3206          3215          3224          3233          3242
            GGA TTT CAT TAA GTG CAT TGA ATG TGG ATA TTT CTC TAA GTT ACT CAT ATT GTC 3251          3260          3269          3278          3287          3296
            CTT TGC TTG AAT GCA ATG CCG TGC AGA TTT ATG AGG CTG CTA TTT TTA TTT TCT 3305          3314          3323          3332          3341          3350
            GTG CAT TAC TTT AAC ACC TTA AAG GGA GAA GCA AAC ATT TCC TTC TTC AGC TGA 3359          3368          3377          3386          3395          3404
            CTG GCA ATG GCC CTT TAA CTG CAA TAG GAA GAA AAA AAA AAA GGT TTG TGT GAA 3413          3422          3431          3440          3449          3458
            AAT TGG TGA TAA CTG GCA CTT AAG ATC GAA AAG AAA TTT CTG TAT ACT TGA TGC 3467          3476          3485          3494          3503          3512
            CTT AAG ATG CCC AAA GCT GCC CAA AGC TCT GAA AGA CTT TAA GAT AGG CAG TAA 3521          3530          3539          3548          3557          3566
            TGC TTA CTA CAA TAC TAC TGA GTT TTT GTA GAG TTA ACA TTT GAT AAT AAA ACT 3575          3584          3593
            TGC CTG TTT AAT CTC AAA AAA AAA AAA AAA AAA A 3'
```

Panels:

A
1. Brain
2. Prostate
3. LAPC-4 AD
4. LAPC-4 AI
5. LAPC-9 AD
6. HeLa
7. mouse mix
8. Neg. control

B
1. Brain
2. Heart
3. Kidney
4. Liver
5. Lung
6. Pancreas
7. Placenta
8. Skeletal Muscle

C
1. Colon
2. Ovary
3. Leukocytes
4. Prostate
5. Small Intestine
6. Spleen
7. Testis
8. Thymus

Expression of 20P2H8 in prostate and multiple cancer cell lines

1. Bladder cancer patient pool
2. Colon cancer patient pool
3. Lung cancer patient pool

Expression of 20P2H8 in Cancer Patient Tumors

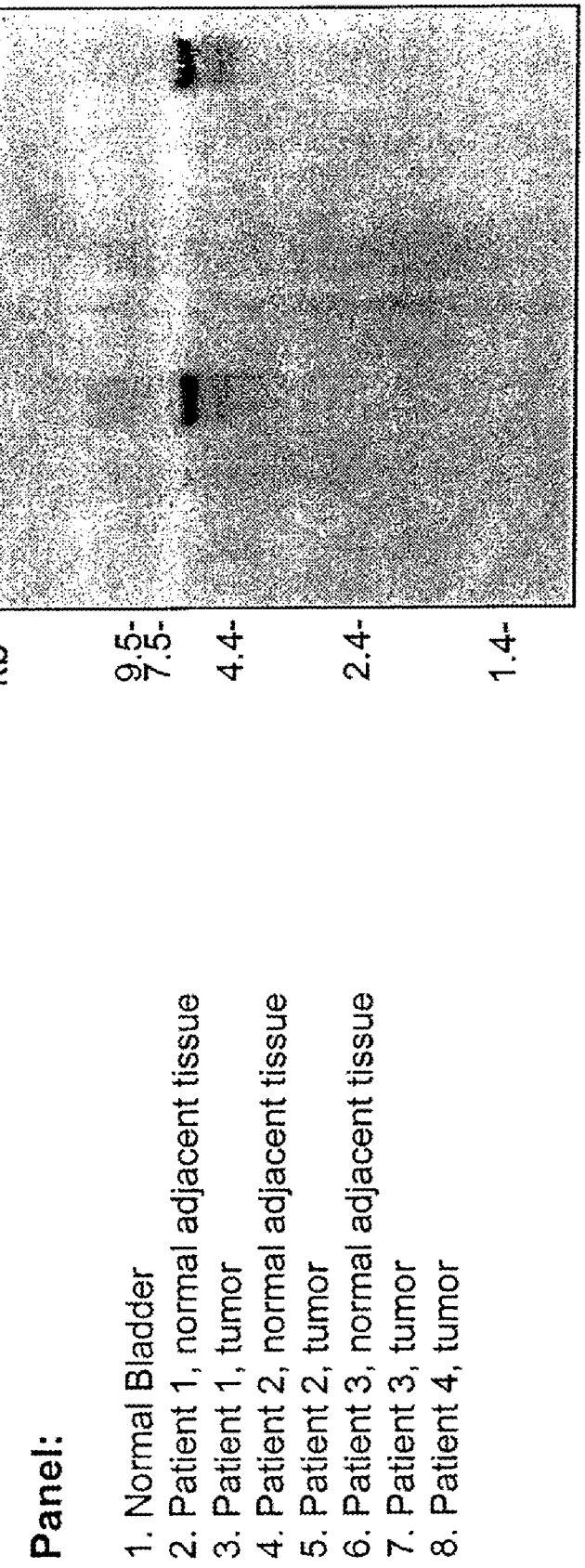
FIG. 8: Expression of 20P2H8 in Bladder Cancer Patients Samples
Panel:
1. Normal Bladder
2. Patient 1, normal adjacent tissue
3. Patient 1, tumor
4. Patient 2, normal adjacent tissue
5. Patient 2, tumor
6. Patient 3, normal adjacent tissue
7. Patient 3, tumor
8. Patient 4, tumor

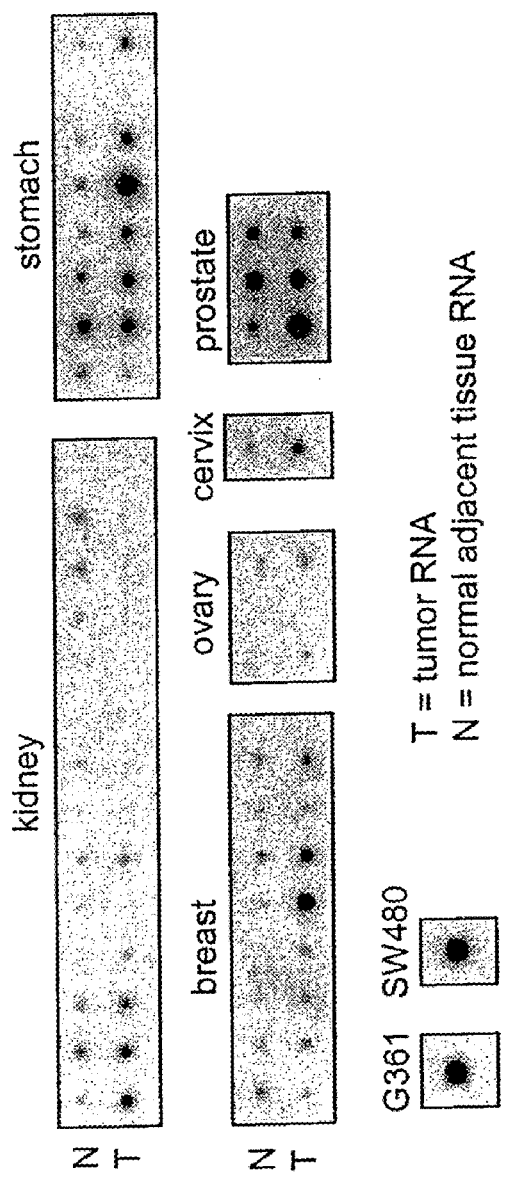
FIG. 9: Expression of 20P2H8 in Human Cancers and their Respective Normal Matched Tissues

GENE UPREGULATED IN CANCERS OF THE PROSTATE

This application is a continuation of U.S. patent application Ser. No. 10/959,697, filed Oct. 5, 2004, which is a continuation of U.S. patent application Ser. No. 09/697,206, filed Oct. 26, 2000, now U.S. Pat. No. 6,893,818, which claims the benefit of U.S. provisional patent application No. 60/162,364, filed Oct. 28, 1999. The contents of the above-referenced applications are incorporated herein by this reference in their entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 511582002102Seqlist.txt | July 8, 2008 | 12,616 bytes |

FIELD OF THE INVENTION

The invention described herein relates to a novel gene and its encoded protein, termed 20P2H8, and to diagnostic and therapeutic methods and compositions useful in the management of various cancers which express 20P2H8, particularly including cancers of the bladder, prostate, colon and pancreas.

BACKGROUND OF THE INVENTION

Cancer is the second leading cause of human death next to coronary disease. Worldwide, millions of people die from cancer every year. In the United States alone, cancer causes the death of well over a half-million people each year, with some 1.4 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Many cancer patients experience a recurrence.

Generally speaking, the fundamental problem in the management of the deadliest cancers is the lack of effective and non-toxic systemic therapies. Molecular medicine, still very much in its infancy, promises to redefine the ways in which these cancers are managed. Unquestionably, there is an intensive worldwide effort aimed at the development of novel molecular approaches to cancer diagnosis and treatment. For example, there is a great interest in identifying truly tumor-specific genes and proteins that could be used as diagnostic and prognostic markers and/or therapeutic targets or agents. Research efforts in these areas are encouraging, and the increasing availability of useful molecular technologies has accelerated the acquisition of meaningful knowledge about cancer. Nevertheless, progress is slow and generally uneven.

As discussed below, the management of prostate cancer serves as a good example of the limited extent to which molecular biology has translated into real progress in the clinic. With limited exceptions, the situation is more or less the same for the other major carcinomas mentioned above.

Worldwide, prostate cancer is the fourth most prevalent cancer in men. In North America and Northern Europe, it is by far the most common male cancer and is the second leading cause of cancer death in men. In the United States alone, well over 40,000 men die annually of this disease—second only to lung cancer. Despite the magnitude of these figures, there is still no effective treatment for metastatic prostate cancer. Surgical prostatectomy, radiation therapy, hormone ablation therapy, and chemotherapy remain fixed as the main treatment modalities. Unfortunately, these treatments are ineffective for many and are often associated with significant undesirable consequences.

On the diagnostic front, the lack of a prostate tumor marker that can accurately detect early-stage, localized tumors remains a significant limitation in the management of this disease. Although the serum PSA assay has been a very useful tool, its specificity and general utility is widely regarded as lacking in several important respects, as further discussed below. Most prostate cancers initially occur in the peripheral zone of the prostate gland, away from the urethra. Tumors within this zone may not produce any symptoms and, as a result, most men with early-stage prostate cancer will not present clinical symptoms of the disease until significant progression has occurred. Tumor progression into the transition zone of the prostate may lead to urethral obstruction, thus producing the first symptoms of the disease. However, these clinical symptoms are indistinguishable from the common non-malignant condition of benign prostatic hyperplasia (BPH). Early detection and diagnosis of prostate cancer currently relies on digital rectal examinations (DRE), prostate specific antigen (PSA) measurements, transrectal ultrasonography (TRUS), and transrectal needle biopsy (TRNB). At present, serum PSA measurement in combination with DRE represent the leading tool used to detect and diagnose prostate cancer. Both have major limitations which have fueled intensive research into finding better diagnostic markers of this disease.

Similarly, there is no available marker that can predict the emergence of the typically fatal metastatic stage of prostate cancer. Diagnosis of metastatic stage is presently achieved by open surgical or laparoscopic pelvic lymphadenectomy, whole body radionuclide scans, skeletal radiography, and/or bone lesion biopsy analysis. Clearly, better imaging and other less invasive diagnostic methods offer the promise of easing the difficulty those procedures place on a patient, as well as improving diagnostic accuracy and opening therapeutic options. A similar problem is the lack of an effective prognostic marker for determining which cancers are indolent and which ones are or will be aggressive. PSA, for example, fails to discriminate accurately between indolent and aggressive cancers. Until there are prostate tumor markers capable of reliably identifying early-stage disease, predicting susceptibility to metastasis, and precisely imaging tumors, the management of prostate cancer will continue to be extremely difficult.

PSA is the most widely used tumor marker for screening, diagnosis, and monitoring prostate cancer today. In particular, several immunoassays for the detection of serum PSA are in widespread clinical use. Recently, a reverse transcriptase-polymerase chain reaction (RT-PCR) assay for PSA mRNA in serum has been developed. However, PSA is not a disease-specific marker, as elevated levels of PSA are detectable in a large percentage of patients with BPH and prostatitis (25-86%) (Gao et al., 1997, Prostate 31: 264-281), as well as in other nonmalignant disorders and in some normal men, a factor which significantly limits the diagnostic specificity of this marker. For example, elevations in serum PSA of between 4 to 10 ng/ml are observed in BPH, and even higher values are observed in prostatitis, particularly acute prostatitis. BPH is an extremely common condition in men. Further confusing the situation is the fact that serum PSA elevations may be observed without any indication of disease from DRE, and visa-versa. Moreover, it is now recognized that PSA is not prostate-specific (Gao et al., supra, for review).

Various methods designed to improve the specificity of PSA-based detection have been described, such as measuring PSA density and the ratio of free vs. complexed PSA. However, none of these methodologies have been able to reproducibly distinguish benign from malignant prostate disease. In addition, PSA diagnostics have sensitivities of between 57-79% (Cupp & Osterling, 1993, Mayo Clin Proc 68:297-306), and thus miss identifying prostate cancer in a significant population of men with the disease.

There are some known markers which are expressed predominantly in prostate, such as prostate specific membrane antigen (PSM), a hydrolase with 85% identity to a rat neuropeptidase (Carter et al., 1996, Proc. Natl. Acad. Sci. USA 93: 749; Bzdega et al., 1997, J. Neurochem. 69: 2270). However, the expression of PSM in small intestine and brain (Israeli et al., 1994, Cancer Res. 54: 1807), as well its potential role in neuropeptide catabolism in brain, raises concern of potential neurotoxicity with anti-PSM therapies. Preliminary results using an Indium-111 labeled, anti-PSM monoclonal antibody to image recurrent prostate cancer show some promise (Sodee et al., 1996, Clin Nuc Med 21: 759-766). More recently identified prostate cancer markers include PCTA-1 (Su et al., 1996, Proc. Natl. Acad. Sci. USA 93: 7252) and prostate stem cell antigen (PSCA) (Reiter et al., 1998, Proc. Natl. Acad. Sci. USA 95: 1735). PCTA-1, a novel galectin, is largely secreted into the media of expressing cells and may hold promise as a diagnostic serum marker for prostate cancer (Su et al., 1996). PSCA, a GPI-linked cell surface molecule, was cloned from LAPC-4 cDNA and is unique in that it is expressed primarily in basal cells of normal prostate tissue and in cancer epithelia (Reiter et al., 1998). Vaccines for prostate cancer are also being actively explored with a variety of antigens, including PSM and PSA.

SUMMARY OF THE INVENTION

The present invention relates to the gene designated 20P2H8, which is over-expressed in cancers including cancer of the prostate. Northern blot expression analysis of 20P2H8 gene expression in normal tissues shows a predominant transcript of about 4.4 Kb that is highly expressed in pancreas, and is also expressed in prostate, colon and placenta. The predicted molecular weight of the 20P2H8 protein is 57.4 kD and its' pI is 7.7. In addition, expression analysis demonstrates high levels of 20P2H8 expression in several prostate and other cancer cell lines as well as prostate, bladder, kidney and breast cancer patient samples and tumor xenografts. The expression profile of 20P2H8 in normal adult tissues, combined with the over-expression observed in cancer cells such as pancreas, bladder, testis, lung, ovary and prostate cancer cell lines and/or cancer patient samples, provides evidence that 20P2H8 is aberrantly expressed in at least some cancers, and can serve as a useful diagnostic and/or therapeutic target for such cancers.

The invention provides polynucleotides corresponding or complementary to all or part of the 20P2H8 genes, mRNAs, and/or coding sequences, preferably in isolated form, including polynucleotides encoding 20P2H8 proteins and fragments thereof, DNA, RNA, DNA/RNA hybrid, and related molecules, polynucleotides or oligonucleotides complementary to the 20P2H8 genes or mRNA sequences or parts thereof, and polynucleotides or oligonucleotides that hybridize to the 20P2H8 genes, mRNAs, or to 20P2H8-encoding polynucleotides. Also provided are means for isolating cDNAs and the genes encoding 20P2H8. Recombinant DNA molecules containing 20P2H8 polynucleotides, cells transformed or transduced with such molecules, and host-vector systems for the expression of 20P2H8 gene products are also provided. The invention further provides 20P2H8 proteins and polypeptide fragments thereof. The invention further provides antibodies that bind to 20P2H8 proteins and polypeptide fragments thereof, including polyclonal and monoclonal antibodies, murine and other mammalian antibodies, chimeric antibodies, humanized and fully human antibodies, and antibodies labeled with a detectable marker.

The invention further provides methods for detecting the presence and status of 20P2H8 polynucleotides and proteins in various biological samples, as well as methods for identifying cells that express 20P2H8. A typical embodiment of this invention provides methods for monitoring 20P2H8 gene products in a tissue sample having or suspected of having some form of growth dysregulation such as cancer.

The invention further provides various therapeutic compositions and strategies for treating cancers that express 20P2H8 such as prostate cancers, including therapies aimed at inhibiting the transcription, translation, processing or function of 20P2H8 as well as cancer vaccines.

BRIEF DESCRIPTION OF THE FIGURES

FIG. 1 show the nucleotide (SEQ ID NO: 1) and deduced amino acid (SEQ ID NO: 2) sequences of 20P2H8 cDNA. The start methionine and putative Kozak sequence are indicated in bold, RNA-binding domains RNP1 and RNP2 (shaded) are boxed, 3 Proline-rich regions are in bold.

FIG. 8 shows a Northern analysis from tissues from patients with bladder cancer and unaffected individuals. Northern analysis was performed on bladder cancer and their adjacent normal matched tissues obtained from four bladder cancer patients. For this experiment, 10 µg of total RNA was loaded for each sample. Overexpression of 20P2H8 was seen in 3 out of 4 tumor samples tested. No expression was observed in any of the 3 normal matched tissues tested, nor in bladder isolated from a normal individual. The data demonstrate specific expression of 20P2H8 in cancer but not in normal bladder tissues.

FIG. 9 shows a RNA dot blot analysis from tissues from patients with various cancers. Expression of 20P2H8 was assayed in a panel of human cancers (T) and their respective matched normal tissues (N) on RNA dot blots. 20P2H8 overexpression was detected in 4 out of 14 kidney cancers, 7 out of 9 breast cancers 1 out of 3 prostate cancers, 2 out of 3 ovarian cancers, 1 out of 1 cervical cancer, and 4 out of 8 stomach cancers. 20P2H8 was also found to be highly expressed in the melanoma cell line G361 and the colorectal adenocarcinoma line SW480.

DETAILED DESCRIPTION OF THE INVENTION

Figure 2:
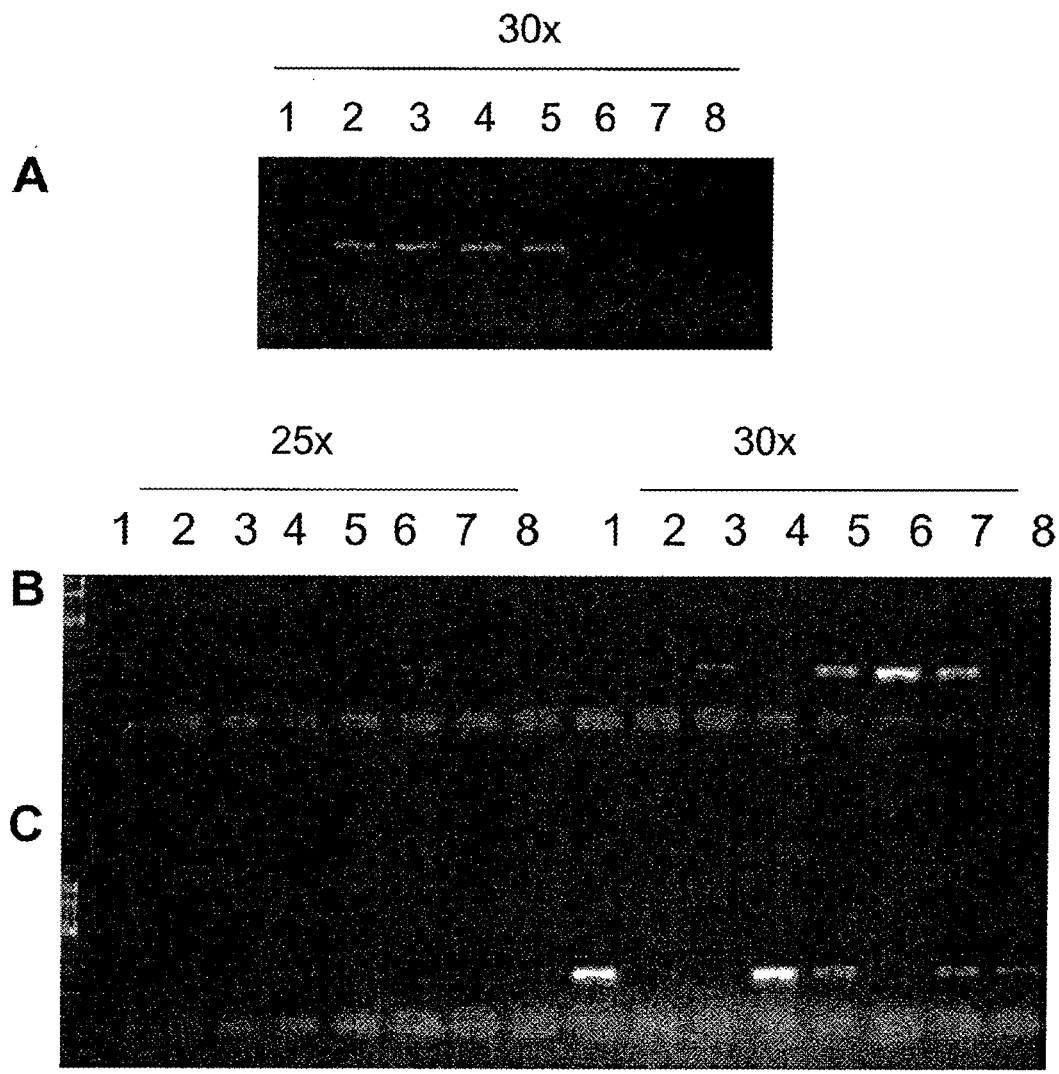
FIGS. 2A-2C show a semi-quantitative RT-PCR analysis of 20P2H8 gene expression in a panel of 16 normal human tissues (Panels B and C) and several prostate cancer xenografts (Panel A). Lanes 1-8 in panel A correspond to RT-PCR analysis of 20P2H8 gene expression in brain, prostate, LAPC-4 AD, LAPC-4 AI, LAPC-9 AD, HeLa, mouse mix and a negative control respectively. Lanes 1-8 in panel B correspond to RT-PCR analysis of 20P2H8 gene expression in brain, heart, kidney, liver, lung, pancreas, placenta and skeletal muscle respectively. Lanes 1-8 in panel C correspond to RT-PCR analysis of 20P2H8 gene expression in colon, ovary, leukocytes, prostate, small intestine, spleen, testis and thymus respectively.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

As used herein, the terms "advanced prostate cancer", "locally advanced prostate cancer", "advanced disease" and "locally advanced disease" mean prostate cancers which have extended through the prostate capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

As used herein, the terms "metastatic prostate cancer" and "metastatic disease" mean prostate cancers which have spread to regional lymph nodes or to distant sites, and are meant to include stage D disease under the AUA system and stage TxNxM+ under the TNM system. As is the case with locally advanced prostate cancer, surgery is generally not indicated for patients with metastatic disease, and hormonal (androgen ablation) therapy is the preferred treatment modality. Patients with metastatic prostate cancer eventually develop an androgen-refractory state within 12 to 18 months of treatment initiation, and approximately half of these patients die within 6 months thereafter. The most common site for prostate cancer metastasis is bone. Prostate cancer bone metastases are, on balance, characteristically osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

As used herein, the term "polynucleotide" means a polymeric form of nucleotides of at least about 10 bases or base pairs in length, either ribonucleotides or deoxynucleotides or a modified form of either type of nucleotide, and is meant to include single and double stranded forms of DNA.

As used herein, the term "polypeptide" means a polymer of at least about 6 amino acids. Throughout the specification, standard three letter or single letter designations for amino acids are used.

As used herein, the terms "hybridize", "hybridizing", "hybridizes" and the like, used in the context of polynucleotides, are meant to refer to conventional hybridization conditions, preferably such as hybridization in 50% formamide/6×SSC/0.1% SDS/100 μg/ml ssDNA, in which temperatures for hybridization are above 37 degrees C. and temperatures for washing in 0.1×SSC/0.1% SDS are above 55 degrees C., and most preferably to stringent hybridization conditions.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., 1989, Molecular Cloning: A Laboratory Manual, New York: Cold Spring Harbor Press, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

In the context of amino acid sequence comparisons, the term "identity" is used to express the percentage of amino acid residues at the same relative positions that are the same. Also in this context, the term "homology" is used to express the percentage of amino acid residues at the same relative positions that are either identical or are similar, using the conserved amino acid criteria of BLAST analysis, as is generally understood in the art. For example, % identity values may be generated by WU-BLAST-2 (Altschul et al., 1996, Methods in Enzymology 266:460-480; http://blast.wustl/edu/blast/README.html). Further details regarding amino acid substitutions, which are considered conservative under such criteria, are provided below. Additional definitions are provided throughout the subsections that follow.

As discussed in detail below, the present invention relates to a novel protein designated 20P2H8 which shares homology with several heterogenous nuclear ribonucleoproteins (hnRNPs). A full length approximately 3600 bp 20P2H8 cDNA (SEQ ID NO: 1), encoding a 517 amino acid open reading frame (SEQ ID NO: 2), is provided herein. The predicted 20P2H8 protein exhibits five RNA binding sequences, two of which correspond to ribonucleoprotein-1 (RNP1) consensus sites, and three of which correspond to RNP2 sites. In addition, 20P2H8 contains three regions with significant proline content (30-42%), which lie outside regions of homology with hnRNPs. These proline rich regions may be involved in protein-protein interactions as has been observed in other proteins (Schlessenger et al., 1994, Curr. Opin. Genet. Dev. 4: 25). The 20P2H8 protein structure shows highest homology with a protein identified in *C. elegans* (Genbank CAA92704), and significant homology is also seen with various hnRNPs involved in mRNA splicing (ROF, ROH1 and ROH2; Honore et al., 1995, J. Biol. Chem. 270: 28780). Accordingly, based on these structural features and homologies, it is likely that the 20P2H8 protein is involved in RNA splicing.

Expression analysis by northern blot shows highest expression levels of a single 4.4 kb 20P2H8 transcript in pancreas, and is also expressed in prostate, colon and placenta. No other normal tissues in this panel show detectable expression. Expression of 20P2H8 is up-regulated in human prostate tumor xenografts derived from metastatic prostate cancer (compared to normal prostate). Further, analysis of 20P2H8 expression in multiple cancer cell lines reveals high levels of expression in several pancreatic (BxPC-3, HPAC, Capan-1) and colon (CaCo-2, T84, Colo-205) cancer cell lines. The up-regulated expression of 20P2H8 in cancers including cancers of the bladder, kidney, prostate, pancreas and colon indicates that the 20P2H8 gene, message and protein allows 20P2H8 to be used as a diagnostic, staging and/or prognostic marker for cancers of the prostate, colon and pancreas, and/or may also serve as a target for various approaches to the treatment of these cancers.

The invention provides polynucleotides corresponding or complementary to all or part of the 20P2H8 genes, mRNAs, and/or coding sequences, preferably in isolated form, including polynucleotides encoding 20P2H8 proteins and fragments thereof, DNA, RNA, DNA/RNA hybrid, and related molecules, polynucleotides or oligonucleotides complementary to the 20P2H8 genes or mRNA sequences or parts thereof, and polynucleotides or oligonucleotides which hybridize to the 20P2H8 genes, mRNAs, or to 20P2H8-encoding polynucleotides. Also provided are means for isolating cDNAs and the genes encoding 20P2H8. Recombinant DNA molecules containing 20P2H8 polynucleotides, cells transformed or transduced with such molecules, and host-vector systems for the expression of 20P2H8 gene products are also provided. The invention further provides 20P2H8 proteins and polypeptide fragments thereof. The invention further provides antibodies that bind to 20P2H8 proteins and polypeptide fragments thereof, including polyclonal and monoclonal antibodies, murine and other mammalian antibodies, chimeric antibodies, humanized and fully human antibodies, antibodies labeled with a detectable marker, and antibodies conjugated to radionuclides, toxins or other therapeutic compositions. The invention further provides methods for detecting the presence of 20P2H8 polynucleotides and proteins in various biological samples, as well as methods for identifying cells that express a 20P2H8. The invention further provides various therapeutic compositions and strategies for treating cancers which express 20P2H8 such as prostate and bladder cancers, including antibody, vaccine and small molecule therapy, and therapies aimed at inhibiting the transcription, translation, processing or function of 20P2H8.

Molecular Biology of 20P2H8

As is further described in the Examples that follow, the 20P2H8 gene and protein have been characterized using a number of analytical approaches. For example, analyses of nucleotide coding and amino acid sequences were conducted in order to identify potentially related molecules, as well as recognizable structural domains, topological features, and other elements within the 20P2H8 mRNA and protein structure. Northern blot analyses of 20P2H8 mRNA expression were conducted in order to establish the range of normal and cancerous tissues expressing 20P2H8 message.

The isolated 20P2H8 cDNA (SEQ ID NO: 1) provided herein (FIG. 1) and corresponding gene are predicted to encode a 517 amino acid protein (SEQ ID NO: 2) with various structural features common to heterogenous nuclear ribonucleoproteins (hnRNPs) involved in RNA splicing, including five RNA binding sequences (two corresponding to ribonucleoprotein-1 (RNP1) and 3 corresponding to ribonucleoprotein-2 (RNP2). The protein exhibits significant homology to a *C. elegans* protein, designated CAA92704 (approximately 52.4% identity in a 311 residues overlap beginning with 20P2H8 amino acid residue 63 as shown in FIG. 1), as well as several hnRNPs involved in RNA splicing (e.g., ROF, ROH1 and ROH; Honore et al., 1995, J. Biol. Chem. 270: 28780). In addition, the 20P2H8 protein contains three regions with significant proline content (30-42%), which lie outside its regions of homology with hnRNPs. These proline rich regions may be involved in protein-protein interactions as has been observed in other proteins (Schlessenger et al., 1994, Curr. Opin. Genet. Dev. 4: 25).

The 20P2H8 gene is normally expressed predominantly in pancreas, with lower levels of expression occurring in prostate, colon and placenta (FIGS. 2 and 3), but is also expressed or over-expressed in a number of human cancers, including cancers of the prostate, kidney, skin, stomach, cervix, bladder, testis, ovaries, breast, pancreas, colon and lung (see e.g. FIGS. 4-8).

20P2H8 overexpression in the prostate cancer xenografts as well as kidney, stomach, breast and is an indication that this molecule is deregulated in prostate cancer. Therefore, 20P2H8 target for prostate cancer diagnosis and therapy. For example, interfering with 20P2H8 function, using an antibody and/or a small molecule, in prostate cancer cells may prevent de-differentiation and/or proliferation of cells. In addition, small molecules and/or specific antibodies may interfere with 20P2H8 function making this molecule a candidate for vaccine methodologies. Investigating 20P2H8 function may also lead to identification of other potential targets.

20P2H8 function can be assessed in mammalian cells using a variety of techniques that are well known in the art. For mammalian expression, 20P2H8 can be cloned into several vectors, including pcDNA 3.1 myc-His-tag (Invitrogen) and the retroviral vector pSRαtkneo (Muller et al., 1991, MCB 11:1785). Using these expression vectors, 20P2H8 can be expressed in several cell lines, including PC-3, NIH 3T3, LNCaP and 293T. Expression of 20P2H8 can be monitored using northern blot analysis.

The mammalian cell lines expressing 20P2H8 can be tested in several in vitro and in vivo assays, including cell proliferation in tissue culture, activation of apoptotic signals, tumor formation in SCID mice, and in vitro invasion using a membrane invasion culture system (MICS) (Welch et al., Int. J. Cancer 43: 449-457). The 20P2H8 cell phenotype can be compared to the phenotype of cells that lack expression of 20P2H8.

As disclosed herein, 20P2H8 exhibits specific properties that are analogous to those found in a family of genes whose polynucleotides, polypeptides and anti-polypeptide antibodies are used in well known diagnostic assays directed to examining conditions associated with dysregulated cell growth such as cancer, in particular prostate cancer (see e.g. both its highly specific pattern of tissue expression as well as its overexpression in prostate cancers as described for example in Example 3). The best known member of this class is PSA, the archetypal marker that has been used by medical practitioners for years to identify and monitor the presence of prostate cancer (see e.g. Merrill et al., J. Urol. 163 (2): 503-5120 (2000); Polascik et al., J. Urol. August; 162 (2):293-306 (1999) and Fortier et al., J. Nat. Cancer Inst. 91 (19): 1635-1640 (1999)). A variety of other diagnostic markers are also used in this context including p53 and K-ras (see e.g. Tulchinsky et al., Int J Mol Med 1999 July; 4 (1):99-102 and Minimoto et al., Cancer Detect Prev 2000; 24 (1): 1-12). Consequently, this disclosure of the 20P2H8 polynucleotides and polypeptides (as well as the 20P2H8 polynucleotide probes and anti-20P2H8 antibodies used to identify the presence of these molecules) and their properties allows skilled artisans to utilize these molecules in methods that are analogous to those used, for example, in a variety of diagnostic assays directed to examining conditions associated with cancer.

Typical embodiments of diagnostic methods which utilize the 20P2H8 polynucleotides, polypeptides and antibodies described herein are analogous to those methods from well established diagnostic assays which employ PSA polynucleotides, polypeptides and antibodies. For example, just as PSA polynucleotides are used as probes (for example in Northern analysis, see e.g. Sharief et al., Biochem. Mol. Biol. Int. 33 (3):567-74 (1994)) and primers (for example in PCR analysis, see e.g. Okegawa et al., J. Urol. 163 (4): 1189-1190 (2000)) to observe the presence and/or the level of PSA mRNAs in methods of monitoring PSA overexpression or the metastasis of prostate cancers, the 20P2H8 polynucleotides described herein can be utilized in the same way to detect 20P2H8 overexpression or the metastasis of prostate and other cancers expressing this gene. Alternatively, just as PSA polypeptides are used to generate antibodies specific for PSA which can then be used to observe the presence and/or the level of PSA proteins in methods of monitoring PSA protein overexpression (see e.g. Stephan et al., Urology 55 (4):560-3 (2000)) or the metastasis of prostate cells (see e.g. Alanen et al., Pathol. Res. Pract. 192 (3):233-7 (1996)), the 20P2H8 polypeptides described herein can be utilized to generate antibodies for use in detecting 20P2H8 overexpression or the metastasis of prostate cells and cells of other cancers expressing this gene.

Specifically, because metastases involves the movement of cancer cells from an organ of origin (such as the bladder, kidney or prostate gland etc.) to a different area of the body (such as a lymph node), assays which examine a biological sample for the presence of cells expressing 20P2H8 polynucleotides and/or polypeptides can be used to provide evidence of metastasis, for example, when a biological sample from tissue that does not normally contain 20P2H8 expressing cells (lymph node) is found to contain 20P2H8 expressing cells such as the 20P2H8 expression seen in LAPC4 and LAPC9, xenografts isolated from lymph node and bone metastasis respectively. Alternatively 20P2H8 polynucleotides and/or polypeptides can be used to provide evidence of cancer, for example, when a cells in biological sample that do not normally express 20P2H8 or express 20P2H8 at a different level (such as kidney, bladder, lung and prostate cells etc.) are found to express 20P2H8 or have an increased expression of 20P2H8. In such assays, artisans may further wish to generate supplementary evidence of metastasis by testing the biological sample for the presence of a second tissue restricted marker (in addition to 20P2H8) such as PSA, PSCA etc. (see e.g. Alanen et al., Pathol. Res. Pract. 192 (3): 233-237 (1996)).

Just as PSA polynucleotide fragments and polynucleotide variants are employed by skilled artisans for use in methods of monitoring this molecule, 20P2H8 polynucleotide fragments and polynucleotide variants can also be used in an analogous manner. In particular, typical PSA polynucleotides used in methods of monitoring this molecule are probes or primers which consist of fragments of the PSA cDNA sequence. Illustrating this, primers used to PCR amplify a PSA polynucleotide must include less than the whole PSA sequence to function in the polymerase chain reaction. In the context of such PCR reactions, skilled artisans generally create a variety of different polynucleotide fragments that can be used as primers in order to amplify different portions of a polynucleotide of interest or to optimize amplification reactions (see e.g. Caetano-Anolles, G. Biotechniques 25 (3): 472-476, 478-480 (1998); Robertson et al., Methods Mol. Biol. 98:121-154 (1998)). An additional illustration of the utility of such fragments is provided in Example 3, where a 20P2H8 polynucleotide fragment is used as a probe to show the overexpression of 20P2H8 mRNAs in cancer cells. In addition, in order to facilitate their use by medical practitioners, variant polynucleotide sequences are typically used as primers and probes for the corresponding mRNAs in PCR and Northern analyses (see e.g. Sawai et al., Fetal Diagn. Ther. 1996 November-December; 11 (6):407-13 and Current Protocols In Molecular Biology, Volume 2, Unit 2, Frederick M. Ausubul et al. eds., 1995)). Polynucleotide fragments and variants are typically useful in this context as long as they have the common attribute or characteristic of being capable of binding to a target polynucleotide sequence (e.g. the 20P2H8 polynucleotide shown in SEQ ID NO: 1) under conditions of high stringency.

Just as PSA polypeptide fragments and polypeptide variants are employed by skilled artisans for use in methods of monitoring this molecule, 20P2H8 polypeptide fragments and polypeptide variants can also be used in an analogous manner. In particular, typical PSA polypeptides used in methods of monitoring this molecule are fragments of the PSA protein which contain an epitope that can be recognized by an antibody which will specifically bind to the PSA protein. This practice of using polypeptide fragments or polypeptide variants used to generate antibodies (such as anti-PSA antibodies) is typical in the art with a wide variety of systems such as fusion proteins being used by practitioners (see e.g. Current Protocols In Molecular Biology, Volume 2, Unit 16, Frederick M. Ausubul et al. eds., 1995). In this context, each of the variety of epitopes in a protein of interest functions to provide the architecture upon which the antibody is generated. Typically, skilled artisans generally create a variety of different polypeptide fragments that can be used in order to generate antibodies specific for different portions of a polypeptide of interest (see e.g. U.S. Pat. No. 5,840,501 and U.S. Pat. No. 5,939,533). For example it may be preferable to utilize a polypeptide comprising one of the 20P2H8 biological motifs discussed below. Polypeptide fragments and variants are typically useful in this context as long as they have the common attribute or characteristic of having an epitope capable of generating an antibody specific for a target polypeptide sequence (e.g. the 20P2H8 polypeptide shown in SEQ ID NO: 2).

As shown herein, the 20P2H8 polynucleotides and polypeptides (as well as the 20P2H8 polynucleotide probes and anti-20P2H8 antibodies used to identify the presence of these molecules) exhibit specific properties that make them useful in diagnosing cancers of the prostate. The described diagnostic assays that measures the presence of 20P2H8 gene products, in order to evaluate the presence or onset of the particular disease conditions described herein such as prostate cancer are particularly useful in identifying potential candidates for preventive measures or further monitoring, as has been done so successfully with PSA. Moreover, these materials satisfy a need in the art for molecules having similar characteristics to PSA in situations where, for example, a definite diagnosis of metastasis of prostatic origin cannot be made on the basis of a testing for PSA alone (see e.g. Alanen et al., Pathol. Res. Pract. 192 (3): 233-237 (1996)), and consequently, materials such as 20P2H8 polynucleotides and polypeptides (as well as the 20P2H8 polynucleotide probes and anti-20P2H8 antibodies used to identify the presence of these molecules) must be employed to confirm metastases of prostatic origin.

Finally, in addition to their use in diagnostic assays, the 20P2H8 polynucleotides disclosed herein have a number of other specific utilities such as their use in the identification of oncogenetic associated chromosomal abnormalities in 15q22. Moreover, in addition to their use in diagnostic assays, the 20P2H8 polypeptides and polynucleotides disclosed herein have other utilities such as their use in the forensic analysis of tissues of unknown origin (see e.g. Takahama K Forensic Sci Int 1996 Jun. 28; 80 (1-2): 63-9).

20P2H8 Polynucleotides

One aspect of the invention provides polynucleotides corresponding or complementary to all or part of a 20P2H8 gene, mRNA, and/or coding sequence, preferably in isolated form, including polynucleotides encoding a 20P2H8 protein and fragments thereof, DNA, RNA, DNA/RNA hybrid, and related molecules, polynucleotides or oligonucleotides complementary to a 20P2H8 gene or mRNA sequence or a part thereof, and polynucleotides or oligonucleotides that hybridize to a 20P2H8 gene, mRNA, or to a 20P2H8 encoding polynucleotide (collectively, "20P2H8 polynucleotides"). As used herein, the 20P2H8 gene and protein is meant to include the 20P2H8 genes and proteins specifically described herein and the genes and proteins corresponding to other 20P2H8 proteins and structurally similar variants of the foregoing. Such other 20P2H8 proteins and variants will generally have coding sequences that are highly homologous to the 20P2H8 coding sequence, and preferably will share at least about 50% amino acid identity and at least about 60% amino acid homology (using BLAST criteria), more preferably sharing 70% or greater homology (using BLAST criteria).

A 20P2H8 polynucleotide may comprise a polynucleotide having the nucleotide sequence of human 20P2H8 as shown in FIG. 1, wherein T can also be U; a polynucleotide which encodes all or part of the 20P2H8 protein; a sequence complementary to the foregoing; or a polynucleotide fragment of any of the foregoing. Another embodiment comprises a polynucleotide encoding a 20P2H8 polypeptide whose sequence is encoded by the cDNA contained in the plasmid as deposited with American Type Culture Collection 10801 University Boulevard, Manassas, Va., USA (ATCC) as Accession No. 207151. Another embodiment comprises a polynucleotide which is capable of hybridizing under stringent hybridization conditions to the human 20P2H8 cDNA shown in FIG. 1.

Typical embodiments of the invention disclosed herein include 20P2H8 polynucleotides containing specific portions of the 20P2H8 mRNA sequence (and those which are complementary to such sequences) such as those that encode the protein and fragments thereof. For example, representative embodiments of the invention disclosed herein include: polynucleotides encoding about amino acid 1 to about amino acid 10 of the 20P2H8 protein shown in SEQ ID NO: 2, polynucleotides encoding about amino acid 20 to about amino acid 30 of the 20P2H8 protein shown in SEQ ID NO: 2, polynucleotides encoding about amino acid 30 to about amino acid 40 of the 20P2H8 protein shown in SEQ ID NO: 2, polynucleotides encoding about amino acid 40 to about amino acid 50 of the 20P2H8 protein shown in SEQ ID NO: 2, polynucleotides encoding about amino acid 50 to about amino acid 60 of the 20P2H8 protein shown in SEQ ID NO: 2, polynucleotides encoding about amino acid 60 to about amino acid 70 of the 20P2H8 protein shown in SEQ ID NO: 2, polynucleotides encoding about amino acid 70 to about amino acid 80 of the 20P2H8 protein shown in SEQ ID NO: 2, polynucleotides encoding about amino acid 80 to about amino acid 90 of the 20P2H8 protein shown in SEQ ID NO: 2 and polynucleotides encoding about amino acid 90 to about amino acid 100 of the 20P2H8 protein shown in SEQ ID NO: 2, etc. Following this scheme, polynucleotides encoding portions of the amino acid sequence of amino acids 100-517 of the 20P2H8 protein (SEQ ID NO: 2) are typical embodiments of the invention. Polynucleotides encoding larger portions of the 20P2H8 protein are also contemplated. For example polynucleotides encoding from about amino acid 1 (or 20 or 30 or 40 etc.) to about amino acid 20, (or 30, or 40 or 50 etc.) of the 20P2H8 protein shown in SEQ ID NO: 2 may be generated by a variety of techniques well known in the art.

Additional illustrative embodiments of 20P2H8 polynucleotides include embodiments consisting of a polynucleotide having the sequence as shown in FIG. 1 (SEQ ID NO: 1) from about nucleotide residue number 1 through about nucleotide residue number 500, from about nucleotide residue number 500 through about nucleotide residue number 1000 and from about nucleotide residue number 1000 through about nucleotide residue number 3600. These polynucleotide fragments can include any portion of the 20P2H8 sequence as shown in FIG. 1 (SEQ ID NO: 1), for example a polynucleotide having the 517 amino acid ORF within the polynucleotide sequence as shown in FIG. 1 (SEQ ID NO: 1), e.g. from about nucleotide residue number 450 through about nucleotide residue number 2000. Alternatively, a polynucleotide may include portions of both the coding and non-coding regions of the 20P2H8 protein such as a polynucleotide fragment consisting of the sequence from about residue 600 through about residue 3600 etc.

Additional illustrative embodiments of the invention disclosed herein include 20P2H8 polynucleotide fragments encoding one or more of the biological motifs contained within the 20P2H8 protein sequence. Typical polynucleotide fragments of the invention include those that encode one or more of the 20P2H8 N-glycosylation sites, casein kinase II phosphorylation sites, the RNA binding sequences such as the ribonucleoprotein-1 and ribonucleoprotein-2 consensus sites, the proline rich regions or N-myristoylation sites as disclosed in greater detail in the text discussing the 20P2H8 protein and polypeptides below.

The polynucleotides of the preceding paragraphs have a number of different specific uses. For example, because the human 20P2H8 gene maps to chromosome 15q22.32-23, polynucleotides encoding different regions of the 20P2H8 protein can be used to characterize cytogenetic abnormalities on chromosome 15, bands q13.2-q14 that have been identified as being associated with various cancers. In particular, a variety of chromosomal abnormalities in 15q22.32-23 have been identified as frequent cytogenetic abnormalities in a number of different cancers (see, e.g., Goffman et al., Cancer Genet. Cytogenet. 1983 8 (3): 197-202; Yeatment et al., Clin. Exp. Metastasis 1996 14 (3): 246-252)). Consequently, polynucleotides encoding specific regions of the 20P2H8 protein provide new tools that can be used to delineate with a greater precision than previously possible, the specific nature of the cytogenetic abnormalities in this region of chromosome 15 that may contribute to the malignant phenotype. In this context, these polynucleotides satisfy a need in the art for expanding the sensitivity of chromosomal screening in order to identify more subtle and less common chromosomal abnormalities (see, e.g., Evans et al., 1994, Am. J. Obstet. Gynecol. 171 (4):1055-1057).

Alternatively, as 20P2H8 is shown to be highly expressed in prostate cancers (see e.g. FIG. 2), these polynucleotides may be used in methods assessing the status of 20P2H8 gene products in normal versus cancerous tissues. Typically, polynucleotides encoding specific regions of the 20P2H8 protein may be used to assess the presence of perturbations (such as deletions, insertions, point mutations etc.) in specific regions (such as regions containing the RNA binding sequences) of the 20P2H8 gene products. Exemplary assays include both RT-PCR assays as well as single-strand conformation polymorphism (SSCP) analysis (see, e.g., Marrogi et al., 1999, J. Cutan. Pathol. 26 (8): 369-378), both of which utilize polynucleotides encoding specific regions of a protein to examine these regions within the protein.

Other specifically contemplated embodiments of the invention disclosed herein are genomic DNA, cDNAs, ribozymes, and antisense molecules, as well as nucleic acid molecules based on an alternative backbone or including alternative bases, whether derived from natural sources or synthesized. For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the 20P2H8 polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., 20P2H8. See for example, Jack Cohen, 1988, OLIGODEOXYNUCLEOTIDES, Antisense Inhibitors of Gene Expression, CRC Press; and Synthesis 1:1-5 (1988). The 20P2H8 antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention may be prepared by treatment of the corresponding O-oligos with 3H-1,2-benzodithiol-3-one-1,1-dioxide, which is a sulfur transfer reagent. See Iyer, R. P. et al, 1990, J. Org. Chem. 55:4693-4698; and Iyer, R. P. et al., 1990, J. Am. Chem. Soc. 112:1253-1254, the disclosures of which are fully incorporated by reference herein. Additional 20P2H8 antisense oligonucleotides of the present invention include morpholino antisense oligonucleotides known in the art (see e.g. Partridge et al., 1996, Antisense & Nucleic Acid Drug Development 6: 169-175).

The 20P2H8 antisense oligonucleotides of the present invention typically may be RNA or DNA that is complementary to and stably hybridizes with the first 100 N-terminal codons or last 100 C-terminal codons of the 20P2H8 genomic sequence or the corresponding mRNA. While absolute complementarity is not required, high degrees of complementarity are preferred. Use of an oligonucleotide complementary to this region allows for the selective hybridization to 20P2H8 mRNA and not to mRNA specifying other regulatory subunits of protein kinase. Preferably, the 20P2H8 antisense oligonucleotides of the present invention are a 15 to 30-mer fragment of the antisense DNA molecule having a sequence that hybridizes to 20P2H8 mRNA. Optionally, 20P2H8 antisense oligonucleotide is a 30-mer oligonucleotide that is complementary to a region in the first 10 N-terminal codons and last 10 C-terminal codons of 20P2H8. Alternatively, the antisense molecules are modified to employ ribozymes in the inhibition of 20P2H8 expression (L. A. Couture & D. T. Stinchcomb, 1996, Trends Genet. 12: 510-515).

Further specific embodiments of this aspect of the invention include primers and primer pairs, which allow the specific amplification of the polynucleotides of the invention or of any specific parts thereof, and probes that selectively or specifically hybridize to nucleic acid molecules of the invention or to any part thereof. Probes may be labeled with a detectable marker, such as, for example, a radioisotope, fluorescent compound, bioluminescent compound, a chemiluminescent compound, metal chelator or enzyme. Such probes and primers can be used to detect the presence of a 20P2H8 polynucleotide in a sample and as a means for detecting a cell expressing a 20P2H8 protein.

Examples of such probes include polypeptides comprising all or part of the human 20P2H8 cDNA sequences shown in SEQ ID NO: 1. Examples of primer pairs capable of specifically amplifying 20P2H8 mRNAs are also described in the Examples that follow. As will be understood by the skilled artisan, a great many different primers and probes may be prepared based on the sequences provided herein and used effectively to amplify and/or detect a 20P2H8 mRNA.

As used herein, a polynucleotide is said to be "isolated" when it is substantially separated from contaminant polynucleotides that correspond or are complementary to genes other than the 20P2H8 gene or that encode polypeptides other than 20P2H8 gene product or fragments thereof. A skilled artisan can readily employ nucleic acid isolation procedures to obtain an isolated 20P2H8 polynucleotide.

The 20P2H8 polynucleotides of the invention are useful for a variety of purposes, including but not limited to their use as probes and primers for the amplification and/or detection of the 20P2H8 gene(s), mRNA(s), or fragments thereof; as reagents for the diagnosis and/or prognosis of prostate cancer and other cancers; as coding sequences capable of directing the expression of 20P2H8 polypeptides; as tools for modulating or inhibiting the expression of the 20P2H8 gene(s) and/or translation of the 20P2H8 transcript(s); and as therapeutic agents.

Isolation of 20P2H8-Encoding Nucleic Acid Molecules

The 20P2H8 cDNA sequences described herein enable the isolation of other polynucleotides encoding 20P2H8 gene product(s), as well as the isolation of polynucleotides encoding 20P2H8 gene product homologs, alternatively spliced isoforms, allelic variants, and mutant forms of the 20P2H8 gene product. Various molecular cloning methods that can be employed to isolate full length cDNAs encoding a 20P2H8 gene are well known (See, e.g., Sambrook, J. et al., 1989, Molecular Cloning: A Laboratory Manual, 2d ed., Cold Spring Harbor Press, New York; Ausubel et al., eds., 1995, Current Protocols in Molecular Biology, Wiley and Sons). For example, lambda phage cloning methodologies may be conveniently employed, using commercially available cloning systems (e.g., Lambda ZAP Express, Stratagene). Phage clones containing 20P2H8 gene cDNAs may be identified by probing with a labeled 20P2H8 cDNA or a fragment thereof. For example, in one embodiment, the 20P2H8 cDNA (SEQ ID NO: 1) or a portion thereof can be synthesized and used as a probe to retrieve overlapping and full length cDNAs corresponding to a 20P2H8 gene. The 20P2H8 gene itself may be isolated by screening genomic DNA libraries, bacterial artificial chromosome libraries (BACs), yeast artificial chromosome libraries (YACs), and the like, with 20P2H8 DNA probes or primers.

Recombinant DNA Molecules and Host-Vector Systems

The invention also provides recombinant DNA or RNA molecules containing a 20P2H8 polynucleotide, including but not limited to phages, plasmids, phagemids, cosmids, YACs, BACs, as well as various viral and non-viral vectors well known in the art, and cells transformed or transfected with such recombinant DNA or RNA molecules. As used herein, a recombinant DNA or RNA molecule is a DNA or RNA molecule that has been subjected to molecular manipulation in vitro. Methods for generating such molecules are well known (see, e.g., Sambrook et al, 1989, supra).

The invention further provides a host-vector system comprising a recombinant DNA molecule containing a 20P2H8 polynucleotide within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HighFive cell). Examples of suitable mammalian cells include various prostate cancer cell lines such as PrEC, LNCaP and TsuPr1, other transfectable or transducible prostate cancer cell lines, as well as a number of mammalian cells routinely used for the expression of recombinant proteins (e.g., COS, CHO, 293, 293T cells). More particularly, a polynucleotide comprising the coding sequence of 20P2H8 may be used to generate 20P2H8 proteins or fragments thereof using any number of host-vector systems routinely used and widely known in the art.

A wide range of host-vector systems suitable for the expression of 20P2H8 proteins or fragments thereof are available (see, e.g., Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαt- kneo (Muller et al., 1991, MCB 11:1785). Using these expression vectors, 20P2H8 may be preferably expressed in several prostate cancer and non-prostate cell lines, including for example 293, 293T, rat-1, NIH 3T3 and TsuPr1. The host-vector systems of the invention are useful for the production of a 20P2H8 protein or fragment thereof. Such host-vector systems may be employed to study the functional properties of 20P2H8 and 20P2H8 mutations.

Recombinant human 20P2H8 protein may be produced by mammalian cells transfected with a construct encoding 20P2H8. In an illustrative embodiment described in the Examples, 293T cells can be transfected with an expression plasmid encoding 20P2H8, the 20P2H8 protein is expressed in the 293T cells, and the recombinant 20P2H8 protein can be isolated using standard purification methods (e.g., affinity purification using anti-20P2H8 antibodies). In another embodiment, also described in the Examples herein, the 20P2H8 coding sequence is subcloned into the retroviral vector pSRαMSVtkneo and used to infect various mammalian cell lines, such as NIH 3T3, TsuPr1, 293 and rat-1 in order to establish 20P2H8 expressing cell lines. Various other expression systems well known in the art may also be employed. Expression constructs encoding a leader peptide joined in frame to the 20P2H8 coding sequence may be used for the generation of a secreted form of recombinant 20P2H8 protein.

Proteins encoded by the 20P2H8 genes, or by fragments thereof, will have a variety of uses, including but not limited to generating antibodies and in methods for identifying ligands and other agents and cellular constituents that bind to a 20P2H8 gene product. Antibodies raised against a 20P2H8 protein (like 20P2H8 polynucleotides) or fragment thereof may be useful in diagnostic and prognostic assays, and imaging methodologies in the management of human cancers characterized by expression of 20P2H8 protein, including but not limited to cancers of the kidney, skin, cervix, prostate, brain, bladder, pancreas, ovaries, lung, testis and breast (see e.g. FIGS. 4-8). Such antibodies may be expressed intracellularly and used in methods of treating patients with such cancers. Various immunological assays useful for the detection of 20P2H8 proteins are contemplated, including but not limited to various types of radioimmunoassays, enzyme-linked immunosorbent assays (ELISA), enzyme-linked immunofluorescent assays (ELIFA), immunocytochemical methods, and the like. Such antibodies may be labeled and used as immunological imaging reagents capable of detecting 20P2H8 expressing cells (e.g., in radioscintigraphic imaging methods). 20P2H8 proteins may also be particularly useful in generating cancer vaccines, as further described below.

20P2H8 Polypeptides

Another aspect of the present invention provides 20P2H8 proteins and polypeptide fragments thereof. The 20P2H8 proteins of the invention include those specifically identified herein, as well as allelic variants, conservative substitution variants and homologs that can be isolated/generated and characterized without undue experimentation following the methods outlined below. Fusion proteins that combine parts of different 20P2H8 proteins or fragments thereof, as well as fusion proteins of a 20P2H8 protein and a heterologous polypeptide are also included. Such 20P2H8 proteins will be collectively referred to as the 20P2H8 proteins, the proteins of the invention, or 20P2H8. As used herein, the term "20P2H8 polypeptide" refers to a polypeptide fragment or a 20P2H8 protein of at least 6 amino acids, preferably at least 15 amino acids.

Specific embodiments of 20P2H8 proteins comprise a polypeptide having the amino acid sequence of human 20P2H8 as shown in SEQ ID NO: 2. Alternatively, embodiments of 20P2H8 proteins comprise variant polypeptides having alterations in the amino acid sequence of human 20P2H8 as shown in SEQ ID NO: 2.

In general, naturally occurring allelic variants of human 20P2H8 will share a high degree of structural identity and homology (e.g., 90% or more identity). Typically, allelic variants of the 20P2H8 proteins will contain conservative amino acid substitutions within the 20P2H8 sequences described herein or will contain a substitution of an amino acid from a corresponding position in a 20P2H8 homologue. One class of 20P2H8 allelic variants will be proteins that share a high degree of homology with at least a small region of a particular 20P2H8 amino acid sequence, but will further contain a radical departure from the sequence, such as a non-conservative substitution, truncation, insertion or frame shift.

Conservative amino acid substitutions can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

Embodiments of the invention disclosed herein include a wide variety of art accepted variants of 20P2H8 proteins such as polypeptides having amino acid insertions, deletions and substitutions. 20P2H8 variants can be made using methods known in the art such as site-directed mutagenesis, alanine scanning, and PCR mutagenesis. Site-directed mutagenesis (Carter et al., 1986, Nucl. Acids Res. 13:4331; Zoller et al., 1987, Nucl. Acids Res. 10:6487), cassette mutagenesis (Wells et al., 1985, Gene 34:315), restriction selection mutagenesis (Wells et al., 1986, Philos. Trans. R. Soc. London Ser. A, 317:415) or other known techniques can be performed on the cloned DNA to produce the 20P2H8 variant DNA. Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions (Creighton, The Proteins, (W.H. Freeman & Co., N.Y.); Chothia, 1976, J. Mol. Biol., 150:1). If alanine substitution does not yield adequate amounts of variant, an isosteric amino acid can be used.

As defined herein, 20P2H8 variants have the distinguishing attribute of having at least one epitope in common with a 20P2H8 protein having the amino acid sequence of SEQ ID NO: 2, such that an antibody that specifically binds to a 20P2H8 variant will also specifically bind to the 20P2H8 protein having the amino acid sequence of SEQ ID NO: 2. A polypeptide ceases to be a variant of the protein shown in SEQ ID NO: 2 when it no longer contains an epitope capable of being recognized by an antibody that specifically binds to a 20P2H8 protein. Those skilled in the art understand that antibodies that recognize proteins bind to epitopes of varying size, and a grouping of the order of about six amino acids, contiguous or not, is regarded as a typical number of amino acids in a minimal epitope. See e.g. Hebbes et al., Mol Immunol (1989) 26 (9):865-73; Schwartz et al., J Immunol (1985) 135 (4):2598-608. As there are approximately 20 amino acids that can be included at a given position within the minimal 6 amino acid epitope, an approximation of the odds of such an epitope occurring by chance are about $20^6$ or about 1 in 64 million. Another specific class of 20P2H8 protein variants shares 90% or more identity with the amino acid sequence of SEQ ID NO: 2. Another specific class of 20P2H8 protein variants comprises one or more of the 20P2H8 biological motifs described below.

As discussed above, embodiments of the claimed invention include polypeptides containing less than the 517 amino acid sequence of the 20P2H8 protein shown in SEQ ID NO: 2 (and the polynucleotides encoding such polypeptides). For example, representative embodiments of the invention disclosed herein include polypeptides consisting of about amino acid 1 to about amino acid 10 of the 20P2H8 protein shown in SEQ ID NO: 2, polypeptides consisting of about amino acid 20 to about amino acid 30 of the 20P2H8 protein shown in SEQ ID NO: 2, polypeptides consisting of about amino acid 30 to about amino acid 40 of the 20P2H8 protein shown in SEQ ID NO: 2, polypeptides consisting of about amino acid 40 to about amino acid 50 of the 20P2H8 protein shown in SEQ ID NO: 2, polypeptides consisting of about amino acid 50 to about amino acid 60 of the 20P2H8 protein shown in SEQ ID NO: 2, polypeptides consisting of about amino acid 60 to about amino acid 70 of the 20P2H8 protein shown in SEQ ID NO: 2, polypeptides consisting of about amino acid 70 to about amino acid 80 of the 20P2H8 protein shown in SEQ ID NO: 2, polypeptides consisting of about amino acid 80 to about amino acid 90 of the 20P2H8 protein shown in SEQ ID NO: 2 and polypeptides consisting of about amino acid 90 to about amino acid 100 of the 20P2H8 protein shown in SEQ ID NO: 2, etc. Following this scheme, polypeptides consisting of portions of the amino acid sequence of amino acids 100-517 of the 20P2H8 protein are typical embodiments of the invention. Polypeptides consisting of larger portions of the 20P2H8 protein are also contemplated. For example polypeptides consisting of about amino acid 1 (or 20 or 30 or 40 etc.) to about amino acid 20, (or 30, or 40 or 50 etc.) of the 20P2H8 protein shown in SEQ ID NO: 2 may be generated by a variety of techniques well known in the art.

Additional illustrative embodiments of the invention disclosed herein include 20P2H8 polypeptides containing the amino acid residues of one or more of the biological motifs contained within the 20P2H8 polypeptide sequence as shown in SEQ ID NO: 2. In one embodiment, typical polypeptides of the invention can contain one or more of the 20P2H8 N-glycosylation sites such as NYTA at residues 436-439 and/or NLSG at residues 459-462 (SEQ ID NO: 2). In another embodiment, typical polypeptides of the invention can contain one or more of the 20P2H8 casein kinase II phosphorylation sites such as SQVE at residues 19-22, SDPE at residues 41-44, SKME at residues 56-59, SDQD at residues 77-80, TGED at residues 141-144, TSNE at residues 152-155, TAEE at residues 178-181, TYPD at residues 203-206, TAAE at residues 245-248, TIED at residues 297-300 and/or SAEE at residues 364-367 (SEQ ID NO: 2). In another embodiment, typical polypeptides of the invention can contain one or more of the N-myristoylation sites such as GLNIAK at residues 87-92, GAALCL at residues 94-99, GGTSNE at residues 150-155, GLPFTA at residues 172-177, GGKEGI at residues 194-199, GLPYAA at residues 291-296, GGTLNR at residues 374-379, GSPNSL at residues 446-451, GLAYNT at residues 475-480 and/or GLIHTN at residues 499-504 (SEQ ID NO: 2). In another embodiment, typical polypeptides of the invention can contain the one or more of the amidation sites such as QGRR at residues 102-105 and/or LGKR at residues 234-237 (SEQ ID NO: 2). In another embodiment, typical polypeptides of the invention can contain one or more of the RNA-binding domains such as those shown in FIG. 1. In another embodiment, typical polypeptides of the invention can contain one or more of the proline rich regions such as those shown in FIG. 1. In another embodiment, typical polypeptides of the invention can contain one or more of the immunoreactive epitopes identified by a process described herein such as such as those shown in Table 1. Related embodiments of these inventions include polypeptides containing combinations of the different motifs discussed above with preferable embodiments being those which contain no insertions, deletions or substitutions either within the motifs or the intervening sequences of these polypeptides. In addition, embodiments which include a number of either N-terminal and/or C-terminal amino acid residues on either side of these motifs may be desirable (to, for example, include a greater portion of the polypeptide architecture in which the motif is located). Typically the number of N-terminal and/or C-terminal amino acid residues on either side of a motif is between about 5 to about 50 amino acid residues.

Illustrative examples of such embodiments includes a polypeptide having one or more motifs selected from the group consisting of SDPE and/or SKME and/or TGED (SEQ ID NO: 2). Alternatively, polypeptides having other combinations of the biological motifs disclosed herein are also contemplated such as a polypeptide having GLIHN and any one of the other biological motifs such as SKME or a polypeptide having GLIHN and any one of the other biological motifs such as GGKEGI etc. (SEQ ID NO: 2).

Figure 4:
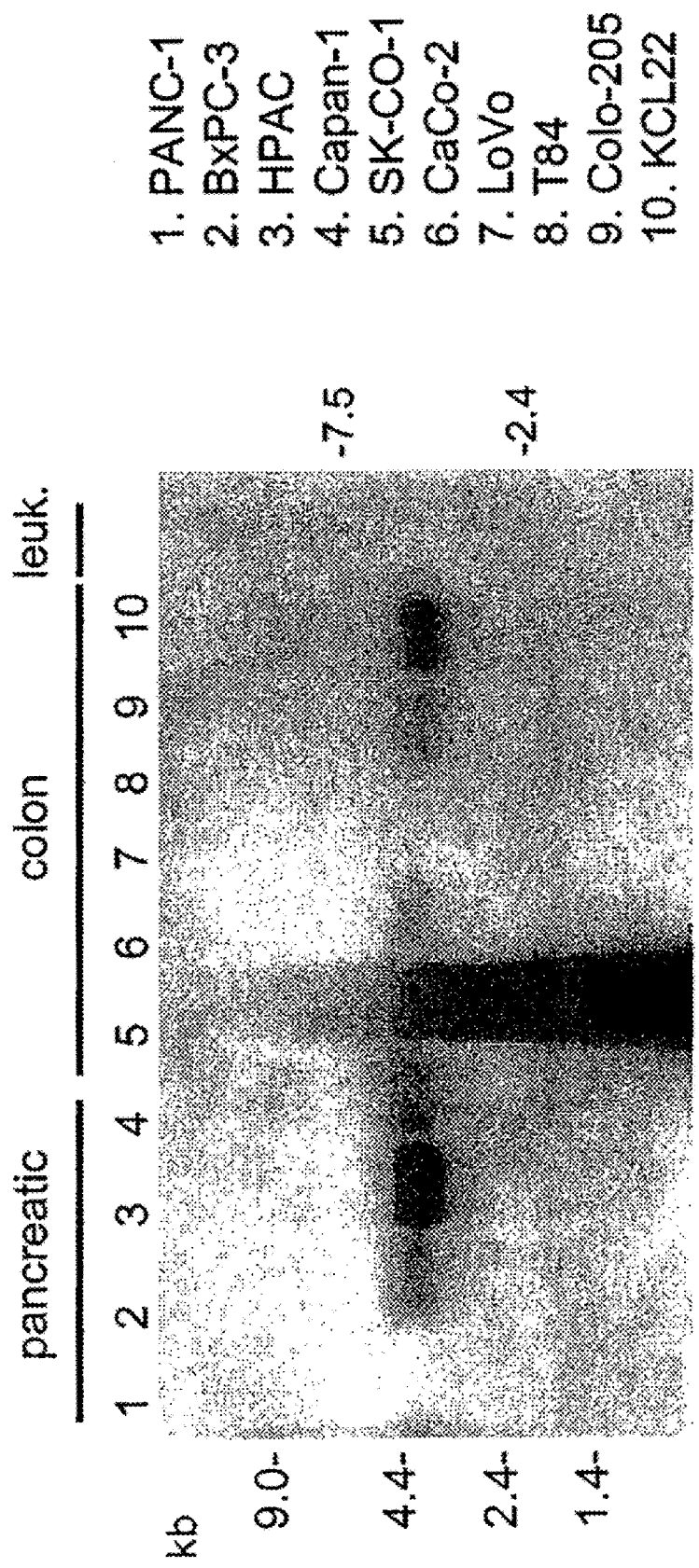
FIG. 4 shows a Northern blot analysis of human 20P2H8 mRNA expression in a panel of human colon and pancreatic cancer cell lines.
Figure 5:
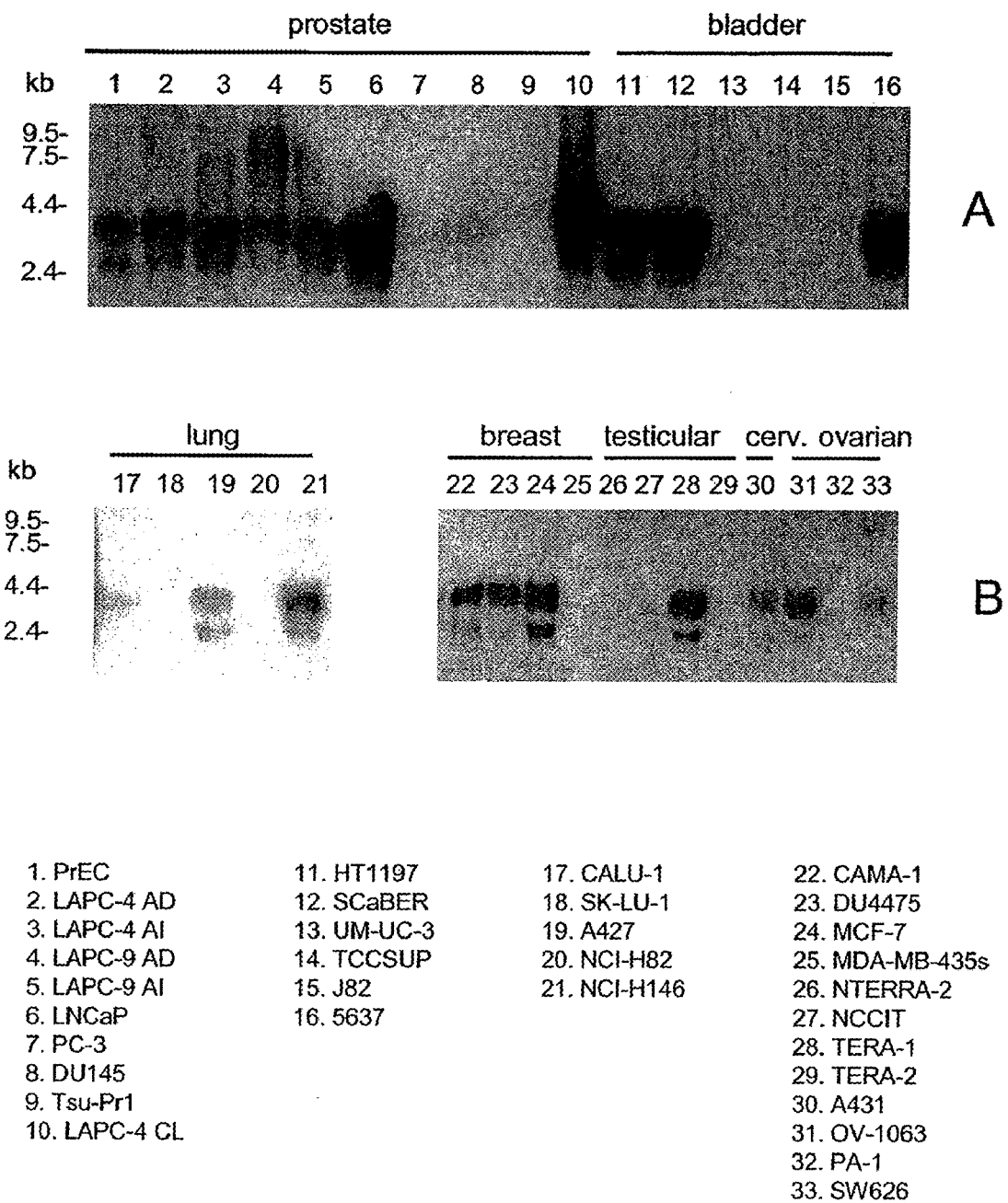
FIGS. 5A-5B show a Northern expression analysis of 20P2H8 mRNA in many cancer lines including bladder, lung, breast, testicular cervical and ovarian cancers.
Figure 6:
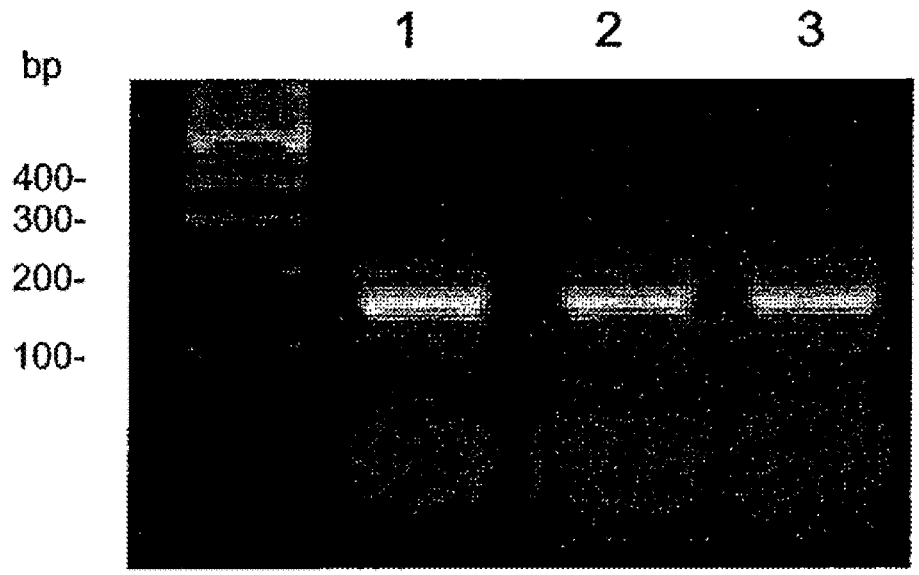
FIG. 6 illustrates an RT-PCR analysis showing expression of the of 20P2H8 mRNA in bladder cancer, colon cancer, and lung cancer patients.

Polypeptides consisting of one or more of the 20P2H8 motifs discussed above are useful in elucidating the specific characteristics of a malignant phenotype in view of the observation that the 20P2H8 motifs discussed above are associated with growth dysregulation and because 20P2H8 is overexpressed in cancers (FIGS. 4 and 5). Casein kinase II and protein kinase C for example are enzymes known to be associated with the development of the malignant phenotype (see e.g. Chen et al., 1998, Lab Invest., 78 (2):165-174; Gaiddon et al., 1995, Endocrinology 136 (10):4331-4338; Hall et al., 1996, Nucleic Acids Research 24 (6):1119-1126; Peterziel et al., 1999, Oncogene 18 (46):6322-6329; and O'Brian, 1998, Oncol. Rep. 5 (2): 305-309). Moreover, both glycosylation and myristoylation are protein modifications also associated with cancer and cancer progression (see e.g. Dennis et al., 1999, Biochim. Biophys. Acta 1473 (1):21-34; Raju et al., 1997, Exp. Cell Res. 235 (1):145-154). In addition, the RNA recognition motifs and proline rich regions are also associated with oncogenic processes (see e.g. Kennedy et al. Nat. Genet. 12 (3): 329-331 (1996): Li et al., J. Biol. Chem. 275 (30): 23053-23058 (2000) and Xiao et al., Blood. 2000 Jul. 15; 96 (2):699-704).

The polypeptides of the preceding paragraphs have a number of different specific uses. As 20P2H8 is shown to be expressed in a variety of cancers including kidney, prostate, bladder, testicular, ovarian, breast, pancreas, colon, skin, cervical, stomach and lung cancer cell lines and/or patient samples (see e.g. FIGS. 4-8), these polypeptides may be used in methods assessing the status of 20P2H8 gene products in normal versus cancerous tissues and elucidating the malignant phenotype. Typically, polypeptides encoding specific regions of the 20P2H8 protein may be used to assess the presence of perturbations (such as deletions, insertions, point mutations etc.) in specific regions of the 20P2H8 gene products (such as regions containing the RNA binding motifs). Exemplary assays can utilize antibodies targeting a 20P2H8 polypeptide containing the amino acid residues of one or more of the biological motifs contained within the 20P2H8 polypeptide sequence in order to evaluate the characteristics of this region in normal versus cancerous tissues. Alternatively, 20P2H8 polypeptides containing the amino acid residues of one or more of the biological motifs contained within the 20P2H8 polypeptide sequence can be used to screen for factors that interact with that region of 20P2H8.

As discussed above, redundancy in the genetic code permits variation in 20P2H8 gene sequences. In particular, one skilled in the art will recognize specific codon preferences by a specific host species and can adapt the disclosed sequence as preferred for a desired host. For example, preferred codon sequences typically have rare codons (i.e., codons having a usage frequency of less than about 20% in known sequences of the desired host) replaced with higher frequency codons. Codon preferences for a specific organism may be calculated, for example, by utilizing codon usage tables available on the Internet at the following address: http://www.dna.affrc.go.jp/~nakamura/codon.html. Nucleotide sequences that have been optimized for a particular host species by replacing any codons having a usage frequency of less than about 20% are referred to herein as "codon optimized sequences."

Additional sequence modifications are known to enhance protein expression in a cellular host. These include elimination of sequences encoding spurious polyadenylation signals, exon/intron splice site signals, transposon-like repeats, and/or other such well-characterized sequences that may be deleterious to gene expression. The GC content of the sequence may be adjusted to levels average for a given cellular host, as calculated by reference to known genes expressed in the host cell. Where possible, the sequence may also be modified to avoid predicted hairpin secondary mRNA structures. Other useful modifications include the addition of a translational initiation consensus sequence at the start of the open reading frame, as described in Kozak, 1989, Mol. Cell. Biol., 9:5073-5080. Nucleotide sequences that have been optimized for expression in a given host species by elimination of spurious polyadenylation sequences, elimination of exon/intron splicing signals, elimination of transposon-like repeats and/or optimization of GC content in addition to codon optimization are referred to herein as an "expression enhanced sequence."

20P2H8 proteins may be embodied in many forms, preferably in isolated form. As used herein, a protein is said to be "isolated" when physical, mechanical or chemical methods are employed to remove the 20P2H8 protein from cellular constituents that are normally associated with the protein. A skilled artisan can readily employ standard purification methods to obtain an isolated 20P2H8 protein. A purified 20P2H8 protein molecule will be substantially free of other proteins or molecules that impair the binding of 20P2H8 to antibody or other ligand. The nature and degree of isolation and purification will depend on the intended use. Embodiments of a 20P2H8 protein include a purified 20P2H8 protein and a functional, soluble 20P2H8 protein. In one form, such functional, soluble 20P2H8 proteins or fragments thereof retain the ability to bind antibody or other ligand.

The invention also provides 20P2H8 polypeptides comprising biologically active fragments of the 20P2H8 amino acid sequence, such as a polypeptide corresponding to part of the amino acid sequence for 20P2H8 as shown in SEQ ID NO: 2. Such polypeptides of the invention exhibit properties of the 20P2H8 protein, such as the ability to elicit the generation of antibodies that specifically bind an epitope associated with the 20P2H8 protein.

20P2H8 polypeptides can be generated using standard peptide synthesis technology or using chemical cleavage methods well known in the art based on the amino acid sequences of the human 20P2H8 proteins disclosed herein. Alternatively, recombinant methods can be used to generate nucleic acid molecules that encode a polypeptide fragment of a 20P2H8 protein. In this regard, the 20P2H8-encoding nucleic acid molecules described herein provide means for generating defined fragments of 20P2H8 proteins. 20P2H8 polypeptides are particularly useful in generating and characterizing domain specific antibodies (e.g., antibodies recognizing an extracellular or intracellular epitope of a 20P2H8 protein), in identifying agents or cellular factors that bind to 20P2H8 or a particular structural domain thereof, and in various therapeutic contexts, including but not limited to cancer vaccines.

20P2H8 polypeptides containing particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or on the basis of immunogenicity. Fragments containing such structures are particularly useful in generating subunit specific anti-20P2H8 antibodies or in identifying cellular factors that bind to 20P2H8.

In an embodiment described in the examples that follow, 20P2H8 can be conveniently expressed in cells (such as 293T cells) transfected with a commercially available expression vector such as a CMV-driven expression vector encoding 20P2H8 with a C-terminal 6×His and MYC tag (pcDNA3.1/mycHIS, Invitrogen or Tag5, GenHunter Corporation, Nashville Tenn.). The Tag5 vector provides an IgGK secretion signal that can be used to facilitate the production of a secreted 20P2H8 protein in transfected cells. The secreted HIS-tagged 20P2H8 in the culture media may be purified using a nickel column using standard techniques.

Modifications of 20P2H8 such as covalent modifications are included within the scope of this invention. One type of covalent modification includes reacting targeted amino acid residues of a 20P2H8 polypeptide with an organic derivatizing agent that is capable of reacting with selected side chains or the N- or C-terminal residues of the 20P2H8. Another type of covalent modification of the 20P2H8 polypeptide included within the scope of this invention comprises altering the native glycosylation pattern of the polypeptide. "Altering the native glycosylation pattern" is intended for purposes herein to mean deleting one or more carbohydrate moieties found in native sequence 20P2H8 (either by removing the underlying glycosylation site or by deleting the glycosylation by chemical and/or enzymatic means), and/or adding one or more glycosylation sites that are not present in the native sequence 20P2H8. In addition, the phrase includes qualitative changes in the glycosylation of the native proteins, involving a change in the nature and proportions of the various carbohydrate moieties present. Another type of covalent modification of 20P2H8 comprises linking the 20P2H8 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The 20P2H8 of the present invention may also be modified in a way to form a chimeric molecule comprising 20P2H8 fused to another, heterologous polypeptide or amino acid sequence. In one embodiment, such a chimeric molecule comprises a fusion of the 20P2H8 with a polyhistidine epitope tag, which provides an epitope to which immobilized nickel can selectively bind. The epitope tag is generally placed at the amino- or carboxyl-terminus of the 20P2H8. In an alternative embodiment, the chimeric molecule may comprise a fusion of the 20P2H8 with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a 20P2H8 polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

20P2H8 Antibodies

The term "antibody" is used in the broadest sense and specifically covers single anti-20P2H8 monoclonal antibodies (including agonist, antagonist and neutralizing antibodies) and anti-20P2H8 antibody compositions with polyepitopic specificity. The term "monoclonal antibody" (mAb) as used herein refers to an antibody obtained from a population of substantially homogeneous antibodies, i.e. the antibodies comprising the individual population are identical except for possible naturally-occurring mutations that may be present in minor amounts.

Another aspect of the invention provides antibodies that bind to 20P2H8 proteins and polypeptides. The most preferred antibodies will specifically bind to a 20P2H8 protein and will not bind (or will bind weakly) to non-20P2H8 proteins and polypeptides. Anti-20P2H8 antibodies that are particularly contemplated include monoclonal and polyclonal antibodies as well as fragments containing the antigen binding domain and/or one or more complementarity determining regions of these antibodies. As used herein, an antibody fragment is defined as at least a portion of the variable region of the immunoglobulin molecule that binds to its target, i.e., the antigen binding region.

20P2H8 antibodies of the invention may be particularly useful in prostate cancer diagnostic and prognostic assays, and imaging methodologies. Intracellularly expressed antibodies (e.g., single chain antibodies) may be therapeutically useful in treating cancers in which the expression of 20P2H8 is involved, such as for example advanced and metastatic prostate cancers. Such antibodies may be useful in the treatment, diagnosis, and/or prognosis of other cancers, to the extent 20P2H8 is also expressed or overexpressed in other types of cancers such as prostate, kidney, bladder, cervical, skin, stomach, testicular, ovarian, breast, pancreas, colon and lung cancers.

The invention also provides various immunological assays useful for the detection and quantification of 20P2H8 and mutant 20P2H8 proteins and polypeptides. Such assays generally comprise one or more 20P2H8 antibodies capable of recognizing and binding a 20P2H8 or mutant 20P2H8 protein, as appropriate, and may be performed within various immunological assay formats well known in the art, including but not limited to various types of radioimmunoassays, enzyme-linked immunosorbent assays (ELISA), enzyme-linked immunofluorescent assays (ELIFA), and the like. In addition, immunological imaging methods capable of detecting prostate cancer and other cancers expressing 20P2H8 are also provided by the invention, including but limited to radioscintigraphic imaging methods using labeled 20P2H8 antibodies. Such assays may be clinically useful in the detection, monitoring, and prognosis of 20P2H8 expressing cancers such as prostate, bladder, testicular, ovarian, breast, pancreas, colon and lung cancer cell lines.

20P2H8 antibodies may also be used in methods for purifying 20P2H8 and mutant 20P2H8 proteins and polypeptides and for isolating 20P2H8 homologues and related molecules. For example, in one embodiment, the method of purifying a 20P2H8 protein comprises incubating a 20P2H8 antibody, which has been coupled to a solid matrix, with a lysate or other solution containing 20P2H8 under conditions that permit the 20P2H8 antibody to bind to 20P2H8; washing the solid matrix to eliminate impurities; and eluting the 20P2H8 from the coupled antibody. Other uses of the 20P2H8 antibodies of the invention include generating anti-idiotypic antibodies that mimic the 20P2H8 protein.

Various methods for the preparation of antibodies are well known in the art. For example, antibodies may be prepared by immunizing a suitable mammalian host using a 20P2H8 protein, peptide, or fragment, in isolated or immunoconjugated form (Harlow, and Lane, eds., 1988, Antibodies: A Laboratory Manual, CSH Press; Harlow, 1989, Antibodies, Cold Spring Harbor Press, NY). In addition, fusion proteins of 20P2H8 may also be used, such as a 20P2H8 GST-fusion protein. In a particular embodiment, a GST fusion protein comprising all or most of the open reading frame amino acid sequence of SEQ ID NO: 2 may be produced and used as an immunogen to generate appropriate antibodies. In another embodiment, a 20P2H8 peptide may be synthesized and used as an immunogen.

In addition, naked DNA immunization techniques known in the art may be used (with or without purified 20P2H8 protein or 20P2H8 expressing cells) to generate an immune response to the encoded immunogen (for review, see Donnelly et al., 1997, Ann. Rev. Immunol. 15:617-648).

The amino acid sequence of the 20P2H8 as shown in SEQ ID NO: 2 may be used to select specific regions of the 20P2H8 protein for generating antibodies. For example, hydrophobicity and hydrophilicity analyses of the 20P2H8 amino acid sequence may be used to identify hydrophilic regions in the 20P2H8 structure. Regions of the 20P2H8 protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis.

Illustrating this, the binding of peptides from 20P2H8 proteins to the human MHC class I molecule HLA-A2 are predicted and shown in Table 1 below. Specifically, the complete amino acid sequences of 20P2H8 proteins was entered into the HLA Peptide Motif Search algorithm found in the Bioinformatics and Molecular Analysis Section (BIMAS) Web site (http://bimas.dcrt.nih.gov/). The HLA Peptide Motif Search algorithm was developed by Dr. Ken Parker based on binding of specific peptide sequences in the groove of HLA Class I molecules and specifically HLA-A2 (see e.g. Falk et al., Nature 351: 290-6 (1991); Hunt et al., Science 255:1261-3 (1992); Parker et al., J. Immunol. 149:3580-7 (1992); Parker et al., J. Immunol. 152:163-75 (1994)). This algorithm allows location and ranking of 8-mer, 9-mer, and 10-mer peptides from a complete protein sequence for predicted binding to HLA-A2 as well as other HLA Class I molecules. Most HLA-A2 binding peptides are 9-mers favorably containing a leucine (L) at position 2 and a valine (V) or leucine (L) at position 9 (Parker et al., J. Immunol. 149:3580-7 (1992)). The results of 20P2H8 predicted binding peptides are shown in Table 1 below. In Table 1, the top 10 ranking candidates for each family member are shown along with their location, the amino acid sequence of each specific peptide, and an estimated binding score. The binding score corresponds to the estimated half-time of dissociation of complexes containing the peptide at 37° C. at pH 6.5. Peptides with the highest binding score are predicted to be the most tightly bound to HLA Class I on the cell surface and thus represent the best immunogenic targets for T-cell recognition. Actual binding of peptides to HLA-A2 can be evaluated by stabilization of HLA-A2 expression on the antigen-processing defective cell line T2 (see e.g. Xue et al., Prostate 30:73-8 (1997) and Peshwa et al., Prostate 36:129-38 (1998)). Immunogenicity of specific peptides can be evaluated in vitro by stimulation of CD8+ cytotoxic T lymphocytes (CTL) in the presence of dendritic cells.

Methods for preparing a protein or polypeptide for use as an immunogen and for preparing immunogenic conjugates of a protein with a carrier such as BSA, KLH, or other carrier proteins are well known in the art. In some circumstances, direct conjugation using, for example, carbodiimide reagents may be used; in other instances linking reagents such as those supplied by Pierce Chemical Co., Rockford, Ill., may be effective. Administration of a 20P2H8 immunogen is conducted generally by injection over a suitable time period and with use of a suitable adjuvant, as is generally understood in the art. During the immunization schedule, titers of antibodies can be taken to determine adequacy of antibody formation.

20P2H8 monoclonal antibodies are preferred and may be produced by various means well known in the art. For example, immortalized cell lines that secrete a desired monoclonal antibody may be prepared using the standard hybridoma technology of Kohler and Milstein or modifications that immortalize producing B cells, as is generally known. The immortalized cell lines secreting the desired antibodies are screened by immunoassay in which the antigen is the 20P2H8 protein or a 20P2H8 fragment. When the appropriate immortalized cell culture secreting the desired antibody is identified, the cells may be expanded and antibodies produced either from in vitro cultures or from ascites fluid.

The antibodies or fragments may also be produced, using current technology, by recombinant means. Regions that bind specifically to the desired regions of the 20P2H8 protein can also be produced in the context of chimeric or CDR grafted antibodies of multiple species origin. Humanized or human 20P2H8 antibodies may also be produced and are preferred for use in therapeutic contexts. Methods for humanizing murine and other non-human antibodies by substituting one or more of the non-human antibody CDRs for corresponding human antibody sequences are well known (see for example, Jones et al., 1986, Nature 321:522-525; Riechmann et al., 1988, Nature 332:323-327; Verhoeyen et al., 1988, Science 239:1534-1536). See also, Carter et al., 1993, Proc. Natl. Acad. Sci. USA 89:4285 and Sims et al., 1993, J. Immunol. 151:2296. Methods for producing fully human monoclonal antibodies include phage display and transgenic methods (for review, see Vaughan et al., 1998, Nature Biotechnology 16:535-539).

Fully human 20P2H8 monoclonal antibodies may be generated using cloning technologies employing large human Ig gene combinatorial libraries (i.e., phage display) (Griffiths and Hoogenboom, Building an in vitro immune system: human antibodies from phage display libraries. In: Clark, M., ed., 1993, Protein Engineering of Antibody Molecules for Prophylactic and Therapeutic Applications in Man, Nottingham Academic, pp 45-64; Burton and Barbas, Human Antibodies from combinatorial libraries. Id., pp 65-82). Fully human 20P2H8 monoclonal antibodies may also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4):607-614). This method avoids the in vitro manipulation required with phage display technology and efficiently produces high affinity authentic human antibodies.

Reactivity of 20P2H8 antibodies with a 20P2H8 protein may be established by a number of well known means, including western blot, immunoprecipitation, ELISA, and FACS analyses using, as appropriate, 20P2H8 proteins, peptides, 20P2H8-expressing cells or extracts thereof.

A 20P2H8 antibody or fragment thereof of the invention may be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. A second molecule for conjugation to the 20P2H8 antibody can be selected in accordance with the intended use. For example, for therapeutic use, the second molecule can be a toxin or therapeutic agent. Further, bi-specific antibodies specific for two or more 20P2H8 epitopes may be generated using methods generally known in the art. Homodimeric antibodies may also be generated by cross-linking techniques known in the art (e.g., Wolff et al., 1993, Cancer Res. 53: 2560-2565).

20P2H8 Transgenic Animals

Nucleic acids that encode 20P2H8 or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA that is integrated into the genome of a cell from which a transgenic animal develops. In one embodiment, cDNA encoding 20P2H8 can be used to clone genomic DNA encoding 20P2H8 in accordance with established techniques and the genomic sequences used to generate transgenic animals that contain cells that express DNA encoding 20P2H8. Methods for generating transgenic animals, particularly animals such as mice or rats, have become conventional in the art and are described, for example, in U.S. Pat. Nos. 4,736,866 and 4,870,009. Typically, particular cells would be targeted for 20P2H8 transgene incorporation with tissue-specific enhancers. Transgenic animals that include a copy of a transgene encoding 20P2H8 introduced into the germ line of the animal at an embryonic stage can be used to examine the effect of increased expression of DNA encoding 20P2H8. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of 20P2H8 can be used to construct a 20P2H8 "knock out" animal that has a defective or altered gene encoding 20P2H8 as a result of homologous recombination between the endogenous gene encoding 20P2H8 and altered genomic DNA encoding 20P2H8 introduced into an embryonic cell of the animal. For example, cDNA encoding 20P2H8 can be used to clone genomic DNA encoding 20P2H8 in accordance with established techniques. A portion of the genomic DNA encoding 20P2H8 can be deleted or replaced with another gene, such as a gene encoding a selectable marker that can be used to monitor integration. Typically, several kilobases of unaltered flanking DNA (both at the 5' and 3' ends) are included in the vector (see e.g., Thomas and Capecchi, 1987, Cell 51:503) for a description of homologous recombination vectors]. The vector is introduced into an embryonic stem cell line (e.g., by electroporation) and cells in which the introduced DNA has homologously recombined with the endogenous DNA are selected (see e.g., Li et al., 1992, Cell 69:915). The selected cells are then injected into a blastocyst of an animal (e.g., a mouse or rat) to form aggregation chimeras (see e.g., Bradley, in Robertson, ed., 1987, Teratocarcinomas and Embryonic Stem Cells: A Practical Approach, (IRL, Oxford), pp. 113-152). A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the 20P2H8 polypeptide.

Methods for the Detection of 20P2H8

Another aspect of the present invention relates to methods for detecting 20P2H8 polynucleotides and 20P2H8 proteins and variants thereof, as well as methods for identifying a cell that expresses 20P2H8. The expression profile of 20P2H8 makes it a potential diagnostic marker for local and/or metastasized disease. Northern blot analysis suggests that different tissues express different isoforms of 20P2H8. The 20P2H8 isoforms in prostate cancer appear to be different from the isoform expressed in normal prostate. In this context, the status of 20P2H8 gene products may provide information useful for predicting a variety of factors including susceptibility to advanced stage disease, rate of progression, and/or tumor aggressiveness. As discussed in detail below, the status of 20P2H8 gene products in patient samples may be analyzed by a variety protocols that are well known in the art including immunohistochemical analysis, the variety of Northern blotting techniques including in situ hybridization, RT-PCR analysis (for example on laser capture micro-dissected samples), western blot analysis and tissue array analysis.

More particularly, the invention provides assays for the detection of 20P2H8 polynucleotides in a biological sample, such as serum, bone, prostate, and other tissues, urine, semen, cell preparations, and the like. Detectable 20P2H8 polynucleotides include, for example, a 20P2H8 gene or fragments thereof, 20P2H8 mRNA, alternative splice variant 20P2H8 mRNAs, and recombinant DNA or RNA molecules containing a 20P2H8 polynucleotide. A number of methods for amplifying and/or detecting the presence of 20P2H8 polynucleotides are well known in the art and may be employed in the practice of this aspect of the invention.

In one embodiment, a method for detecting a 20P2H8 mRNA in a biological sample comprises producing cDNA from the sample by reverse transcription using at least one primer; amplifying the cDNA so produced using a 20P2H8 polynucleotides as sense and antisense primers to amplify 20P2H8 cDNAs therein; and detecting the presence of the amplified 20P2H8 cDNA. Optionally, the sequence of the amplified 20P2H8 cDNA can be determined. In another embodiment, a method of detecting a 20P2H8 gene in a biological sample comprises first isolating genomic DNA from the sample; amplifying the isolated genomic DNA using 20P2H8 polynucleotides as sense and antisense primers to amplify the 20P2H8 gene therein; and detecting the presence of the amplified 20P2H8 gene. Any number of appropriate sense and antisense probe combinations may be designed from the nucleotide sequences provided for the 20P2H8 (SEQ ID NO: 1) and used for this purpose.

The invention also provides assays for detecting the presence of a 20P2H8 protein in a tissue of other biological sample such as serum, bone, prostate, and other tissues, urine, cell preparations, and the like. Methods for detecting a 20P2H8 protein are also well known and include, for example, immunoprecipitation, immunohistochemical analysis, Western Blot analysis, molecular binding assays, ELISA, ELIFA and the like. For example, in one embodiment, a method of detecting the presence of a 20P2H8 protein in a biological sample comprises first contacting the sample with a 20P2H8 antibody, a 20P2H8-reactive fragment thereof, or a recombinant protein containing an antigen binding region of a 20P2H8 antibody; and then detecting the binding of 20P2H8 protein in the sample thereto.

Methods for identifying a cell that expresses 20P2H8 are also provided. In one embodiment, an assay for identifying a cell that expresses a 20P2H8 gene comprises detecting the presence of 20P2H8 mRNA in the cell. Methods for the detection of particular mRNAs in cells are well known and include, for example, hybridization assays using complementary DNA probes (such as in situ hybridization using labeled 20P2H8 riboprobes, Northern blot and related techniques) and various nucleic acid amplification assays (such as RT-PCR using complementary primers specific for 20P2H8, and other amplification type detection methods, such as, for example, branched DNA, SISBA, TMA and the like). Alternatively, an assay for identifying a cell that expresses a 20P2H8 gene comprises detecting the presence of 20P2H8 protein in the cell or secreted by the cell. Various methods for the detection of proteins are well known in the art and may be employed for the detection of 20P2H8 proteins and 20P2H8 expressing cells.

20P2H8 expression analysis may also be useful as a tool for identifying and evaluating agents that modulate 20P2H8 gene expression. For example, 20P2H8 expression is significantly upregulated in prostate cancer, and may also be expressed in other cancers. Identification of a molecule or biological agent that could inhibit 20P2H8 expression or over-expression in cancer cells may be of therapeutic value. Such an agent may be identified by using a screen that quantifies 20P2H8 expression by RT-PCR, nucleic acid hybridization or antibody binding.

Monitoring the Status of 20P2H8 and its Products

Assays that evaluate the status of the 20P2H8 gene and 20P2H8 gene products in an individual may provide information on the growth or oncogenic potential of a biological sample from this individual. For example, because 20P2H8 mRNA is so highly expressed in prostate cancers as compared to normal prostate tissue, assays that evaluate the relative levels of 20P2H8 mRNA transcripts or proteins in a biological sample may be used to diagnose a disease associated with 20P2H8 dysregulation such as cancer and may provide prognostic information useful in defining appropriate therapeutic options.

Because 20P2H8 is expressed, for example, in various prostate cancer xenograft tissues and cancer cell lines, and cancer patient samples, the expression status of 20P2H8 can provide information useful for determining information including the presence, stage and location of displasic, precancerous and cancerous cells, predicting susceptibility to various stages of disease, and/or for gauging tumor aggressiveness. Moreover, the expression profile makes it a potential imaging reagent for metastasized disease. Consequently, an important aspect of the invention is directed to the various molecular prognostic and diagnostic methods for examining the status of 20P2H8 in biological samples such as those from individuals suffering from, or suspected of suffering from a pathology characterized by dysregulated cellular growth such as cancer.

Oncogenesis is known to be a multistep process where cellular growth becomes progressively dysregulated and cells progress from a normal physiological state to precancerous and then cancerous states (see e.g. Alers et al., Lab Invest. 77 (5): 437-438 (1997) and Isaacs et al., Cancer Surv. 23:19-32 (1995)). In this context, examining a biological sample for evidence of dysregulated cell growth (such as aberrant 20P2H8 expression in prostate cancers) can allow the early detection of such aberrant cellular physiology before a pathology such as cancer has progressed to a stage at which therapeutic options are more limited. In such examinations, the status of 20P2H8 in a biological sample of interest (such as one suspected of having dysregulated cell growth) can be compared, for example, to the status of 20P2H8 in a corresponding normal sample (e.g. a sample from that individual (or alternatively another individual) that is not effected by a pathology, for example one not suspected of having dysregulated cell growth) with alterations in the status of 20P2H8 in the biological sample of interest (as compared to the normal sample) providing evidence of dysregulated cellular growth. In addition to using a biological sample that is not effected by a pathology as a normal sample, one can also use a predetermined normative value such as a predetermined normal level of mRNA expression (see e.g. Grever et al., J. Comp. Neurol. 1996 Dec. 9; 376 (2):306-14 and U.S. Pat. No. 5,837,501) to compare 20P2H8 in normal versus suspect samples.

The term "status" in this context is used according to its art accepted meaning and refers to the condition or state of a gene and its products. As specifically described herein, the status of 20P2H8 can be evaluated by a number of parameters known in the art. Typically an alteration in the status of 20P2H8 comprises a change in the location of 20P2H8 expressing cells and/or an increase in 20P2H8 mRNA and/or protein expression.

Typically, skilled artisans use a number of parameters to evaluate the condition or state of a gene and its products. These include, but are not limited to the location of expressed gene products (including the location of 20P2H8 expressing cells) as well as the, level, and biological activity of expressed gene products (such as 20P2H8 mRNA polynucleotides and polypeptides). Alterations in the status of 20P2H8 can be evaluated by a wide variety of methodologies well known in the art, typically those discussed below. Typically an alteration in the status of 20P2H8 comprises a change in the location of 20P2H8 and/or 20P2H8 expressing cells and/or an increase in 20P2H8 mRNA and/or protein expression.

As discussed in detail herein, in order to identify a condition or phenomenon associated with dysregulated cell growth, the status of 20P2H8 in a biological sample may be evaluated by a number of methods utilized by skilled artisans including, but not limited to genomic Southern analysis (to examine, for example perturbations in the 20P2H8 gene), northerns and/or PCR analysis of 20P2H8 mRNA (to examine, for example alterations in the polynucleotide sequences or expression levels of 20P2H8 mRNAs), and western and/or immunohistochemical analysis (to examine, for example alterations in polypeptide sequences, alterations in polypeptide localization within a sample, alterations in expression levels of 20P2H8 proteins and/or associations of 20P2H8 proteins with polypeptide binding partners). Detectable 20P2H8 polynucleotides include, for example, a 20P2H8 gene or fragments thereof, 20P2H8 mRNA, alternative splice variants 20P2H8 mRNAs, and recombinant DNA or RNA molecules containing a 20P2H8 polynucleotide.

The expression profile of 20P2H8 makes it a potential diagnostic marker for local and/or metastasized disease. In particular, the status of 20P2H8 may provide information useful for predicting susceptibility to particular disease stages, progression, and/or tumor aggressiveness. The invention provides methods and assays for determining 20P2H8 status and diagnosing cancers that express 20P2H8, such as cancers of the prostate, bladder, testis, ovaries, breast, pancreas, colon and lung. 20P2H8 status in patient samples may be analyzed by a number of means well known in the art, including without limitation, immunohistochemical analysis, in situ hybridization, RT-PCR analysis on laser capture micro-dissected samples, western blot analysis of clinical samples and cell lines, and tissue array analysis. Typical protocols for evaluating the status of the 20P2H8 gene and gene products can be found, for example in Ausubul et al. eds., 1995, Current Protocols In Molecular Biology, Units 2 [Northern Blotting], 4 [Southern Blotting], 15 [Immunoblotting] and 18 [PCR Analysis].

As described above, the status of 20P2H8 in a biological sample can be examined by a number of well known procedures in the art. For example, the status of 20P2H8 in a biological sample taken from a specific location in the body can be examined by evaluating the sample for the presence or absence of 20P2H8 expressing cells (e.g. those that express 20P2H8 mRNAs or proteins). This examination can provide evidence of dysregulated cellular growth for example, when 20P2H8 expressing cells are found in a biological sample that does not normally contain such cells (such as a lymph node). Such alterations in the status of 20P2H8 in a biological sample are often associated with dysregulated cellular growth. Specifically, one indicator of dysregulated cellular growth is the metastases of cancer cells from an organ of origin (such as the testis or prostate gland) to a different area of the body (such as a lymph node). In this context, evidence of dysregulated cellular growth is important for example because occult lymph node metastases can be detected in a substantial proportion of patients with prostate cancer, and such metastases are associated with known predictors of disease progression (see e.g. J Urol 1995 August; 154 (2 Pt 1):474-8).

In one aspect, the invention provides methods for monitoring 20P2H8 gene products by determining the status of 20P2H8 gene products expressed by cells in a test tissue sample from an individual suspected of having a disease associated with dysregulated cell growth (such as hyperplasia or cancer) and then comparing the status so determined to the status of 20P2H8 gene products in a corresponding normal sample, the presence of aberrant 20P2H8 gene products in the test sample relative to the normal sample providing an indication of the presence of dysregulated cell growth within the cells of the individual.

In another aspect, the invention provides assays useful in determining the presence of cancer in an individual, comprising detecting a significant increase in 20P2H8 mRNA or protein expression in a test cell or tissue sample relative to expression levels in the corresponding normal cell or tissue. The presence of 20P2H8 mRNA may, for example, be evaluated in tissue samples including but not limited to prostate, kidney, bladder, cervical, skin, stomach, testicular, ovarian, breast, pancreas, colon and lung issues (see e.g. FIGS. 4-8). The presence of significant 20P2H8 expression in any of these tissues may be useful to indicate the emergence, presence and/or severity of these cancers, since the corresponding normal tissues do not express 20P2H8 mRNA or express it at lower levels.

In a related embodiment, 20P2H8 status may be determined at the protein level rather than at the nucleic acid level. For example, such a method or assay would comprise determining the level of 20P2H8 protein expressed by cells in a test tissue sample and comparing the level so determined to the level of 20P2H8 expressed in a corresponding normal sample. In one embodiment, the presence of 20P2H8 protein is evaluated, for example, using immunohistochemical methods. 20P2H8 antibodies or binding partners capable of detecting 20P2H8 protein expression may be used in a variety of assay formats well known in the art for this purpose.

In other related embodiments, one can evaluate the integrity 20P2H8 nucleotide and amino acid sequences in a biological sample in order to identify perturbations in the structure of these molecules such as insertions, deletions, substitutions and the like. Such embodiments are useful because perturbations in the nucleotide and amino acid sequences are observed in a large number of proteins associated with a growth dysregulated phenotype (see, e.g., Marrogi et al., 1999, J. Cutan. Pathol. 26 (8):369-378). In this context, a wide variety of assays for observing perturbations in nucleotide and amino acid sequences are well known in the art. For example, the size and structure of nucleic acid or amino acid sequences of 20P2H8 gene products may be observed by the Northern, Southern, Western, PCR and DNA sequencing protocols discussed herein. In addition, other methods for observing perturbations in nucleotide and amino acid sequences such as single strand conformation polymorphism analysis are well known in the art (see, e.g., U.S. Pat. Nos. 5,382,510 and 5,952,170).

In another embodiment, one can examine the methylation status of the 20P2H8 gene in a biological sample. Aberrant demethylation and/or hypermethylation of CpG islands in gene 5' regulatory regions frequently occurs in immortalized and transformed cells and can result in altered expression of various genes. For example, promoter hypermethylation of the pi-class glutathione S-transferase (a protein expressed in normal prostate but not expressed in >90% of prostate carcinomas) appears to permanently silence transcription of this gene and is the most frequently detected genomic alteration in prostate carcinomas (De Marzo et al., Am. J. Pathol. 155 (6): 1985-1992 (1999)). In addition, this alteration is present in at least 70% of cases of high-grade prostatic intraepithelial neoplasia (PIN) (Brooks et al, Cancer Epidemiol. Biomarkers Prev., 1998, 7:531-536). In another example, expression of the LAGE-I tumor specific gene (which is not expressed in normal prostate but is expressed in 25-50% of prostate cancers) is induced by deoxy-azacytidine in lymphoblastoid cells, suggesting that tumoral expression is due to demethylation (Lethe et al., Int. J. Cancer 76 (6): 903-908 (1998)). In this context, a variety of assays for examining methylation status of a gene are well known in the art. For example, one can utilize in Southern hybridization approaches methylation-sensitive restriction enzymes which can not cleave sequences that contain methylated CpG sites in order to assess the overall methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in Current Protocols In Molecular Biology, Units 12, Frederick M. Ausubul et al. eds., 1995.

Gene amplification provides an additional method of assessing the status of 20P2H8, a locus that maps to 15q22.32-23, a region shown to be perturbed in a variety of cancers. Gene amplification may be measured in a sample directly, for example, by conventional Southern blotting, Northern blotting to quantitate the transcription of mRNA (Thomas, 1980, Proc. Natl. Acad. Sci. USA, 77:5201-5205), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

In addition to the tissues discussed above, biopsied tissue or peripheral blood may be conveniently assayed for the presence of cancer cells, including but not limited to prostate, kidney, bladder, cervical, skin, stomach, testicular, ovarian, breast, pancreas, colon and lung cancers using for example, Northern, dot blot or RT-PCR analysis to detect 20P2H8 expression (see e.g. FIGS. 4-8). The presence of RT-PCR amplifiable 20P2H8 mRNA provides an indication of the presence of the cancer. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25:373-384; Ghossein et al., 1995, J. Clin. Oncol. 13:1195-2000; Heston et al., 1995, Clin. Chem. 41:1687-1688). RT-PCR assays are well known in the art.

A related aspect of the invention is directed to predicting susceptibility to developing cancer in an individual. In one embodiment, a method for predicting susceptibility to cancer comprises detecting 20P2H8 mRNA or 20P2H8 protein in a tissue sample, its presence indicating susceptibility to cancer, wherein the degree of 20P2H8 mRNA expression present is proportional to the degree of susceptibility. In a specific embodiment, the presence of 20P2H8 in prostate tissue is examined, with the presence of 20P2H8 in the sample providing an indication of prostate cancer susceptibility (or the emergence or existence of a prostate tumor). In another specific embodiment, the presence of 20P2H8 in tissue is examined, with the presence of 20P2H8 in the sample providing an indication of cancer susceptibility (or the emergence or existence of a tumor). In a closely related embodiment, one can evaluate the integrity 20P2H8 nucleotide and amino acid sequences in a biological sample in order to identify perturbations in the structure of these molecules such as insertions, deletions, substitutions and the like, with the presence of one or more perturbations in 20P2H8 gene products in the sample providing an indication of cancer susceptibility (or the emergence or existence of a tumor).

Yet another related aspect of the invention is directed to methods for gauging tumor aggressiveness. In one embodiment, a method for gauging aggressiveness of a tumor comprises determining the level of 20P2H8 mRNA or 20P2H8 protein expressed by cells in a sample of the tumor, comparing the level so determined to the level of 20P2H8 mRNA or 20P2H8 protein expressed in a corresponding normal tissue taken from the same individual or a normal tissue reference sample, wherein the degree of 20P2H8 mRNA or 20P2H8 protein expression in the tumor sample relative to the normal sample indicates the degree of aggressiveness. In a specific embodiment, aggressiveness of a tumor is evaluated by determining the extent to which 20P2H8 is expressed in the tumor cells, with higher expression levels indicating more aggressive tumors. In a closely related embodiment, one can evaluate the integrity of 20P2H8 nucleotide and amino acid sequences in a biological sample in order to identify perturbations in the structure of these molecules such as insertions, deletions, substitutions and the like, with the presence of one or more perturbations indicating more aggressive tumors.

Yet another related aspect of the invention is directed to methods for observing the progression of a malignancy in an individual over time. In one embodiment, methods for observing the progression of a malignancy in an individual over time comprise determining the level of 20P2H8 mRNA or 20P2H8 protein expressed by cells in a sample of the tumor, comparing the level so determined to the level of 20P2H8 mRNA or 20P2H8 protein expressed in an equivalent tissue sample taken from the same individual at a different time, wherein the degree of 20P2H8 mRNA or 20P2H8 protein expression in the tumor sample over time provides information on the progression of the cancer. In a specific embodiment, the progression of a cancer is evaluated by determining the extent to which 20P2H8 expression in the tumor cells alters over time, with higher expression levels indicating a progression of the cancer. In a closely related embodiment, one can evaluate the integrity 20P2H8 nucleotide and amino acid sequences in a biological sample in order to identify perturbations in the structure of these molecules such as insertions, deletions, substitutions and the like, with the presence of one or more perturbations indicating a progression of the cancer.

The above diagnostic approaches may be combined with any one of a wide variety of prognostic and diagnostic protocols known in the art. For example, another embodiment of the invention disclosed herein is directed to methods for observing a coincidence between the expression of 20P2H8 gene and 20P2H8 gene products (or perturbations in 20P2H8 gene and 20P2H8 gene products) and a factor that is associated with malignancy as a means of diagnosing and prognosticating the status of a tissue sample. In this context, a wide variety of factors associated with malignancy may be utilized such as the expression of genes otherwise associated with malignancy (including PSA, PSCA and PSM expression) as well as gross cytological observations (see e.g. Bocking et al., 1984, Anal. Quant. Cytol. 6 (2):74-88; Eptsein, 1995, Hum. Pathol. 26 (2):223-9; Thorson et al., 1998, Mod. Pathol. 11 (6):543-51; Baisden et al., 1999, Am. J. Surg. Pathol. 23 (8):918-24). Methods for observing a coincidence between the expression of 20P2H8 gene and 20P2H8 gene products (or perturbations in 20P2H8 gene and 20P2H8 gene products) and an additional factor that is associated with malignancy are useful, for example, because the presence of a set or constellation of specific factors that coincide provides information crucial for diagnosing and prognosticating the status of a tissue sample.

In a typical embodiment, methods for observing a coincidence between the expression of 20P2H8 gene and 20P2H8 gene products (or perturbations in 20P2H8 gene and 20P2H8 gene products) and a factor that is associated with malignancy entails detecting the overexpression of 20P2H8 mRNA or protein in a tissue sample, detecting the overexpression of PSA mRNA or protein in a tissue sample, and observing a coincidence of 20P2H8 mRNA or protein and PSA mRNA or protein overexpression. In a specific embodiment, the expression of 20P2H8 and PSA mRNA in prostate tissue is examined. In a preferred embodiment, the coincidence of 20P2H8 and PSA mRNA overexpression in the sample provides an indication of prostate cancer, prostate cancer susceptibility or the emergence or existence of a prostate tumor.

Methods for detecting and quantifying the expression of 20P2H8 mRNA or protein are described herein and use of standard nucleic acid and protein detection and quantification technologies is well known in the art. Standard methods for the detection and quantification of 20P2H8 mRNA include in situ hybridization using labeled 20P2H8 riboprobes, Northern blot and related techniques using 20P2H8 polynucleotide probes, RT-PCR analysis using primers specific for 20P2H8, and other amplification type detection methods, such as, for example, branched DNA, SISBA, TMA and the like. In a specific embodiment, semi-quantitative RT-PCR may be used to detect and quantify 20P2H8 mRNA expression as described in the Examples that follow. Any number of primers capable of amplifying 20P2H8 may be used for this purpose, including but not limited to the various primer sets specifically described herein. Standard methods for the detection and quantification of protein may be used for this purpose. In a specific embodiment, polyclonal or monoclonal antibodies specifically reactive with the wild-type 20P2H8 protein may be used in an immunohistochemical assay of biopsied tissue.

Identifying Molecules that Interact with 20P2H8

The 20P2H8 protein sequences disclosed herein allow the skilled artisan to identify proteins, small molecules and other agents that interact with 20P2H8 and pathways activated by 20P2H8 via any one of a variety of art accepted protocols. For example one can utilize one of the variety of so-called interaction trap systems (also referred to as the "two-hybrid assay"). In such systems, molecules that interact reconstitute a transcription factor and direct expression of a reporter gene, the expression of which is then assayed. Typical systems identify protein-protein interactions in vivo through reconstitution of a eukaryotic transcriptional activator and are disclosed for example in U.S. Pat. Nos. 5,955,280, 5,925,523, 5,846,722 and 6,004,746.

Alternatively one can identify molecules that interact with 20P2H8 protein sequences by screening peptide libraries. In such methods, peptides that bind to selected receptor molecules such as 20P2H8 are identified by screening libraries that encode a random or controlled collection of amino acids. Peptides encoded by the libraries are expressed as fusion proteins of bacteriophage coat proteins, and bacteriophage particles are then screened against the receptors of interest.

Peptides having a wide variety of uses, such as therapeutic or diagnostic reagents, may thus be identified without any prior information on the structure of the expected ligand or receptor molecule. Typical peptide libraries and screening methods that can be used to identify molecules that interact with 20P2H8 protein sequences are disclosed for example in U.S. Pat. Nos. 5,723,286 and 5,733,731.

Alternatively, cell lines expressing 20P2H8 can be used to identify protein-protein interactions mediated by 20P2H8. This possibility can be examined using immunoprecipitation techniques as shown by others (Hamilton B J, et al. Biochem. Biophys. Res. Commun. 1999, 261:646-51). Typically 20P2H8 protein can be immunoprecipitated from 20P2H8 expressing prostate cancer cell lines using anti-20P2H8 antibodies. Alternatively, antibodies against His-tag can be used in a cell line engineered to express 20P2H8 (vectors mentioned above). The immunoprecipitated complex can be examined for protein association by procedures such as western blotting, $^{35}$S-methionine labeling of proteins, protein microsequencing, silver staining and two dimensional gel electrophoresis.

Small molecules that interact with 20P2H8 can be identified through related embodiments of such screening assays. For example, small molecules can be identified that interfere with protein function, including molecules that interfere with 20P2H8's ability to mediate phosphorylation and de-phosphorylation, second messenger signaling and tumorigenesis. Typical methods are discussed for example in U.S. Pat. No. 5,928,868 and include methods for forming hybrid ligands in which at least one ligand is a small molecule. In an illustrative embodiment, the hybrid ligand is introduced into cells that in turn contain a first and a second expression vector. Each expression vector includes DNA for expressing a hybrid protein that encodes a target protein linked to a coding sequence for a transcriptional module. The cells further contains a reporter gene, the expression of which is conditioned on the proximity of the first and second hybrid proteins to each other, an event that occurs only if the hybrid ligand binds to target sites on both hybrid proteins. Those cells that express the reporter gene are selected and the unknown small molecule or the unknown hybrid protein is identified.

A typical embodiment of this invention consists of a method of screening for a molecule that interacts with a 20P2H8 amino acid sequence shown in FIG. 1 (SEQ ID NO: 2), comprising the steps of contacting a population of molecules with the 20P2H8 amino acid sequence, allowing the population of molecules and the 20P2H8 amino acid sequence to interact under conditions that facilitate an interaction, determining the presence of a molecule that interacts with the 20P2H8 amino acid sequence and then separating molecules that do not interact with the 20P2H8 amino acid sequence from molecules that do interact with the 20P2H8 amino acid sequence. In a specific embodiment, the method further includes purifying a molecule that interacts with the 20P2H8 amino acid sequence. In a preferred embodiment, the 20P2H8 amino acid sequence is contacted with a library of peptides.

Therapeutic Methods and Compositions

The identification of 20P2H8 as a gene that is highly expressed in cancers of the prostate (and possibly other cancers), opens a number of therapeutic approaches to the treatment of such cancers. As discussed above, it is possible that 20P2H8 is secreted from cancer cells and in this way modulates proliferation signals. Its potential role as a transcription factor and its high expression in prostate cancer makes it a potential target for small molecule-mediated therapy.

Accordingly, therapeutic approaches aimed at inhibiting the activity of the 20P2H8 protein are expected to be useful for patients suffering from prostate cancer, testicular cancer, and other cancers expressing 20P2H8. These therapeutic approaches aimed at inhibiting the activity of the 20P2H8 protein generally fall into two classes. One class comprises various methods for inhibiting the binding or association of the 20P2H8 protein with its binding partner or with other proteins. Another class comprises a variety of methods for inhibiting the transcription of the 20P2H8 gene or translation of 20P2H8 mRNA.

20P2H8 as a Target for Antibody-Based Therapy

The structural features of 20P2H8 indicate that this molecule is an attractive target for antibody-based therapeutic strategies. A number of typical antibody strategies are known in the art for targeting both extracellular and intracellular molecules (see e.g. complement and ADCC mediated killing as well as the use of intrabodies discussed below). Because 20P2H8 is expressed by cancer cells of various lineages and not by corresponding normal cells, systemic administration of 20P2H8-immunoreactive compositions would be expected to exhibit excellent sensitivity without toxic, non-specific and/or non-target effects caused by binding of the immunotherapeutic molecule to non-target organs and tissues. Antibodies specifically reactive with domains of 20P2H8 can be useful to treat 20P2H8-expressing cancers systemically, either as conjugates with a toxin or therapeutic agent, or as naked antibodies capable of inhibiting cell proliferation or function.

20P2H8 antibodies can be introduced into a patient such that the antibody binds to 20P2H8 and modulates or perturbs a function such as an interaction with a binding partner and consequently mediates the growth inhibition and/or destruction of the cells and the tumor and/or inhibits the growth of the cells or the tumor. Mechanisms by which such antibodies exert a therapeutic effect may include complement-mediated cytolysis, antibody-dependent cellular cytotoxicity, modulating the physiological function of 20P2H8, inhibiting ligand binding or signal transduction pathways, modulating tumor cell differentiation, altering tumor angiogenesis factor profiles, and/or by inducing apoptosis. 20P2H8 antibodies can be conjugated to toxic or therapeutic agents and used to deliver the toxic or therapeutic agent directly to 20P2H8-bearing tumor cells. Examples of toxic agents include, but are not limited to, calchemicin, maytansinoids, radioisotopes such as $^{131}$I, ytrium, and bismuth.

Cancer immunotherapy using anti-20P2H8 antibodies may follow the teachings generated from various approaches that have been successfully employed in the treatment of other types of cancer, including but not limited to colon cancer (Arlen et al., 1998, Crit. Rev. Immunol. 18:133-138), multiple myeloma (Ozaki et al., 1997, Blood 90:3179-3186; Tsunenari et al., 1997, Blood 90:2437-2444), gastric cancer (Kasprzyk et al., 1992, Cancer Res. 52:2771-2776), B-cell lymphoma (Funakoshi et al., 1996, J. Immunother. Emphasis Tumor Immunol. 19:93-101), leukemia (Zhong et al., 1996, Leuk. Res. 20:581-589), colorectal cancer (Moun et al., 1994, Cancer Res. 54:6160-6166; Velders et al., 1995, Cancer Res. 55:4398-4403), and breast cancer (Shepard et al., 1991, J. Clin. Immunol. 11:117-127). Some therapeutic approaches involve conjugation of naked antibody to a toxin, such as the conjugation of $^{131}$I to anti-CD20 antibodies (e.g., Rituxan™, IDEC Pharmaceuticals Corp.), while others involve co-administration of antibodies and other therapeutic agents, such as Herceptin™ (trastuzumab) with paclitaxel (Genentech, Inc.). For treatment of prostate cancer, for example, 20P2H8 antibodies can be administered in conjunction with radiation, chemotherapy or hormone ablation.

Although 20P2H8 antibody therapy may be useful for all stages of cancer, antibody therapy may be particularly appropriate in advanced or metastatic cancers. Treatment with the antibody therapy of the invention may be indicated for patients who have received previously one or more chemotherapy, while combining the antibody therapy of the invention with a chemotherapeutic or radiation regimen may be preferred for patients who have not received chemotherapeutic treatment. Additionally, antibody therapy may enable the use of reduced dosages of concomitant chemotherapy, particularly for patients who do not tolerate the toxicity of the chemotherapeutic agent very well.

It may be desirable for some cancer patients to be evaluated for the presence and level of 20P2H8 expression, preferably using immunohistochemical assessments of tumor tissue, quantitative 20P2H8 imaging, or other techniques capable of reliably indicating the presence and degree of 20P2H8 expression. Immunohistochemical analysis of tumor biopsies or surgical specimens may be preferred for this purpose. Methods for immunohistochemical analysis of tumor tissues are well known in the art.

Anti-20P2H8 monoclonal antibodies useful in treating prostate and other cancers include those that are capable of initiating a potent immune response against the tumor and those that are capable of direct cytotoxicity. In this regard, anti-20P2H8 monoclonal antibodies (mAbs) may elicit tumor cell lysis by either complement-mediated or antibody-dependent cell cytotoxicity (ADCC) mechanisms, both of which require an intact Fc portion of the immunoglobulin molecule for interaction with effector cell Fc receptor sites or complement proteins. In addition, anti-20P2H8 mAbs that exert a direct biological effect on tumor growth are useful in the practice of the invention. Potential mechanisms by which such directly cytotoxic mAbs may act include inhibition of cell growth, modulation of cellular differentiation, modulation of tumor angiogenesis factor profiles, and the induction of apoptosis. The mechanism by which a particular anti-20P2H8 mAb exerts an anti-tumor effect may be evaluated using any number of in vitro assays designed to determine ADCC, ADMMC, complement-mediated cell lysis, and so forth, as is generally known in the art.

The use of murine or other non-human monoclonal antibodies, or human/mouse chimeric mAbs may induce moderate to strong immune responses in some patients. In some cases, this will result in clearance of the antibody from circulation and reduced efficacy. In the most severe cases, such an immune response may lead to the extensive formation of immune complexes which, potentially, can cause renal failure. Accordingly, preferred monoclonal antibodies used in the practice of the therapeutic methods of the invention are those that are either fully human or humanized and that bind specifically to the target 20P2H8 antigen with high affinity but exhibit low or no antigenicity in the patient.

Therapeutic methods of the invention contemplate the administration of single anti-20P2H8 mAbs as well as combinations, or cocktails, of different mAbs. Such mAb cocktails may have certain advantages inasmuch as they contain mAbs that target different epitopes, exploit different effector mechanisms or combine directly cytotoxic mAbs with mAbs that rely on immune effector functionality. Such mAbs in combination may exhibit synergistic therapeutic effects. In addition, the administration of anti-20P2H8 mAbs may be combined with other therapeutic agents, including but not limited to various chemotherapeutic agents, androgen-blockers, and immune modulators (e.g., IL-2, GM-CSF). The anti-20P2H8 mAbs may be administered in their "naked" or unconjugated form, or may have therapeutic agents conjugated to them.

The anti-20P2H8 antibody formulations may be administered via any route capable of delivering the antibodies to the tumor site. Potentially effective routes of administration include, but are not limited to, intravenous, intraperitoneal, intramuscular, intratumor, intradermal, and the like. Treatment will generally involve the repeated administration of the anti-20P2H8 antibody preparation via an acceptable route of administration such as intravenous injection (IV), typically at a dose in the range of about 0.1 to about 10 mg/kg body weight. Doses in the range of 10-500 mg mAb per week may be effective and well tolerated.

Based on clinical experience with the Herceptin mAb in the treatment of metastatic breast cancer, an initial loading dose of approximately 4 mg/kg patient body weight IV followed by weekly doses of about 2 mg/kg IV of the anti-20P2H8 mAb preparation may represent an acceptable dosing regimen. Preferably, the initial loading dose is administered as a 90 minute or longer infusion. The periodic maintenance dose may be administered as a 30 minute or longer infusion, provided the initial dose was well tolerated. However, as one of skill in the art will understand, various factors will influence the ideal dose regimen in a particular case. Such factors may include, for example, the binding affinity and half life of the Ab or mAbs used, the degree of 20P2H8 expression in the patient, the extent of circulating shed 20P2H8 antigen, the desired steady-state antibody concentration level, frequency of treatment, and the influence of chemotherapeutic agents used in combination with the treatment method of the invention.

Optimally, patients should be evaluated for the level of circulating shed 20P2H8 antigen in serum in order to assist in the determination of the most effective dosing regimen and related factors. Such evaluations may also be used for monitoring purposes throughout therapy, and may be useful to gauge therapeutic success in combination with evaluating other parameters (such as serum PSA levels in prostate cancer therapy).

Inhibition of 20P2H8 Protein Function

The invention includes various methods and compositions for inhibiting the binding of 20P2H8 to its binding partner or ligand, or its association with other protein(s) as well as methods for inhibiting 20P2H8 function.

Inhibition of 20P2H8 with Intracellular Antibodies

In one approach, recombinant vectors encoding single chain antibodies that specifically bind to 20P2H8 may be introduced into 20P2H8 expressing cells via gene transfer technologies, wherein the encoded single chain anti-20P2H8 antibody is expressed intracellularly, binds to 20P2H8 protein, and thereby inhibits its function. Methods for engineering such intracellular single chain antibodies are well known. Such intracellular antibodies, also known as "intrabodies", may be specifically targeted to a particular compartment within the cell, providing control over where the inhibitory activity of the treatment will be focused. This technology has been successfully applied in the art (for review, see Richardson and Marasco, 1995, TIBTECH vol. 13). Intrabodies have been shown to virtually eliminate the expression of otherwise abundant cell surface receptors. See, for example, Richardson et al., 1995, Proc. Natl. Acad. Sci. USA 92: 3137-3141; Beerli et al., 1994, J. Biol. Chem. 289: 23931-23936; Deshane et al., 1994, Gene Ther. 1: 332-337.

Single chain antibodies comprise the variable domains of the heavy and light chain joined by a flexible linker polypeptide, and are expressed as a single polypeptide. Optionally, single chain antibodies may be expressed as a single chain variable region fragment joined to the light chain constant region. Well known intracellular trafficking signals may be engineered into recombinant polynucleotide vectors encoding such single chain antibodies in order to precisely target the expressed intrabody to the desired intracellular compartment. For example, intrabodies targeted to the endoplasmic reticulum (ER) may be engineered to incorporate a leader peptide and, optionally, a C-terminal ER retention signal, such as the KDEL amino acid motif. Intrabodies intended to exert activity in the nucleus may be engineered to include a nuclear localization signal. Lipid moieties may be joined to intrabodies in order to tether the intrabody to the cytosolic side of the plasma membrane. Intrabodies may also be targeted to exert function in the cytosol. For example, cytosolic intrabodies may be used to sequester factors within the cytosol, thereby preventing them from being transported to their natural cellular destination.

In one embodiment, intrabodies may be used to capture 20P2H8 in the nucleus, thereby preventing its activity within the nucleus. Nuclear targeting signals may be engineered into such 20P2H8 intrabodies in order to achieve the desired targeting. Such 20P2H8 intrabodies may be designed to bind specifically to a particular 20P2H8 domain. In another embodiment, cytosolic intrabodies that specifically bind to the 20P2H8 protein may be used to prevent 20P2H8 from gaining access to the nucleus, thereby preventing it from exerting any biological activity within the nucleus (e.g., preventing 20P2H8 from forming transcription complexes with other factors).

In order to specifically direct the expression of such intrabodies to particular tumor cells, the transcription of the intrabody may be placed under the regulatory control of an appropriate tumor-specific promoter and/or enhancer. In order to target intrabody expression specifically to prostate, for example, the PSA promoter and/or promoter/enhancer may be utilized (See, for example, U.S. Pat. No. 5,919,652).

Inhibition of 20P2H8 with Recombinant Proteins

In another approach, recombinant molecules that are capable of binding to 20P2H8 thereby preventing 20P2H8 from accessing/binding to its binding partner(s) or associating with other protein(s) are used to inhibit 20P2H8 function. Such recombinant molecules may, for example, contain the reactive part(s) of a 20P2H8 specific antibody molecule. In a particular embodiment, the 20P2H8 binding domain of a 20P2H8 binding partner may be engineered into a dimeric fusion protein comprising two 20P2H8 ligand binding domains linked to the Fc portion of a human IgG, such as human IgG1. Such IgG portion may contain, for example, the $C_H2$ and $C_H3$ domains and the hinge region, but not the $C_H1$ domain. Such dimeric fusion proteins may be administered in soluble form to patients suffering from a cancer associated with the expression of 20P2H8, including but not limited to prostate, bladder, testicular, ovarian, breast, pancreas, colon and lung cancers, where the dimeric fusion protein specifically binds to 20P2H8 thereby blocking 20P2H8 interaction with a binding partner. Such dimeric fusion proteins may be further combined into multimeric proteins using known antibody linking technologies.

Inhibition of 20P2H8 Transcription or Translation

Within another class of therapeutic approaches, the invention provides various methods and compositions for inhibiting the transcription of the 20P2H8 gene. Similarly, the invention also provides methods and compositions for inhibiting the translation of 20P2H8 mRNA into protein.

In one approach, a method of inhibiting the transcription of the 20P2H8 gene comprises contacting the 20P2H8 gene with a 20P2H8 antisense polynucleotide. In another approach, a method of inhibiting 20P2H8 mRNA translation comprises contacting the 20P2H8 mRNA with an antisense polynucleotide. In another approach, a 20P2H8 specific ribozyme may be used to cleave the 20P2H8 message, thereby inhibiting translation. Such antisense and ribozyme based methods may also be directed to the regulatory regions of the 20P2H8 gene, such as the 20P2H8 promoter and/or enhancer elements. Similarly, proteins capable of inhibiting a 20P2H8 gene transcription factor may be used to inhibit 20P2H8 mRNA transcription. The various polynucleotides and compositions useful in the aforementioned methods have been described above. The use of antisense and ribozyme molecules to inhibit transcription and translation is well known in the art.

Other factors that inhibit the transcription of 20P2H8 through interfering with 20P2H8 transcriptional activation may also be useful for the treatment of cancers expressing 20P2H8. Similarly, factors that are capable of interfering with 20P2H8 processing may be useful for the treatment of cancers expressing 20P2H8. Cancer treatment methods utilizing such factors are also within the scope of the invention.

General Considerations for Therapeutic Strategies

Gene transfer and gene therapy technologies may be used for delivering therapeutic polynucleotide molecules to tumor cells synthesizing 20P2H8 (i.e., antisense, ribozyme, polynucleotides encoding intrabodies and other 20P2H8 inhibitory molecules). A number of gene therapy approaches are known in the art. Recombinant vectors encoding 20P2H8 antisense polynucleotides, ribozymes, factors capable of interfering with 20P2H8 transcription, and so forth, may be delivered to target tumor cells using such gene therapy approaches.

The above therapeutic approaches may be combined with any one of a wide variety of chemotherapy or radiation therapy regimens. These therapeutic approaches may also enable the use of reduced dosages of chemotherapy and/or less frequent administration, particularly in patients that do not tolerate the toxicity of the chemotherapeutic agent well.

The anti-tumor activity of a particular composition (e.g., antisense, ribozyme, intrabody), or a combination of such compositions, may be evaluated using various in vitro and in vivo assay systems. In vitro assays for evaluating therapeutic potential include cell growth assays, soft agar assays and other assays indicative of tumor promoting activity, binding assays capable of determining the extent to which a therapeutic composition will inhibit the binding of 20P2H8 to a binding partner, etc.

In vivo, the effect of a 20P2H8 therapeutic composition may be evaluated in a suitable animal model. For example, xenogenic prostate cancer models wherein human prostate cancer explants or passaged xenograft tissues are introduced into immune compromised animals, such as nude or SCID mice, are appropriate in relation to prostate cancer and have been described (Klein et al., 1997, Nature Medicine 3:402-408). For example, PCT Patent Application WO98/16628, Sawyers et al., published Apr. 23, 1998, describes various xenograft models of human prostate cancer capable of recapitulating the development of primary tumors, micrometastasis, and the formation of osteoblastic metastases characteristic of late stage disease. Efficacy may be predicted using assays that measure inhibition of tumor formation, tumor regression or metastasis, and the like. See, also, the Examples below.

In vivo assays that qualify the promotion of apoptosis may also be useful in evaluating potential therapeutic compositions. In one embodiment, xenografts from bearing mice treated with the therapeutic composition may be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods may be formulated into pharmaceutical compositions comprising a carrier suitable for the desired delivery method. Suitable carriers include any material that when combined with the therapeutic composition retains the anti-tumor function of the therapeutic composition and is non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16$^{th}$ Ed., A. Osal., Ed., 1980).

Therapeutic formulations may be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations may be lyophilized and stored as sterile powders, preferably under vacuum, and then reconstituted in bacteriostatic water containing, for example, benzyl alcohol preservative, or in sterile water prior to injection.

Dosages and administration protocols for the treatment of cancers using the foregoing methods will vary with the method and the target cancer and will generally depend on a number of other factors appreciated in the art.

Cancer Vaccines

As noted above, the expression profile of 20P2H8 shows that it is highly expressed in advanced and metastasized prostate cancer. This expression pattern is reminiscent of the Cancer-Testis (CT) antigens or MAGEs, which are testis-specific genes that are up-regulated in melanomas and other cancers (Van den Eynde and Boon, Int J Clin Lab Res. 27:81-86, 1997). Due to their tissue-specific expression and high expression levels in cancer, the MAGEs are currently being investigated as targets for cancer vaccines (Durrant, Anticancer Drugs 8:727-733, 1997; Reynolds et al., Int J Cancer 72:972-976, 1997).

The invention further provides cancer vaccines comprising a 20P2H8 protein or fragment thereof, as well as DNA based vaccines. In view of the expression of 20P2H8 cancer vaccines are expected to be effective at specifically preventing and/or treating 20P2H8 expressing cancers without creating non-specific effects on non-target tissues. The use of a tumor antigen in a vaccine for generating humoral and cell-mediated immunity for use in anti-cancer therapy is well known in the art and has been employed in prostate cancer using human PSMA and rodent PAP immunogens (Hodge et al., 1995, Int. J. Cancer 63:231-237; Fong et al., 1997, J. Immunol. 159: 3113-3117). Such methods can be readily practiced by employing a 20P2H8 protein, or fragment thereof, or a 20P2H8-encoding nucleic acid molecule and recombinant vectors capable of expressing and appropriately presenting the 20P2H8 immunogen. An illustrative example of a typical technique consists of a method of generating an immune response (e.g. a humoral response) in a mammal comprising the steps exposing the mammal's immune system to an immunoreactive epitope (e.g. an epitope of the 20P2H8 protein shown in SEQ ID NO: 2) so that the mammal generates an immune response that is specific for that epitope is generated (e.g. antibodies that specifically recognize that epitope).

For example, viral gene delivery systems may be used to deliver a 20P2H8-encoding nucleic acid molecule. Various viral gene delivery systems that can be used in the practice of this aspect of the invention include, but are not limited to, vaccinia, fowlpox, canarypox, adenovirus, influenza, poliovirus, adeno-associated virus, lentivirus, and sindbus virus (Restifo, 1996, Curr. Opin. Immunol. 8:658-663). Non-viral delivery systems may also be employed by using naked DNA encoding a 20P2H8 protein or fragment thereof introduced into the patient (e.g., intramuscularly) to induce an anti-tumor response. In one embodiment, the full-length human 20P2H8 cDNA may be employed. In another embodiment, 20P2H8 nucleic acid molecules encoding specific cytotoxic T lymphocyte (CTL) epitopes may be employed. CTL epitopes can be determined using specific algorithms (e.g., Epimer, Brown University) to identify peptides within a 20P2H8 protein that are capable of optimally binding to specified HLA alleles.

Various ex vivo strategies may also be employed. One approach involves the use of dendritic cells to present 20P2H8 antigen to a patient's immune system. Dendritic cells express MHC class I and II, B7 co-stimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28:65-69; Murphy et al., 1996, Prostate 29:371-380). Dendritic cells can be used to present 20P2H8 peptides to T cells in the context of MHC class I and II molecules. In one embodiment, autologous dendritic cells are pulsed with 20P2H8 peptides capable of binding to MHC molecules. In another embodiment, dendritic cells are pulsed with the complete 20P2H8 protein. Yet another embodiment involves engineering the overexpression of the 20P2H8 gene in dendritic cells using various implementing vectors known in the art, such as adenovirus (Arthur et al., 1997, Cancer Gene Ther. 4:17-25), retrovirus (Henderson et al., 1996, Cancer Res. 56:3763-3770), lentivirus, adeno-associated virus, DNA transfection (Ribas et al., 1997, Cancer Res. 57:2865-2869), and tumor-derived RNA transfection (Ashley et al., 1997, J. Exp. Med. 186: 1177-1182). Cells expressing 20P2H8 may also be engineered to express immune modulators, such as GM-CSF, and used as immunizing agents.

Anti-idiotypic anti-20P2H8 antibodies can also be used in anti-cancer therapy as a vaccine for inducing an immune response to cells expressing a 20P2H8 protein. Specifically, the generation of anti-idiotypic antibodies is well known in the art and can readily be adapted to generate anti-idiotypic anti-20P2H8 antibodies that mimic an epitope on a 20P2H8 protein (see, for example, Wagner et al., 1997, Hybridoma 16: 33-40; Foon et al., 1995, J. Clin. Invest. 96:334-342; Herlyn et al., 1996, Cancer Immunol. Immunother. 43:65-76). Such an anti-idiotypic antibody can be used in cancer vaccine strategies.

Genetic immunization methods may be employed to generate prophylactic or therapeutic humoral and cellular immune responses directed against cancer cells expressing 20P2H8. Constructs comprising DNA encoding a 20P2H8 protein/immunogen and appropriate regulatory sequences may be injected directly into muscle or skin of an individual, such that the cells of the muscle or skin take-up the construct and express the encoded 20P2H8 protein/immunogen. Expression of the 20P2H8 protein immunogen results in the generation of prophylactic or therapeutic humoral and cellular immunity against bone, colon, pancreatic, testicular, cervical and ovarian cancers. Various prophylactic and therapeutic genetic immunization techniques known in the art may be used (for review, see information and references published at Internet address www.genweb.com).

Kits

For use in the diagnostic and therapeutic applications described or suggested above, kits are also provided by the invention. Such kits may comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be an antibody or polynucleotide specific for a 20P2H8 protein or a 20P2H8 gene or message, respectively. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

The kit of the invention will typically comprise the container described above and one or more other containers comprising materials desirable from a commercial and user standpoint, including buffers, diluents, filters, needles, syringes, and package inserts with instructions for use. A label may be present on the container to indicate that the composition is used for a specific therapy or non-therapeutic application, and may also indicate directions for either in vivo or in vitro use, such as those described above.

EXAMPLES

Various aspects of the invention are further described and illustrated by way of the several examples which follow, none of which are intended to limit the scope of the invention.

Example 1

SSH-Generated Isolation of cDNA Fragment of the 20P2H8 Gene Materials and Methods LAPC Xenografts and Human Tissues:

LAPC xenografts were obtained from Dr. Charles Sawyers (UCLA) and generated as described (Klein et al, 1997, Nature Med. 3: 402-408). Androgen dependent and independent LAPC-4 xenografts LAPC-4 AD and AI, respectively) and LAPC-9 AD and AI xenografts were grown in male SCID mice and were passaged as small tissue chunks in recipient males. LAPC-4 and -9 AI xenografts were derived from LAPC-4 or -9 AD tumors, respectively. Male mice bearing AD tumors were castrated and maintained for 2-3 months. After the tumors re-grew, the tumors were harvested and passaged in castrated males or in female SCID mice. Human tissues for RNA and protein analyses were obtained from the Human Tissue Resource Center (HTRC) at the UCLA (Los Angeles, Calif.) and from QualTek, Inc. (Santa Barbara, Calif.). A benign prostatic hyperplasia tissue sample was patient-derived.

Cell Lines:

Human cell lines (e.g., HeLa) were obtained from the ATCC and were maintained in DMEM with 5% fetal calf serum.

RNA Isolation:

Tumor tissue and cell lines were homogenized in Trizol reagent (Life Technologies, Gibco BRL) using 10 ml/g tissue or 10 ml/$10^8$ cells to isolate total RNA. Poly A RNA was purified from total RNA using Qiagen's Oligotex mRNA Mini and Midi kits. Total and mRNA were quantified by spectrophotometric analysis (O.D. 260/280 nm) and analyzed by gel electrophoresis.

```
Oligonucleotides:
The following HPLC purified oligonucleotides were
used.
DPNCDN (cDNA synthesis primer):
                                            (SEQ ID NO: 3)
5'TTTTGATCAAGCTT₃₀3'

Adaptor 1:
                                            (SEQ ID NO: 4)
5'CTAATACGACTCACTATAGGGCTCGAGCGGCCGCCCGGGCAG3'

(SEQ ID NO: 5)
3'GGCCCGTCCTAG5'

Adaptor 2:
                                            (SEQ ID NO: 6)
5'GTAATACGACTCACTATAGGGCAGCGTGGTCGCGGCCGAG3'

(SEQ ID NO: 7)
3'CGGCTCCTAG5'

PCR primer 1:
                                            (SEQ ID NO: 8)
5'CTAATACGACTCACTATAGGGC3'

Nested primer (NP)1:
                                            (SEQ ID NO: 9)
5'TCGAGCGGCCGCCCGGGCAGGA3'

Nested primer (NP)2:
                                            (SEQ ID NO: 10)
5'AGCGTGGTCGCGGCCGAGGA3'
```

Suppression Subtractive Hybridization:

Suppression Subtractive Hybridization (SSH) was used to identify cDNAs corresponding to genes which may be differentially expressed in prostate cancer. The SSH reaction utilized cDNA from an androgen-dependent human prostate cancer xenograft originally derived from a prostate cancer lymph node metastasis (LAPC-4 AD) and cDNA derived from human benign hyperplasia (BPH) prostate tissue, wherein the LAPC-4 AD xenograft was used as the source of the "tester" cDNA, and the BPH tissue was used as the source of the "driver" cDNA.

Double stranded cDNAs corresponding to tester and driver cDNAs were synthesized from 2 μg of poly(A)⁺ RNA isolated from the relevant xenograft tissue, as described above, using CLONTECH's PCR-Select cDNA Subtraction Kit and 1 ng of oligonucleotide DPNCDN as primer. First- and second-strand synthesis were carried out as described in the Kit's user manual protocol (CLONTECH Protocol No. PT1117-1, Catalog No. K1804-1). The resulting cDNA was digested with Dpn II for 3 hrs. at 37° C. Digested cDNA was extracted with phenol/chloroform (1:1) and ethanol precipitated.

Driver cDNA was generated by combining Dpn II digested cDNA from BPH with a mix of digested cDNAs derived from the human cell lines HeLa, 293, A431, Colo205, and mouse liver.

Tester cDNA was generated by diluting 1 μl of Dpn II digested cDNA from the relevant xenograft source (see above) (400 ng) in 5 μl of water. The diluted cDNA (2 μl, 160 ng) was then ligated to 2 μl of Adaptor 1 and Adaptor 2 (10 μM), in separate ligation reactions, in a total volume of 10 μl at 16° C. overnight, using 400 u of T4 DNA ligase (CLONTECH). Ligation was terminated with 1 μl of 0.2 M EDTA and heating at 72° C. for 5 min.

The first hybridization was performed by adding 1.5 μl (600 ng) of driver cDNA to each of two tubes containing 1.5

µl (20 ng) Adaptor 1- and Adaptor 2-ligated tester cDNA. In a final volume of 4 µl, the samples were overlaid with mineral oil, denatured in an MJ Research thermal cycler at 98° C. for 1.5 minutes, and then were allowed to hybridize for 8 hrs at 68° C. The two hybridizations were then mixed together with an additional 1 µl of fresh denatured driver cDNA and were allowed to hybridize overnight at 68° C. The second hybridization was then diluted in 200 µl of 20 mM Hepes, pH 8.3, 50 mM NaCl, 0.2 mM EDTA, heated at 70° C. for 7 min. and stored at −20° C.

PCR Amplification, Cloning and Sequencing of Gene Fragments Generated from SSH:

To amplify gene fragments resulting from SSH reactions, two PCR amplifications were performed. In the primary PCR reaction 1 µl of the diluted final hybridization mix was added to 1 µl of PCR primer 1 (10 µM), 0.5 µl dNTP mix (10 µM), 2.5 µl 10× reaction buffer (CLONTECH) and 0.5 µl 50× Advantage cDNA polymerase Mix (CLONTECH) in a final volume of 25 µl. PCR 1 was conducted using the following conditions: 75° C. for 5 min., 94° C. for 25 sec., then 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 µl from the pooled and diluted primary PCR reaction was added to the same reaction mix as used for PCR 1, except that primers NP1 and NP2 (10 µM) were used instead of PCR primer 1. PCR 2 was performed using 10-12 cycles of 94° C. for 10 sec, 68° C. for 30 sec, 72° C. for 1.5 minutes. The PCR products were analyzed using 2% agarose gel electrophoresis.

The PCR products were inserted into pCR2.1 using the T/A vector cloning kit (Invitrogen). Transformed *E. coli* were subjected to blue/white and ampicillin selection. White colonies were picked and arrayed into 96 well plates and were grown in liquid culture overnight. To identify inserts, PCR amplification was performed on 1 ml of bacterial culture using the conditions of PCR1 and NP1 and NP2 as primers. PCR products were analyzed using 2% agarose gel electrophoresis.

Bacterial clones were stored in 20% glycerol in a 96 well format. Plasmid DNA was prepared, sequenced, and subjected to nucleic acid homology searches of the GenBank, dBest, and NCI-CGAP databases.

RT-PCR Expression Analysis:

First strand cDNAs were generated from 1 µg of mRNA with oligo (dT) 12-18 priming using the Gibco-BRL Superscript Preamplification system. The manufacturers protocol was used and included an incubation for 50 min at 42° C. with reverse transcriptase followed by RNAse H treatment at 37° C. for 20 min. After completing the reaction, the volume was increased to 200 µl with water prior to normalization. First strand cDNAs from 16 different normal human tissues were obtained from Clontech.

Normalization of the first strand cDNAs from multiple tissues was performed by using the primers 5' atatcgccgcgctcgtcgtcgacaa3' (SEQ ID NO: 11) and 5' agccacacgcagctcattgtagaagg 3' (SEQ ID NO: 12) to amplify β-actin. First strand cDNA (5 µl) was amplified in a total volume of 50 µl containing 0.4 µM primers, 0.2 µM each dNTPs, 1×PCR buffer (Clontech, 10 mM Tris-HCL, 1.5 mM $MgCl_2$, 50 mM KCl, pH8.3) and 1× Klentaq DNA polymerase (Clontech). Five µl of the PCR reaction was removed at 18, 20, and 22 cycles and used for agarose gel electrophoresis. PCR was performed using an MJ Research thermal cycler under the following conditions: initial denaturation was at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the band intensities of the 283 bp β-actin bands from multiple tissues were compared by visual inspection. Dilution factors for the first strand cDNAs were calculated to result in equal β-actin band intensities in all tissues after 22 cycles of PCR. Three rounds of normalization were required to achieve equal band intensities in all tissues after 22 cycles of PCR.

To determine expression levels of the 20P2H8 gene, 5 µl of normalized first strand cDNA was analyzed by PCR using 25, 30, and 35 cycles of amplification using the following primer pairs:

```
                                        (SEQ ID NO: 13)
    5'- TCT GAA AAC CTC CAG ACA CAA GAA -3'

(SEQ ID NO: 14)
    5'- GGA GAT GGT AGA CAC TGG TGG AGT -3'
```

Semi quantitative expression analysis was achieved by comparing the PCR products at cycle numbers that give light band intensities.

Results:

The SSH experiment described in the Materials and Methods, supra, led to the isolation of numerous candidate gene fragment clones (SSH clones). All candidate clones were sequenced and subjected to homology analysis against all sequences in the major public gene and EST databases in order to provide information on the identity of the corresponding gene and to help guide the decision to analyze a particular gene for differential expression. In general, gene fragments which had no homology to any known sequence in any of the searched databases, and thus considered to represent novel genes, as well as gene fragments showing homology to previously sequenced expressed sequence tags (ESTs), were subjected to differential expression analysis by RT-PCR and/or Northern analysis.

An SHH clone of 442 bp exhibiting significant homology to ESTs derived from several libraries, including libraries made from fetal liver, placenta, and a pool of lung, testis and B cells was isolated and designated 20P2H8. Initial expression analysis by RT-PCR showed that 20P2H8 is expressed in prostate and all LAPC xenografts (FIG. 2). Additionally, RT-PCR analysis of first strand cDNA derived from 16 normal tissues showed expression primarily in prostate, pancreas, colon and placenta after 25 cycles of amplification (FIG. 2). Expression was detected in other tissues after 30 cycles of amplification (FIG. 2). This clone, therefore, was utilized for obtaining a full length cDNA encoding 20P2H8 as described in Example 2, below.

Example 2

Isolation of Full Length cDNA Encoding the 20P2H8 Gene

The isolated 20P2H8 gene fragment of 442 bp was used as a probe to identify the full length cDNA for 20P2H8 in a human prostate cDNA library. This resulted in the isolation of a 3600 bp cDNA, clone 20P2H8-GTC2, which encodes a 517 amino acid open reading frame with homology to heterogenous nuclear ribonucleoproteins (hnRNPs). The nucleotide and deduced amino acid sequences encoded by this cDNA are shown in FIG. 1. The highest homology is with a protein identified in *C. elegans* (CAA92704). Significant homology is also seen with hnRNPs involved in mRNA splicing (ROF, ROH1 and ROH2). 20P2H8 exhibits five RNA binding sequences, two corresponding to ribonucleoprotein-1

(RNP1) consensus sites and three corresponding to RNP2 sites (designated in FIG. 1). In addition, 20P2H8 contains three regions with significant proline content (30-42%), which lie outside regions of homology with hnRNPs (designated in FIG. 1).

Example 3

Northern Blot Analysis of 20P2H8 Gene Expression

Figure 3:
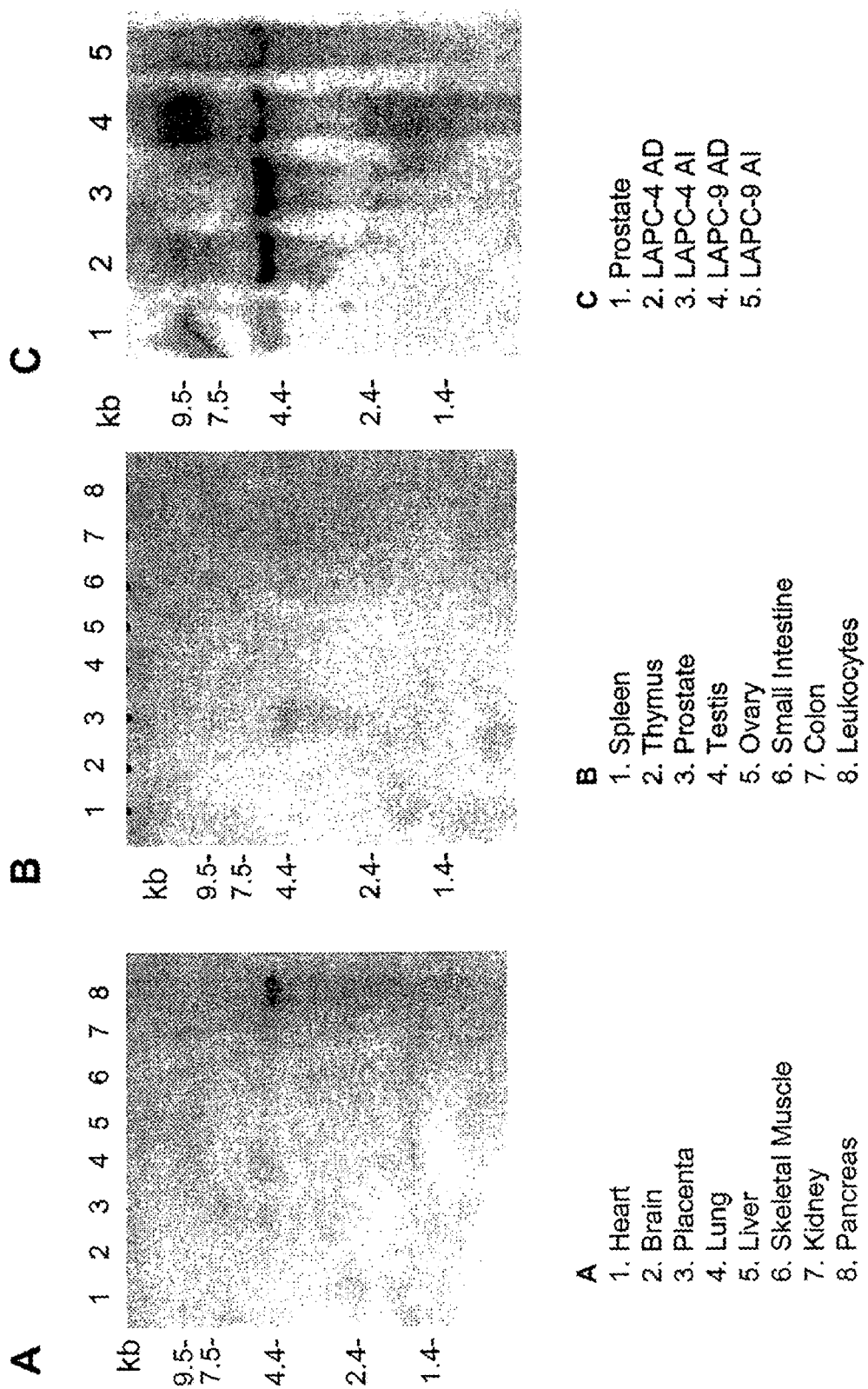
FIGS. 3A-3C show a Northern blot analysis of human 20P2H8 expression in various normal tissues showing predominant expression in pancreas with significant expression also detected in prostate and colon. Lanes 1-8 in panel A correspond to Northern analysis of 20P2H8 gene expression in heart, brain, placenta, lung, liver, skeletal muscle, kidney and pancreas respectively. Lanes 1-8 in panel B correspond to Northern analysis of 20P2H8 gene expression in spleen, thymus, prostate, testis, ovary, small intestine, colon and leukocytes respectively. Lanes 1-5 in panel C correspond to Northern analysis of 20P2H8 gene expression in prostate, LAPC-4 AD, LAPC-4 AI, LAPC-9AD and LAPC-9 AI respectively.

20P2H8 mRNA expression in normal human tissues was first analyzed by Northern blotting two multiple tissue blots obtained from Clontech (Palo Alto, Calif.), comprising a total of 16 different normal human tissues, using labeled 20P2H8 cDNA as a probe. RNA samples were quantitatively normalized with a β-actin probe. The results are shown in FIG. 3, Panels A and B, and indicate that, within the 16 tissues tested, the 20P2H8 gene is predominantly expressed as a single 4.4 kb transcript in pancreas, with lower level expression detected in prostate and colon, and lower level expression in placenta (FIG. 3; Panels A and B). No other normal tissues in the panel showed detectable expression.

In addition, in order to analyze 20P2H8 expression in human cancer tissues and cell lines, RNAs derived from LAPC human prostate cancer xenografts and several cancer cell lines were analyzed by Northern blot using the 20P2H8 cDNA as probe. All RNA samples were quantitatively normalized by ethidium bromide staining and subsequent analysis with a labeled β-actin probe. The results of this analysis are presented in FIG. 3, Panel C (LAPC xenografts) and FIG. 4 (colon and pancreatic cancer cell lines). The results show up-regulated expression of 20P2H8 in LAPC-9 and LAPC-4 xenografts compared to normal prostate, with highest levels detected in LAPC-4 AD and LAPC-4 AI (FIG. 3, Panel C) as well as high levels of expression in several pancreatic (BxPC-3, HPAC, Capan-1) and colon (CaCo-2, T84, Colo-205) cancer cell lines (FIG. 4), suggesting that 20P2H8 is a gene that is up-regulated in prostate, pancreatic and colon cancers.

Example 4

Production of Recombinant 20P2H8

To express recombinant 20P2H8 for use in a number of contexts such as analyzing the subcellular localization of 20P2H8 protein, a partial or the full length cDNA can cloned into any one of a variety of expression vectors such as those that provide a 6His tag at the carboxyl-terminus (e.g. pcDNA 3.1 myc-his, InVitrogen).

In a typical embodiment, an expression vectors construct with a 6His tag at the carboxyl-terminus is transfected into 293T cells which are then labeled for one hour with $^{35}$S-methionine. The cells are then washed and incubated in non-radioactive media to chase the labeled proteins for various time points. 20P2H8-His tagged protein is then immunoprecipitated using anti-His antibodies (Santa Cruz) from cell extracts and from cell supernatant (media) at various time points after the chase. The immunoprecipitates are analyzed by SDS-PAGE with subsequent autoradiography to visualize $^{35}$S-methionine labeled protein.

Additional embodiments of typical constructs are provided below.

Protein Expression

Figure 7:
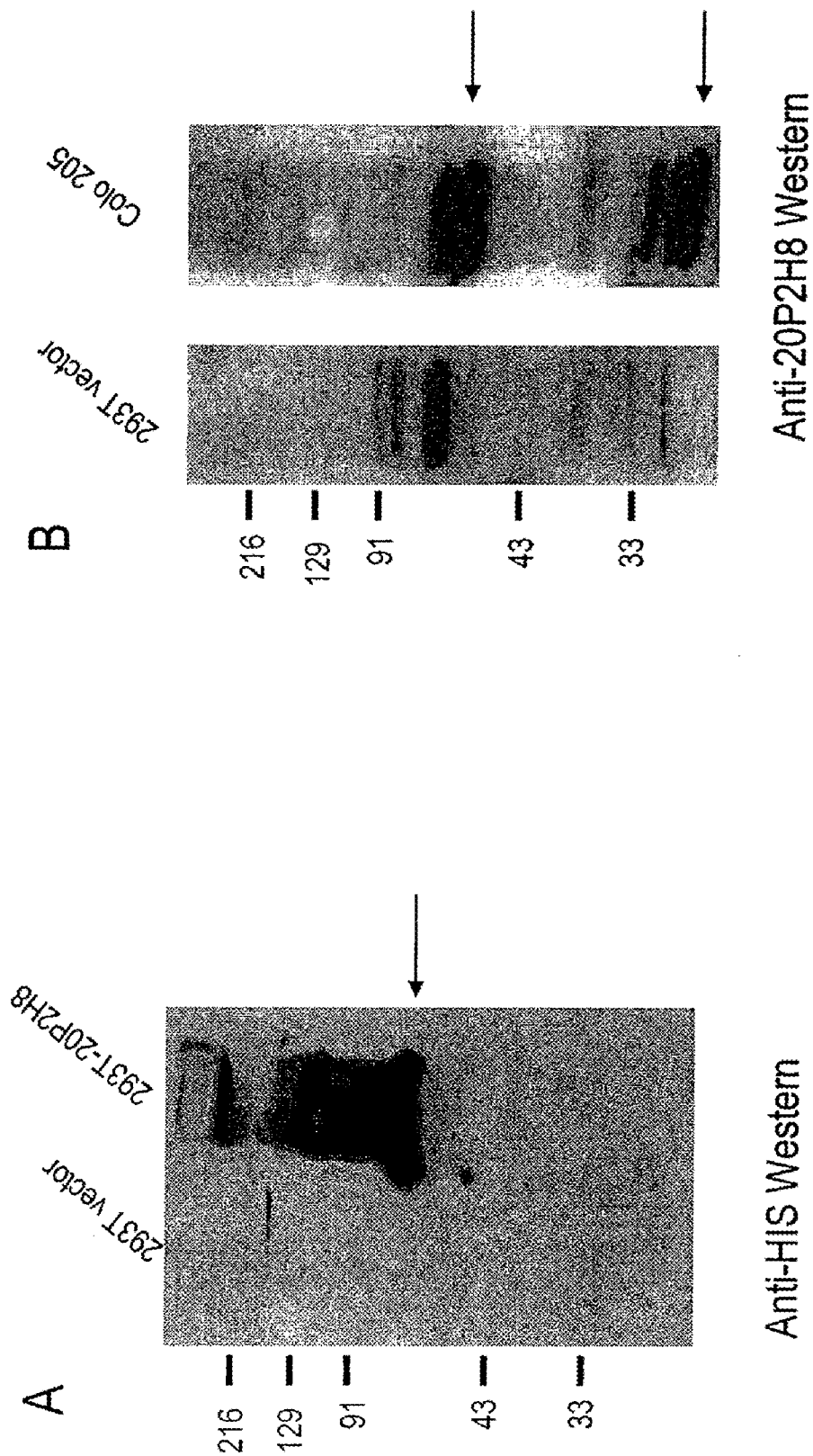
FIGS. 7A-7B show expression of recombinant 20P2H8 protein. A. 293T cells were transiently transfected with either pcDNA3.1 MycHis tagged 20P2H8 plasmid or with empty control vector and harvested 2 days later. Cells were lysed in SDS-PAGE sample buffer and lysates were separated on a 10-20% SDS-PAGE gel and then transferred to nitrocellulose. The blot was blocked in Tris-buffered saline (TBS)+2% non-fat milk and then probed with a 1:3,000 dilution of rabbit anti-His pAb (Santa Cruz Biotechnology Inc.) in TBS+0.15% Tween-20+1% milk. The blot was washed and then incubated with a 1:4,000 dilution of anti-rabbit HRP conjugate secondary antibody. Following washing, anti-His immunoreactive bands were developed by enhanced chemiluminescence and visualized by exposure to autoradiographic film. Indicated by arrow is a specific anti-His immunoreactive band of approximately 60 Kd that corresponds to expression of the Myc/His-tagged 20P2H8 protein in the transfected cells. B. Cell lysates of 20P2H8 mRNA negative 293T cells and of 20P2H8 mRNA positive Colo 205 cells were separated by SDS-PAGE and subjected to Western blot analysis as indicated above but using an anti-20P2H8 affinity purified polyclonal antibody (4 ug/ml). Indicated with arrows are anti-20P2H8 immunoreactive bands of approximately 58 kD and 30 kD that appear in 20P2H8 mRNA positive Colo 205 cells but not in 20P2H8 mRNA negative 293T cells.

In an illustrative embodiment describing the production of recombinant 20P2H8, 20P2H8 cDNA was cloned into the mammalian expression vector pcDNA 3.1 (Invitrogen) that contains a 6xHis COOH-terminal epitope tag that allows protein expression analysis using an anti-His pAb reagent. This construct was used to transfect 293T human embryonic kidney cells to assess 20P2H8 protein expression. As seen in FIG. 7 (panel A), an anti-His immunoreactive band of approximately 60 kD is seen in 293T cells transiently transfected with the 20P2H8 vector but not in cells transfected with a control empty vector. The molecular weight corresponds to the predicted 57 kD molecular weight of 20P2H8 cDNA plus the additional amino acids coded by the His and Myc epitope tags. Western analysis of Colo 205 cells, a 20P2H8 mRNA positive cell line, with an anti-20P2H8 polyclonal antibody demonstrates immunoreactive bands of approximately 58 kD and 30 kD that are not seen in 20P2H8 mRNA negative 293T cells, which is indicative of endogenous 20P2H8 protein expression (FIG. 7, panel B).

Additional constructs for recombinant expression are provided below.

pGEX Constructs

To express 20P2H8 in bacterial cells, a portion of 20P2H8 was fused to the Glutathione S-transferase (GST) gene by cloning into pGEX-6P-1 (Amersham Pharmacia Biotech, N.J.). All constructs were made to generate recombinant 20P2H8 protein sequences with GST fused at the N-terminus and a six histidine epitope at the C-terminus. The six histidine epitope tag was generated by adding the histidine codons to the cloning primer at the 3' end of the ORF. A PreScission™ recognition site permits cleavage of the GST tag from 20P2H8. The ampicillin resistance gene and pBR322 origin permits selection and maintenance of the plasmid in E. coli. In a specific illustrative embodiment, the following fragment of 20P2H8 was cloned into pGEX-6P-1: Amino acids 1 to 126 (SEQ ID NO: 2).

Additional constructs can be made in pGEX-6P-1 spanning any one of a variety of regions within the 20P2H8 protein including, for example a region containing one or more of the specified biological motifs discussed above or the following regions of the 20P2H8 protein: amino acids 1 to 517; amino acids 126 to 252 and; amino acids 252 to 517 (SEQ ID NO: 2).

pMAL Constructs

To express 20P2H8 in bacterial cells, portions of 20P2H8 can be fused to the maltose-binding protein (MBP) gene by cloning into pMAL-c2X and pMAL-p2X (New England Biolabs, Mass.). All constructs can be made to generate recombinant 20P2H8 protein sequences with MBP fused at the N-terminus and a six histidine epitope at the C-terminus. The six histidine epitope tag was generated by adding the histidine codons to the 3' cloning primer. A Factor Xa recognition site permits cleavage of the GST tag from 20P2H8. The pMAL-c2X and pMAL-p2X vectors are optimized to express the recombinant protein in the cytoplasm or periplasm respectively. Periplasm expression enhances folding of proteins with disulfide bonds. These constructs can be made in pMAL-c2X and pMAL-p2X and span the following regions of the 20P2H8 protein: amino acids 1 to 126; amino acids 1 to 517; amino acids 126 to 252; amino acids 252 to 517 (SEQ ID NO: 2).

pcDNA3.1/MycHis Construct

To express 20P2H8 in mammalian cells, the 1551 bp (517 amino acid) 20P2H8 ORF was cloned into pcDNA3.1/MycHis_Version A (Invitrogen, Carlsbad, Calif.). Protein expression is driven from the cytomegalovirus (CMV) promoter. The recombinant protein has the myc and six histidines fused to the C-terminus. The pcDNA3.1/MycHis vector also contains the bovine growth hormone (BGH) polyadenylation signal and transcription termination sequence to enhance mRNA stability along with the SV40 origin for episomal replication and simple vector rescue in cell lines expressing the large T antigen. The Neomycin resistance gene allows for selection of mammalian cells expressing the protein and the ampicillin resistance gene and ColE1 origin permits selection and maintenance of the plasmid in E. coli.

pSRa Constructs

To generate mammalian cell lines expressing 20P2H8 constitutively, the 1551 bp (517 amino acid) ORF was cloned into pSRa constructs. Amphotropic and ecotropic retroviruses are generated by transfection of pSRa constructs into the 293T-10A1 packaging line or co-transfection of pSRa and a helper plasmid (φ) in 293 cells, respectively. The retrovirus can be used to infect a variety of mammalian cell lines, resulting in the integration of the cloned gene, 20P2H8, into the host cell-lines. Protein expression is driven from a long terminal repeat (LTR). The Neomycin resistance gene allows for selection of mammalian cells expressing the protein and the ampicillin resistance gene and ColE1 origin permits selection and maintenance of the plasmid in E. coli. An additional pSRa construct was made that fused the FLAG tag to the C-terminus to allow detection using anti-FLAG antibodies. The FLAG sequence 5' gat tac aag gat gac gac gat aag 3' were added to cloning primer at the 3' end of the ORF.

Additional pSRa constructs can be made to produce both N-terminal and C-terminal GFP and myc/6 HIS fusion proteins of the full length 20P2H8 protein.

Example 5

Production of Recombinant 20P2H8 in a Baculovirus System

To generate recombinant 20P2H8 protein in a baculovirus expression system, 20P2H8 cDNA is cloned into the baculovirus transfer vector pBlueBac 4.5 (Invitrogen) which provides a His-tag at the N-terminus. Specifically, pBlueBac-20P2H8 is co-transfected with helper plasmid pBac-N-Blue (Invitrogen) into SF9 (Spodoptera frugiperda) insect cells to generate recombinant baculovirus (see Invitrogen instruction manual for details). Baculovirus is then collected from cell supernatant and purified by plaque assay.

Recombinant 20P2H8 protein is then generated by infection of HighFive insect cells (InVitrogen) with the purified baculovirus. Recombinant 20P2H8 protein may be detected using 20P2H8-specific antibody. 20P2H8 protein may be purified and used in various cell based assays or as immunogen to generate polyclonal and monoclonal antibodies specific for 20P2H8.

Example 6

Generation of 20P2H8 Antibodies

Generation of Monoclonal Antibodies (mAbs)

In a typical method of generating 20P2H8 monoclonal antibodies, a glutathione-S-transferase (GST) fusion protein encompassing the 20P2H8 protein is synthesized and used as immunogen. Balb C mice are initially immunized intraperitoneally with 200 μg of the GST-20P2H8 fusion protein mixed in complete Freund's adjuvant. Mice are subsequently immunized every 2 weeks with 75 μg of GST-20P2H8 protein mixed in Freund's incomplete adjuvant for a total of 3 immunizations. Reactivity of serum from immunized mice to full length 20P2H8 protein is monitored by ELISA using a partially purified preparation of HIS-tagged 20P2H8 protein expressed from 293T cells. Mice showing the strongest reactivity are rested for 3 weeks and given a final injection of fusion protein in PBS and then sacrificed 4 days later. The spleens of the sacrificed mice are then harvested and fused to SPO/2 myeloma cells using standard procedures (Harlow and Lane, 1988). Supernatants from growth wells following HAT selection are screened by ELISA and Western blot to identify 20P2H8 specific antibody producing clones.

The binding affinity of a 20P2H8 monoclonal antibody may be determined using standard technology. Affinity measurements quantify the strength of antibody to epitope binding and may be used to help define which 20P2H8 monoclonal antibodies are preferred for diagnostic or therapeutic use. The BIAcore system (Uppsala, Sweden) is a preferred method for determining binding affinity. The BIAcore system uses surface plasmon resonance (SPR, Welford K. 1991, Opt. Quant. Elect. 23:1; Morton and Myszka, 1998, Methods in Enzymology 295: 268) to monitor biomolecular interactions in real time. BIAcore analysis conveniently generates association rate constants, dissociation rate constants, equilibrium dissociation constants, and affinity constants.

Generation of Polyclonal Antibodies (pAbs)

To generate polyclonal sera to 20P2H8, a peptide was synthesized corresponding to amino acids 224-237 (QNAL-RKHKDLLGKR) of 20P2H8 protein sequence. The peptide was coupled to Keyhole limpet hemacyanin (KLH) and used to immunize a rabbit as follows. The rabbit was initially immunized with 200 ug of peptide-KLH mixed in complete Freund's adjuvant. The rabbit was then injected every two weeks with 200 ug of peptide-KLH in incomplete Freund's adjuvant. Bleeds were taken approximately 7-10 days following each immunization. ELISA and Western blotting analyses were used to determine specificity and titer of the rabbit serum to the immunizing peptide and the 20P2H8 protein respectively. Affinity purified 20P2H8 polyclonal antibodies were prepared by passage of crude serum from immunized rabbit over an affinity matrix comprised of 20P2H8 peptide covalently coupled to Affigel 10 (BioRad). After extensive washing of the matrix with PBS, antibodies specific to 20P2H8 peptide were eluted with low pH glycine buffer (0.1M, pH 2.5). Western blotting reveals the appearance of novel anti-20P2H8 immunoreactive bands of approximately 58 kD and 30 kD in 20P2H8 mRNA-expressing COLO 205 cells but not in 20P2H8 mRNA-negative 293T cells (FIG. 7, panel B).

Example 7

Identification of Potential Signal Transduction Pathways

To determine whether 20P2H8 directly or indirectly activates known signal transduction pathways in cells, luciferase (luc) based transcriptional reporter assays are carried out in cells expressing 20P2H8. These transcriptional reporters contain consensus binding sites for known transcription factors which lie downstream of well characterized signal transduction pathways. The reporters and examples of there associated transcription factors, signal transduction pathways, and activation stimuli are listed below.

1. NFkB-luc, NFkB/Rel; Ik-kinase/SAPK; growth/apoptosis/stress
2. SRE-luc, SRF/TCF/ELK1; MAPK/SAPK; growth/differentiation
3. AP-1-luc, FOS/JUN; MAPK/SAPK/PKC; growth/apoptosis/stress
4. ARE-luc, androgen receptor; steroids/MAPK; growth/differentiation/apoptosis
5. p53-luc, p53; SAPK; growth/differentiation/apoptosis
6. CRE-luc, CREB/ATF2; PKA/p38; growth/apoptosis/stress 20P2H8-mediated effects may be assayed in cells showing mRNA expression, such as the 20P2H8-expressing cancer cell lines shown in FIG. 4. Luciferase reporter plasmids may be introduced by lipid mediated transfection (TFX-50, Promega). Luciferase activity, an indicator of relative transcriptional activity, is measured by incubation of cells extracts with luciferin substrate and luminescence of the reaction is monitored in a luminometer.

The transcriptional activity of 20P2H8 may be confirmed using electromobility shift assays (EMSA). Cells expressing 20P2H8 will be evaluated for their ability to bind known response elements and compared to control 20P2H8 negative cells. Whole cell and nuclear extracts will be used in this assay, and will be analyzed in the presence and absence of potential (i) 20P2H8 inhibitors and (ii) 20P2H8 interacting proteins. These assays will provide us with valuable information regarding gene candidates and biologic pathways regulated by 20P2H8 and the mechanism by which 20P2H8 controls gene expression.

Example 8

In Vitro Assays for Characterizing 20P2H8

Subcellular Localization of 20P2H8. Sequence analysis of 20P2H8 revealed the presence of RNP like domains and suggests that 20P2H8 may have an RNA splicing function. This, in turn, indicates that 20P2H8 may have a nuclear localization. The cellular location of 20P2H8 can be assessed using subcellular fractionation techniques widely used in cellular biology (Storrie B, et al. Methods Enzymol. 1990; 182: 203-25). Prostate, colon or pancreatic cells can be lysed and separated into nuclear, cytosolic and membrane fractions. The expression of 20P2H8 in the different fractions can be tested using western blotting techniques.

Example 9

In Vitro Assays Of 20P2H8 Function. 20P2H8 function can be assessed in mammalian cells using in vitro approaches. For mammalian expression, 20P2H8 can be cloned into a number of appropriate vectors, including pcDNA 3.1 myc-His-tag and the retroviral vector pSRαtkneo (Muller et al., 1991, MCB 11:1785). Using such expression vectors, 20P2H8 can be expressed in several cancer cell lines, including for example PC-3, NIH 3T3, LNCaP and 293T. Expression of 20P2H8 can be monitored using anti-20P2H8 antibodies.

Mammalian cell lines expressing 20P2H8 can be tested in several in vitro and in vivo assays, including cell proliferation in tissue culture, activation of apoptotic signals, primary and metastatic tumor formation in SCID mice, and in vitro invasion using a membrane invasion culture system (MICS) (Welch et al., Int. J. Cancer 43: 449-457). 20P2H8 cell phenotype is compared to the phenotype of cells that lack expression of 20P2H8.

Cell lines expressing 20P2H8 can also be assayed for alteration of invasive and migratory properties by measuring passage of cells through a matrigel coated porous membrane chamber (Becton Dickinson). Passage of cells through the membrane to the opposite side is monitored using a fluorescent assay (Becton Dickinson Technical Bulletin #428) using calcein-Am (Molecular Probes) loaded indicator cells. Cell lines analyzed include parental and 20P2H8 overexpressing PC3, 3T3 and LNCaP cells. To assay whether 20P2H8 has chemoattractant properties, parental indicator cells are monitored for passage through the porous membrane toward a gradient of 20P2H8 conditioned media compared to control media. This assay may also be used to qualify and quantify specific neutralization of the 20P2H8 induced effect by candidate cancer therapeutic compositions.

The function of 20P2H8 can be evaluated using anti-sense RNA technology coupled to the various functional assays described within this section, e.g. growth, invasion and migration. Anti-sense RNA oligonucleotides can be introduced into 20P2H8 expressing cells, thereby preventing the expression of 20P2H8. Control and anti-sense containing cells can be analyzed for proliferation, invasion, migration, apoptotic and transcriptional potential. The local as well as systemic effect of the loss of 20P2H8 expression can be evaluated. In addition to confirming the function of 20P2H8, anti-sense oligonucleotides may be used as a therapeutic agent.

Example 10

In Vivo Assay for 20P2H8 Tumor Growth Promotion

The effect of the 20P2H8 protein on tumor cell growth may be evaluated in vivo by gene overexpression in tumor-bearing mice. For example, SCID mice can be injected SQ on each flank with $1 \times 10^6$ of a number of prostate, colon or pancreatic cell lines containing tkNeo empty vector or 20P2H8. At least two strategies may be used: (1) Constitutive 20P2H8 expression under regulation of an LTR promoter, and (2) Regulated expression under control of an inducible vector system, such as ecdysone, tet, etc. Tumor volume is then monitored at the appearance of palpable tumors and followed over time to determine if 20P2H8 expressing cells grow at a faster rate. Additionally, mice may be implanted with $1 \times 10^5$ of the same cells orthotopically to determine if 20P2H8 has an effect on local growth in the target tissue (i.e., prostate) or on the ability of the cells to metastasize, specifically to lungs, lymph nodes, liver, bone marrow, etc. In relation to prostate cancer, the effect of 20P2H8 on bone tumor formation and growth may be assessed by injecting prostate tumor cells intratibially, as described in WO98/16628.

These assays are also useful to determine the 20P2H8 inhibitory effect of candidate therapeutic compositions, such as for example, 20P2H8 antibodies, 20P2H8 antisense molecules and ribozymes.

Example 11

In Vitro Assay of 20P2H8 Protein Interaction

Cell lines expressing 20P2H8 can also be used to identify protein-protein interactions mediated by 20P2H8. The presence of proline-rich regions and homology to RNP in the ORF suggest that 20P2H8 may interact with other RNPs. This possibility can be examined using immunoprecipitation techniques as shown by others (Hamilton B J, et al. Biochem. Biophys. Res. Commun. 1999, 261:646-51). 20P2H8 protein can be immunoprecipitated from 20P2H8 expressing prostate cancer cell lines and examined for protein association by western blotting. Protein interaction may be also studied by a two yeast hybrid system, as described by Shnyreva et. Al. (Shnyreva M et al, J Biol. Chem. 2000. 19; 275; 15498-503). These assays may also be used to analyze the effect of potential cancer therapeutics on 20P2H8 function.

To determine the contribution of the various domains contained within the 20P2H8 ORF to 20P2H8 function, 20P2H8 mutants can be generated lacking one or more domains. Cell lines expressing mutant 20P2H8 protein will be evaluated for alteration in proliferation, invasion, migration, transcriptional activation and protein-protein interaction.

Example 12

Chromosomal Localization of 20P2H8

The chromosomal localization of 20P2H8 was determined using the GeneBridge4 radiation hybrid panel (Walter et al., 1994, Nat. Genetics 7:22) (Research Genetics, Huntsville Ala.). The following PCR primers were used to localize 20P2H8:

```
20P2H8.5  tcttgaaacctccagacacaagaa    (SEQ ID NO: 15)
20P2H8.6  aagttacgatttggcttcactgg     (SEQ ID NO: 16)
```

The resulting mapping vector for the 93 radiation hybrid panel DNAs was:

```
000000100100101000020000110100000001010010101111000
10000101011010000210111000000001101010000001
```

This the mapping program which can be found at internet address http://www-genome.wi.mit.edu/cgi-bin/contig/rhmapper.pl maps 85P1B3 to chromosome 8q22.2-23.1/15q22.32-23. As HTGS hits show PACs on chromosome 15 therefore this is the most likely mapping location.

Throughout this application, various publications are referenced. The disclosures of these publications are hereby incorporated by reference herein in their entireties.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLES

TABLE 1

| Rank | Start Position | Subsequence | Residue Listing | Score (Estimate of half time of disassociation) |
|---|---|---|---|---|
| 1 | 304 | FLGEFATDI | (SEQ ID NO: 17) | 747.7 |
| 2 | 215 | VLFACEEYA | (SEQ ID NO: 18) | 84.2 |
| 3 | 233 | LLGKRYIEL | (SEQ ID NO: 19) | 54.5 |
| 4 | 275 | QQFVPPTNV | (SEQ ID NO: 20) | 26.1 |
| 5 | 363 | CSAEEMNFV | (SEQ ID NO: 21) | 23.6 |
| 6 | 159 | FLSKENQVI | (SEQ ID NO: 22) | 19.7 |
| 7 | 450 | SLGYFPTAA | (SEQ ID NO: 23) | 18.9 |
| 8 | 509 | TLPKEWVCI | (SEQ ID NO: 24) | 17.7 |
| 9 | 393 | YTFPAPAAV | (SEQ ID NO: 25) | 16.4 |
| 10 | 492 | YQYATEDGL | (SEQ ID NO: 26) | 15.6 |

The invention claimed is:

1. A method of expressing a polypeptide, comprising:
   providing a host cell which comprises an expression vector comprising a polynucleotide sequence of SEQ ID NO: 1, which encodes the polypeptide of SEQ ID NO: 2; and
   culturing the host cell under conditions wherein the polypeptide is expressed.

2. The method of claim 1, further comprising recovering the polypeptide.

3. The method of claim 1, wherein the host cell is a eucaryotic cell.

4. The method of claim 3, wherein the eucaryotic cell is a Chinese Hamster Ovary cell.

5. The method of claim 3, wherein the eucaryotic cell is a yeast cell.

6. The method of claim 3, wherein the eucaryotic cell is a plant cell.

7. The method of claim 1, wherein the host cell is a prokaryotic cell.

8. The method of claim 7, wherein the prokaryotic cell is a bacterial cell.

9. The method of claim 8, wherein the bacterial cell is an *E. coli* cell.

* * * * *

SEQUENCE LISTING

```
<160> NUMBER OF SEQ ID NOS: 26

<210> SEQ ID NO 1
<211> LENGTH: 3585
<212> TYPE: DNA
<213> ORGANISM: Homo Sapiens

<400> SEQUENCE: 1 cttttggga tcactgctgg ggccaccggg gccaagctag gctcggatga gaaggagttg      60
atcctgctgt tctggaaagt cgtggatctg gccaacaaga aggtgggaca gttgcacgaa    120
gtgctagtta gaccggatca gttggaactg acggaggact gcaaagaaga aactaaaata    180
gacgtcgaaa gcctgtcctc ggcgtcgcag ctggaccaag ccctccgaca gtttaaccag    240
tcagtgagca atgaactgaa tattggagta gggacttcct tctgtctctg tactgatggg    300
cagcttcatg tcaggcaaat cctgcatcct gaggcttcca agaagaatgt actattacct    360
gaatgcttct attccttttt tgatcttcga aaagaattca agaaatgttg ccctggttca    420
cctgatattg acaaactgga cgttgccaca atgacagagt atttaaattt tgagaagagt    480
```

```
agttcagtct ctcgatatgg agcctctcaa gttgaagata tggggaatat aattttagca      540
atgatttcag agccttataa tcacaggttt tcagatccag agagagtgaa ttacaagttt      600
gaaagtggaa cttgcagcaa gatggaactt attgatgata caccgtagt cagggcacga       660 ggtttaccat ggcagtcttc agatcaagat attgcaagat tcttcaaagg actcaatatt      720
gccaagggag gtgcagcact tgtctgaat gctcagggtc gaaggaacgg agaagctctg       780
gttaggtttg taagtgagga gcaccgagac ctagcactac agaggcacaa acatcacatg      840
gggacccggt atattgaggt ttacaaagca acaggtgaag atttccttaa aattgctggt      900
ggtacttcca atgaggtagc ccagtttctc tccaaggaaa atcaagtcat tgttcgcatg      960
cgggggctcc ctttcacggc cacagctgaa gaagtggtgg ccttctttgg acagcattgc     1020
cctattactg ggggaaagga aggcatcctc tttgtcacct acccagatgg taggccaaca     1080
ggggacgctt ttgtcctctt tgcctgtgag aatatgcac agaatgcgtt gaggaagcat      1140
aaagacttgt tgggtaaaag atacattgaa ctcttcagga gcacagcagc tgaagttcag     1200
caggtgctga atcgattctc ctcggcccct ctcattccac ttccaacccc tcccattatt     1260
ccagtactac ctcagcaatt tgtgcccct acaaatgtta gagactgtat acgccttcga      1320
ggtcttccct atgcagccac aattgaggac atcctggatt tcctggggga gttcgccaca     1380
gatattcgta ctcatggggt tcacatggtt ttgaatcacc agggccgccc atcaggagat     1440
gcctttatcc agatgaagtc tgcggacaga gcatttatgg ctgcacagaa gtgtcataaa     1500
aaaaacatga aggacagata tgttgaagtc tttcagtgtt cagctgagga gatgaacttt     1560
gtgttaatgg ggggcacttt aaatcgaaat ggcttatccc caccgccatg cctgtctcct     1620
ccctcctaca catttccagc tcctgctgca gttattccta cagaagctgc catttaccag     1680
ccctctgtga ttttgaatcc acgagcactg cagccctcca cagcgtacta cccagcaggc     1740
actcagctct tcatgaacta cacagcgtac tatcccagcc cccaggttc gcctaatagt      1800 cttggctact tccctacagc tgctaatctt agcggtgtcc ctccacagcc tggcacggtg     1860
gtcagaatgc agggcctggc ctacaatact ggagttaagg aaattcttaa cttcttccaa     1920
ggttaccagt atgcaaccga ggatggactt atacacacaa atgaccaggc caggactcta     1980
cccaaagaat gggtttgtat ttaagggccc cagcagttag aacatcctca gaaagaagt     2040 gtttgaaaga tgtatggtga tcttgaaacc tccagacaca agaaaacttc tagcaaattc     2100 agggaagtt tgtctacact caggctgcag tattttcagc aaacttgatt ggacaaacgg      2160
gcctgtgcct tatctttggg tggagtgaaa aaatttgagc tagtgaagcc aaatcgtaac     2220
ttacagcaag cagcatgcag catacctggc tctttgctga ttgcaaatag gcatttaaaa     2280
tgtgaatttg gaatcagatg tctccattac ttccagttaa agtggcatca taggtgtttc     2340 ctaagttta agtcttggat aaaaactcca ccagtgtcta ccatctccac catgaactct     2400
gttaaggaag cttcattttt gtatattccc gctcttttct cttcatttcc ctgtcttctg     2460
cataatcatg ccttcttgct aagtaattca agcataagat cttggaataa taaaatcaca     2520
atcttaggag aaagaataaa attgttattt tcccagtctc ttggccatga tgatatctta     2580
tgattaaaaa caaattaaat tttaaaacac ctgaagataa attagaagaa attgtgcacc     2640
ctccacaaaa catacaaagt ttaaaagttt ggatcttttt ctcagcaggt atcagttgta     2700
aataatgaat taggggccaa aatgcaaaac gaaaaatgaa gcagctacat gtagttagta     2760
atttctagtt tgaactgtaa ttgaatattg tggcttcata tgtattattt tatattgtac     2820
```

-continued

```
tttttttcatt attgatggtt tggactttaa taagagaaat tccatagttt ttaatatccc    2880
agaagtgaga caatttgaac agtgtattct agaaaacaat acactaactg aacagaagtg    2940
aatgcttata tatattatga tagcctaaaa cctttttcct ctaatgcctt aactgtcaaa    3000
taattataac cttttaaagc ataggactat agtcagcatg ctagactgag aggtaaacac    3060
tgatgcaatt agaacaggta ctgatgctgt cagtgtttaa cactatgttt agctgtgttt    3120
atgctataaa agtgcaatat tagacactag ctagtactgc tgcctcatgt aactccaaag    3180
aaaacaggat tcattaagt gcattgaatg tggatatttc tctaagttac tcatattgtc     3240
ctttgcttga atgcaatgcc gtgcagattt atgaggctgc tattttttatt ttctgtgcat   3300 tactttaaca ccttaaaggg agaagcaaac atttccttct tcagctgact ggcaatggcc    3360
ctttaactgc aataggaaga aaaaaaaaaa ggtttgtgtg aaaattggtg ataactggca    3420
cttaagatcg aaaagaaatt tctgtatact tgatgcctta agatgcccaa agctgcccaa    3480
agctctgaaa gactttaaga taggcagtaa tgcttactac aatactactg agttttttgta  3540 gagttaacat ttgataataa aacttgcctg tttaatctca aaaaa                    3585
```

<210> SEQ ID NO 2
<211> LENGTH: 517
<212> TYPE: PRT
<213> ORGANISM: Homo Sapiens

<400> SEQUENCE: 2

```
Met Thr Glu Tyr Leu Asn Phe Glu Lys Ser Ser Val Ser Arg Tyr
  1               5                  10                  15

Gly Ala Ser Gln Val Glu Asp Met Gly Asn Ile Ile Leu Ala Met Ile
                 20                  25                  30

Ser Glu Pro Tyr Asn His Arg Phe Ser Asp Pro Glu Arg Val Asn Tyr
             35                  40                  45

Lys Phe Glu Ser Gly Thr Cys Ser Lys Met Glu Leu Ile Asp Asp Asn
         50                  55                  60

Thr Val Val Arg Ala Arg Gly Leu Pro Trp Gln Ser Ser Asp Gln Asp
65                  70                  75                  80

Ile Ala Arg Phe Phe Lys Gly Leu Asn Ile Ala Lys Gly Gly Ala Ala
                 85                  90                  95

Leu Cys Leu Asn Ala Gln Gly Arg Arg Asn Gly Glu Ala Leu Val Arg
                100                 105                 110

Phe Val Ser Glu Glu His Arg Asp Leu Ala Leu Gln Arg His Lys His
            115                 120                 125

His Met Gly Thr Arg Tyr Ile Glu Val Tyr Lys Ala Thr Gly Glu Asp
        130                 135                 140

Phe Leu Lys Ile Ala Gly Gly Thr Ser Asn Glu Val Ala Gln Phe Leu
145                 150                 155                 160

Ser Lys Glu Asn Gln Val Ile Val Arg Met Arg Gly Leu Pro Phe Thr
                165                 170                 175

Ala Thr Ala Glu Glu Val Val Ala Phe Phe Gly Gln His Cys Pro Ile
            180                 185                 190

Thr Gly Gly Lys Glu Gly Ile Leu Phe Val Thr Tyr Pro Asp Gly Arg
        195                 200                 205

Pro Thr Gly Asp Ala Phe Val Leu Phe Ala Cys Glu Glu Tyr Ala Gln
    210                 215                 220

Asn Ala Leu Arg Lys His Lys Asp Leu Leu Gly Lys Arg Tyr Ile Glu
225                 230                 235                 240
```

```
Leu Phe Arg Ser Thr Ala Ala Glu Val Gln Gln Val Leu Asn Arg Phe
            245                 250                 255

Ser Ser Ala Pro Leu Ile Pro Leu Pro Thr Pro Ile Ile Pro Val
        260                 265                 270

Leu Pro Gln Gln Phe Val Pro Pro Thr Asn Val Arg Asp Cys Ile Arg
            275                 280                 285

Leu Arg Gly Leu Pro Tyr Ala Ala Thr Ile Glu Asp Ile Leu Asp Phe
        290                 295                 300

Leu Gly Glu Phe Ala Thr Asp Ile Arg Thr His Gly Val His Met Val
305                 310                 315                 320

Leu Asn His Gln Gly Arg Pro Ser Gly Asp Ala Phe Ile Gln Met Lys
            325                 330                 335

Ser Ala Asp Arg Ala Phe Met Ala Ala Gln Lys Cys His Lys Lys Asn
        340                 345                 350

Met Lys Asp Arg Tyr Val Glu Val Phe Gln Cys Ser Ala Glu Glu Met
            355                 360                 365

Asn Phe Val Leu Met Gly Gly Thr Leu Asn Arg Asn Gly Leu Ser Pro
        370                 375                 380

Pro Pro Cys Leu Ser Pro Pro Ser Tyr Thr Phe Pro Ala Pro Ala Ala
385                 390                 395                 400

Val Ile Pro Thr Glu Ala Ala Ile Tyr Gln Pro Ser Val Ile Leu Asn
            405                 410                 415

Pro Arg Ala Leu Gln Pro Ser Thr Ala Tyr Tyr Pro Ala Gly Thr Gln
        420                 425                 430

Leu Phe Met Asn Tyr Thr Ala Tyr Tyr Pro Ser Pro Pro Gly Ser Pro
            435                 440                 445

Asn Ser Leu Gly Tyr Phe Pro Thr Ala Ala Asn Leu Ser Gly Val Pro
        450                 455                 460

Pro Gln Pro Gly Thr Val Val Arg Met Gln Gly Leu Ala Tyr Asn Thr
465                 470                 475                 480

Gly Val Lys Glu Ile Leu Asn Phe Phe Gln Gly Tyr Gln Tyr Ala Thr
            485                 490                 495

Glu Asp Gly Leu Ile His Thr Asn Asp Gln Ala Arg Thr Leu Pro Lys
        500                 505                 510

Glu Trp Val Cys Ile
        515

<210> SEQ ID NO 3
<211> LENGTH: 14
<212> TYPE: DNA
<213> ORGANISM: Artificial Sequence
<220> FEATURE:
<223> OTHER INFORMATION: Primer

<400> SEQUENCE: 3
ttttgatcaa gctt                                                    14

<210> SEQ ID NO 4
<211> LENGTH: 42
<212> TYPE: DNA
<213> ORGANISM: Artificial Sequence
<220> FEATURE:
<223> OTHER INFORMATION: Adaptor

<400> SEQUENCE: 4
ctaatacgac tcactatagg gctcgagcgg ccgcccgggc ag                     42
```

```
<210> SEQ ID NO 5
<211> LENGTH: 12
<212> TYPE: DNA
<213> ORGANISM: Artificial Sequence
<220> FEATURE:
<223> OTHER INFORMATION: Adaptor

<400> SEQUENCE: 5
ggcccgtcct ag                                                          12

<210> SEQ ID NO 6
<211> LENGTH: 40
<212> TYPE: DNA
<213> ORGANISM: Artificial Sequence
<220> FEATURE:
<223> OTHER INFORMATION: Adaptor

<400> SEQUENCE: 6
gtaatacgac tcactatagg gcagcgtggt cgcggccgag                             40

<210> SEQ ID NO 7
<211> LENGTH: 10
<212> TYPE: DNA
<213> ORGANISM: Artificial Sequence
<220> FEATURE:
<223> OTHER INFORMATION: Adaptor

<400> SEQUENCE: 7
cggctcctag                                                             10

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
ctaatacgac tcactatagg gc                                               22

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
tcgagcggcc gcccgggcag ga                                               22

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
agcgtggtcg cggccgagga                                                  20

<210> SEQ ID NO 11
<211> LENGTH: 25
<212> TYPE: DNA
<213> ORGANISM: Homo Sapiens

<400> SEQUENCE: 11
```

```
atatcgccgc gctcgtcgtc gacaa                                            25

<210> SEQ ID NO 12
<211> LENGTH: 26
<212> TYPE: DNA
<213> ORGANISM: Homo Sapiens

<400> SEQUENCE: 12
agccacacgc agctcattgt agaagg                                           26

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
tcttgaaacc tccagacaca agaa                                             24

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
ggagatggta gacactggtg gagt                                             24

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
tcttgaaacc tccagacaca agaa                                             24

<210> SEQ ID NO 16
<211> LENGTH: 23
<212> TYPE: DNA
<213> ORGANISM: Artificial Sequence
<220> FEATURE:
<223> OTHER INFORMATION: Primer

<400> SEQUENCE: 16
aagttacgat ttggcttcac tgg                                              23

<210> SEQ ID NO 17
<211> LENGTH: 9
<212> TYPE: PRT
<213> ORGANISM: Homo Sapiens

<400> SEQUENCE: 17

Phe Leu Gly Glu Phe Ala Thr Asp Ile
 1               5

<210> SEQ ID NO 18
<211> LENGTH: 9
<212> TYPE: PRT
<213> ORGANISM: Homo Sapiens

<400> SEQUENCE: 18
```

```
Val Leu Phe Ala Cys Glu Glu Tyr Ala
1               5

<210> SEQ ID NO 19
<211> LENGTH: 9
<212> TYPE: PRT
<213> ORGANISM: Homo Sapiens

<400> SEQUENCE: 19

Leu Leu Gly Lys Arg Tyr Ile Glu Leu
1               5

<210> SEQ ID NO 20
<211> LENGTH: 9
<212> TYPE: PRT
<213> ORGANISM: Homo Sapiens

<400> SEQUENCE: 20

Gln Gln Phe Val Pro Pro Thr Asn Val
1               5

<210> SEQ ID NO 21
<211> LENGTH: 9
<212> TYPE: PRT
<213> ORGANISM: Homo Sapiens

<400> SEQUENCE: 21

Cys Ser Ala Glu Glu Met Asn Phe Val
1               5

<210> SEQ ID NO 22
<211> LENGTH: 9
<212> TYPE: PRT
<213> ORGANISM: Homo Sapiens

<400> SEQUENCE: 22

Phe Leu Ser Lys Glu Asn Gln Val Ile
1               5

<210> SEQ ID NO 23
<211> LENGTH: 9
<212> TYPE: PRT
<213> ORGANISM: Homo Sapiens

<400> SEQUENCE: 23

Ser Leu Gly Tyr Phe Pro Thr Ala Ala
1               5

<210> SEQ ID NO 24
<211> LENGTH: 9
<212> TYPE: PRT
<213> ORGANISM: Homo Sapiens

<400> SEQUENCE: 24

Thr Leu Pro Lys Glu Trp Val Cys Ile
1               5

<210> SEQ ID NO 25
<211> LENGTH: 9
<212> TYPE: PRT
<213> ORGANISM: Homo Sapiens

<400> SEQUENCE: 25

Tyr Thr Phe Pro Ala Pro Ala Ala Val
1               5
```

```
<210> SEQ ID NO 26
<211> LENGTH: 9
<212> TYPE: PRT
<213> ORGANISM: Homo Sapiens

<400> SEQUENCE: 26

Tyr Gln Tyr Ala Thr Glu Asp Gly Leu
 1               5
```